US008095224B2

(12) United States Patent
Truex et al.

(10) Patent No.: US 8,095,224 B2
(45) Date of Patent: Jan. 10, 2012

(54) EMI SHIELDED CONDUIT ASSEMBLY FOR AN ACTIVE IMPLANTABLE MEDICAL DEVICE

(75) Inventors: Buehl E. Truex, Glendora, CA (US); Robert A. Stevenson, Canyon Country, CA (US); Richard L. Brendel, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 12/725,903

(22) Filed: Mar. 17, 2010

(65) Prior Publication Data
US 2010/0241206 A1 Sep. 23, 2010

Related U.S. Application Data

(63) Continuation-in-part of application No. 12/489,921, filed on Jun. 23, 2009, now Pat. No. 7,751,903, and a continuation-in-part of application No. 12/407,402, filed on Mar. 19, 2009, and a continuation-in-part of application No. 12/686,272, filed on Jan. 12, 2010, and a continuation-in-part of application No. 12/686,137, filed on Jan. 12, 2010.

(60) Provisional application No. 61/289,332, filed on Dec. 22, 2009, provisional application No. 61/266,411, filed on Dec. 3, 2009.

(51) Int. Cl.
*A61N 1/05* (2006.01)
*A61N 1/00* (2006.01)
(52) U.S. Cl. ........................................ 607/116; 607/115
(58) Field of Classification Search .................. 600/12, 600/439, 420; 607/9, 116
See application file for complete search history.

(56) References Cited

U.S. PATENT DOCUMENTS

| 3,681,612 A | 8/1972 | Vogl et al. |
| 3,745,430 A | 7/1973 | Lunquist et al. |
| 4,188,598 A | 2/1980 | Hunt |
| 4,295,467 A | 10/1981 | Mann et al. |
| 4,320,763 A | 3/1982 | Money |
| 4,424,551 A | 1/1984 | Stevenson et al. |
| 4,431,005 A | 2/1984 | McCormick |

(Continued)

FOREIGN PATENT DOCUMENTS
EP 0466424 A1 1/1992
(Continued)

OTHER PUBLICATIONS

Roger Christoph Luchinger, "Safety Aspects of Cardiac Pacemakers in Magnetic Resonance Imaging," a dissertation submitted to the Swiss Federal Institute of Technology Zurich, 2002, Zurich.

(Continued)

*Primary Examiner* — Carl H. Layno
*Assistant Examiner* — Jon-Eric C. Morales
(74) *Attorney, Agent, or Firm* — Michael F. Scalise

(57) ABSTRACT

An EMI shielded conduit assembly for an active implantable medical device (AIMD) includes an EMI shielded housing for the AIMD, a hermetic feedthrough terminal associated with the AIMD housing, and an electronic circuit board, substrate or network disposed within the AIMD housing remote from the hermetic feedthrough terminal. At least one leadwire extends from the hermetic feedthrough terminal to the remote circuit board, substrate or network. An EMI shield is conductively coupled to the AIMD housing and substantially co-extends about the leadwire in non-conductive relation thereto.

22 Claims, 35 Drawing Sheets

U.S. PATENT DOCUMENTS

| | | |
|---|---|---|
| 4,445,501 A | 5/1984 | Bresler |
| 4,572,198 A | 2/1986 | Codrington |
| 4,643,186 A | 2/1987 | Rosen et al. |
| 4,672,972 A | 6/1987 | Berke |
| 4,754,752 A | 7/1988 | Ginsburg et al. |
| 4,757,820 A | 7/1988 | Itoh |
| 4,766,381 A | 8/1988 | Conturo et al. |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,858,064 A | 8/1989 | Sagawa et al. |
| 4,859,950 A | 8/1989 | Keren |
| 4,932,411 A | 6/1990 | Fritschy et al. |
| 4,960,106 A | 10/1990 | Kubokawa |
| 4,989,608 A | 2/1991 | Ratner |
| 5,019,075 A | 5/1991 | Spears et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,178,618 A | 1/1993 | Kandarpa |
| 5,190,046 A | 3/1993 | Sharman |
| 5,197,468 A | 3/1993 | Proctor et al. |
| 5,211,165 A | 5/1993 | Dumoulin et al. |
| 5,217,010 A | 6/1993 | Tsitlik et al. |
| 5,268,810 A | 12/1993 | DiMarco et al. |
| 5,271,400 A | 12/1993 | Dumoulin et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,331,505 A | 7/1994 | Wilheim |
| 5,333,095 A | 7/1994 | Stevenson et al. |
| 5,334,045 A | 8/1994 | Cappa et al. |
| 5,334,193 A | 8/1994 | Nardelia |
| 5,348,010 A | 9/1994 | Schnall et al. |
| 5,352,979 A | 10/1994 | Conturo |
| 5,358,515 A | 10/1994 | Hurter et al. |
| 5,365,928 A | 11/1994 | Rhinehart et al. |
| 5,370,644 A | 12/1994 | Langberg |
| 5,400,787 A | 3/1995 | Marandos |
| 5,413,104 A | 5/1995 | Buijs et al. |
| 5,419,325 A | 5/1995 | Dumoulin et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,450,090 A | 9/1995 | Gels et al. |
| 5,451,232 A | 9/1995 | Rhinehart et al. |
| 5,462,055 A | 10/1995 | Casey et al. |
| 5,476,095 A | 12/1995 | Schnall et al. |
| 5,491,300 A | 2/1996 | Huppenthal et al. |
| 5,493,259 A | 2/1996 | Blalock et al. |
| 5,498,261 A | 3/1996 | Strul |
| 5,507,743 A | 4/1996 | Edwards |
| 5,512,825 A | 4/1996 | Atalar et al. |
| 5,540,679 A | 7/1996 | Fram et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,591,218 A | 1/1997 | Jacobson |
| 5,620,476 A | 4/1997 | Truex et al. |
| 5,623,241 A | 4/1997 | Minkoff |
| 5,650,759 A | 7/1997 | Hittman et al. |
| 5,662,108 A | 9/1997 | Budd et al. |
| 5,682,897 A | 11/1997 | Pomeranz |
| 5,683,435 A | 11/1997 | Truex et al. |
| 5,685,878 A | 11/1997 | Falwell et al. |
| 5,699,801 A | 12/1997 | Atalar et al. |
| 5,706,810 A | 1/1998 | Rubinsky et al. |
| 5,715,825 A | 2/1998 | Crowley |
| 5,735,887 A | 4/1998 | Barreras et al. |
| 5,757,252 A | 5/1998 | Cho et al. |
| 5,765,779 A | 6/1998 | Hancock et al. |
| 5,769,800 A | 6/1998 | Gelfand et al. |
| 5,772,693 A | 6/1998 | Brownlee |
| 5,775,338 A | 7/1998 | Hastings |
| 5,779,669 A | 7/1998 | Haissaguerre et al. |
| 5,782,891 A | 7/1998 | Hassler et al. |
| 5,792,055 A | 8/1998 | McKinnon |
| 5,822,174 A | 10/1998 | Yamate et al. |
| 5,824,029 A | 10/1998 | Weijand et al. |
| 5,833,608 A | 11/1998 | Acker |
| 5,840,031 A | 11/1998 | Crowley |
| 5,864,234 A | 1/1999 | Ludeke |
| 5,868,674 A | 2/1999 | Glowinski et al. |
| 5,879,347 A | 3/1999 | Saadat |
| 5,891,134 A | 4/1999 | Goble et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,938,609 A | 8/1999 | Pomeranz |
| 5,938,692 A | 8/1999 | Rudie |
| 5,959,336 A | 9/1999 | Barsan |
| 5,964,705 A | 10/1999 | Truwit et al. |
| 5,973,906 A | 10/1999 | Stevenson et al. |
| 5,973,907 A | 10/1999 | Reed |
| 6,004,269 A | 12/1999 | Crowley et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,045,532 A | 4/2000 | Eggers et al. |
| 6,066,136 A | 5/2000 | Geistert |
| 6,099,524 A | 8/2000 | Lipson et al. |
| 6,128,522 A | 10/2000 | Acker et al. |
| 6,129,670 A | 10/2000 | Burdette et al. |
| 6,137,161 A | 10/2000 | Gilliland et al. |
| 6,146,743 A | 11/2000 | Haq et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,226,545 B1 | 5/2001 | Gilderdale |
| 6,238,390 B1 | 5/2001 | Tu et al. |
| 6,263,229 B1 | 7/2001 | Atalar et al. |
| 6,272,370 B1 | 8/2001 | Gillies et al. |
| 6,284,971 B1 | 9/2001 | Atalar et al. |
| 6,332,089 B1 | 12/2001 | Acker et al. |
| 6,370,427 B1 | 4/2002 | Alt et al. |
| 6,373,673 B1 | 4/2002 | Anthony |
| 6,390,996 B1 | 5/2002 | Halperin et al. |
| 6,408,202 B1 | 6/2002 | Lima et al. |
| 6,424,234 B1 | 7/2002 | Stevenson |
| 6,428,537 B1 | 8/2002 | Swanson et al. |
| 6,456,481 B1 | 9/2002 | Stevenson |
| 6,459,935 B1 | 10/2002 | Piersma |
| 6,473,314 B1 | 10/2002 | Custer et al. |
| 6,529,103 B1 | 3/2003 | Brendel et al. |
| 6,539,261 B2 | 3/2003 | Molin |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,593,884 B1 | 7/2003 | Gilboae et al. |
| 6,606,513 B2 | 8/2003 | Lardo et al. |
| 6,628,980 B2 | 9/2003 | Atalar et al. |
| 6,633,780 B1 | 10/2003 | Berger et al. |
| 6,654,628 B1 | 11/2003 | Silber et al. |
| 6,660,116 B2 | 12/2003 | Wolf et al. |
| 6,675,033 B1 | 1/2004 | Lardo et al. |
| 6,690,963 B2 | 2/2004 | Ben-Haim et al. |
| 6,701,176 B1 | 3/2004 | Halperin et al. |
| 6,714,809 B2 | 3/2004 | Lee et al. |
| 6,759,388 B1 | 7/2004 | Marchant et al. |
| 6,765,779 B2 | 7/2004 | Stevenson et al. |
| 6,765,780 B2 | 7/2004 | Brendel et al. |
| 6,771,067 B2 | 8/2004 | Kellman et al. |
| 6,806,806 B2 | 10/2004 | Anthony |
| 6,871,091 B2 | 3/2005 | Wilkinson et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,944,489 B2 | 9/2005 | Zeijlemaker et al. |
| 6,985,775 B2 | 1/2006 | Reinke et al. |
| 7,038,900 B2 | 5/2006 | Stevenson et al. |

| | | |
|---|---|---|
| 7,110,227 B2 | 9/2006 | Anthony et al. |
| 7,113,387 B2 | 9/2006 | Stevenson et al. |
| 7,149,773 B2 | 12/2006 | Haller et al. |
| 7,155,271 B2 | 12/2006 | Halperin et al. |
| 7,174,219 B2 | 2/2007 | Wahlstrand et al. |
| 7,199,995 B2 | 4/2007 | Stevenson |
| 7,236,816 B2 | 6/2007 | Kumar et al. |
| 7,236,834 B2 | 6/2007 | Christopherson et al. |
| 7,276,474 B2 | 10/2007 | Marchant et al. |
| 7,301,748 B2 | 11/2007 | Anthony et al. |
| 7,310,216 B2 | 12/2007 | Stevenson et al. |
| 7,319,905 B1 | 1/2008 | Morgan et al. |
| 7,322,832 B2 | 1/2008 | Kronich et al. |
| 7,327,553 B2 | 2/2008 | Brendel |
| 7,363,090 B2 | 4/2008 | Halperin |
| 7,422,568 B2 | 9/2008 | Yang et al. |
| 7,423,860 B2 | 9/2008 | Anthony et al. |
| 7,428,136 B2 | 9/2008 | Barnett |
| 7,433,168 B2 | 10/2008 | Anthony |
| 7,436,672 B2 | 10/2008 | Ushijima et al. |
| 7,439,449 B1 | 10/2008 | Kumar et al. |
| 7,446,996 B2 | 11/2008 | Togashi |
| 7,450,396 B2 | 11/2008 | Ye et al. |
| 2002/0055678 A1 | 5/2002 | Scott et al. |
| 2002/0095197 A1 | 7/2002 | Lardo et al. |
| 2002/0192688 A1 | 12/2002 | Yang et al. |
| 2003/0028095 A1 | 2/2003 | Tulley et al. |
| 2003/0050557 A1 | 3/2003 | Susil |
| 2004/0015079 A1 | 1/2004 | Berger et al. |
| 2005/0070972 A1 | 3/2005 | Wahlstrand et al. |
| 2005/0201039 A1 | 9/2005 | Stevenson et al. |
| 2005/0222658 A1 | 10/2005 | Hoegh et al. |
| 2006/0009819 A1 | 1/2006 | Przybyszewski |
| 2006/0032665 A1 | 2/2006 | Ice |
| 2006/0085043 A1 | 4/2006 | Stevenson |
| 2006/0100506 A1 | 5/2006 | Halperin |
| 2006/0212096 A1 | 9/2006 | Stevenson |
| 2006/0247684 A1 | 11/2006 | Halperin |
| 2007/0043399 A1* | 2/2007 | Stevenson et al. ............ 607/37 |
| 2007/0112398 A1 | 5/2007 | Stevenson |
| 2007/0123949 A1 | 5/2007 | Dabney et al. |
| 2007/0168005 A1 | 7/2007 | Gray |
| 2007/0203529 A1 | 8/2007 | Iyer et al. |
| 2007/0288058 A1 | 12/2007 | Halperin et al. |
| 2008/0049376 A1 | 2/2008 | Stevenson |
| 2008/0049410 A1 | 2/2008 | Kawaguchi et al. |
| 2008/0065181 A1* | 3/2008 | Stevenson ............ 607/115 |
| 2008/0071313 A1 | 3/2008 | Stevenson |
| 2008/0116997 A1 | 5/2008 | Dabney |
| 2008/0132987 A1 | 6/2008 | Westlund |
| 2008/0158746 A1 | 7/2008 | Anthony et al. |
| 2008/0161886 A1 | 7/2008 | Stevenson et al. |
| 2008/0195180 A1 | 8/2008 | Stevenson et al. |
| 2008/0239622 A1 | 10/2008 | Hsu et al. |
| 2008/0247111 A1 | 10/2008 | Anthony et al. |
| 2008/0247116 A1 | 10/2008 | Kawano et al. |
| 2008/0247117 A1 | 10/2008 | Elam et al. |
| 2008/0264685 A1 | 10/2008 | Park et al. |
| 2008/0277153 A1 | 11/2008 | Teshome et al. |
| 2009/0107717 A1 | 4/2009 | Hsu et al. |
| 2009/0128976 A1 | 5/2009 | Anthony |
| 2009/0139760 A1 | 6/2009 | Tanaka |
| 2009/0180237 A1 | 7/2009 | Hou et al. |
| 2009/0187229 A1 | 7/2009 | Lavie |
| 2011/0147062 A1* | 6/2011 | Stevenson ............ 174/260 |

FOREIGN PATENT DOCUMENTS

| | | |
|---|---|---|
| EP | 0557127 A2 | 8/1993 |
| EP | 0673621 A1 | 9/1995 |
| JP | 6176962 | 6/1994 |
| JP | 994238 | 4/1997 |
| JP | 2001068958 | 3/2001 |
| JP | 2004254257 | 9/2004 |
| JP | 2004289760 | 10/2004 |
| JP | 2005117606 | 4/2005 |
| JP | 2007129565 | 5/2007 |
| WO | WO 87/04080 A2 | 7/1987 |
| WO | WO 92/10213 A1 | 6/1992 |
| WO | WO 94/23782 A1 | 10/1994 |
| WO | WO 97/40396 A1 | 10/1997 |
| WO | WO 98/52461 A1 | 11/1998 |
| WO | WO 00/10456 A1 | 3/2000 |
| WO | WO 00/25672 A1 | 5/2000 |
| WO | WO 02/083016 A1 | 10/2002 |

OTHER PUBLICATIONS

C. Gabriel, S. Gabriel and E. Corthout, "I. Dielectric Properties of Biological Tissues: Literature Survey," 1996, IOP Publishing Ltd.

S. Gabriel, R.W. Lau and C. Gabriel, "II. Dielectric Properties of Biological Tissues: Measurements and the Freuency Range 0 Hz to 20 GHz,"Phys. Med. Biol. 41, 1996, pp. 2251-2269, IOP Publishing Ltd.

S. Gabriel, R.W. Lau and C. Gabriel, "III. The Dielectric Properties of Biological Tissues: Parametric Models for the Dielectric Spectrum of Tissues," Phys. Med. Biol. 41, 1996, pp. 2271-2293, IOP Publishing Ltd.

Constantine A. Balinis, "Advanced Engineering Electromagnetics," 1989, John Wiley & Sons.

Robert C. Susil, Henry R. Halperin, Christopher J. Yeung, Albert C. Lardo and Ergin Atalar, "Multifunctional Interventional Devices for MRI: A Combined Electrophysiology/MRI Catheter," Magnetic Resonance in Medicine, 47: 594-600, 2002.

Mauritis K. Konings, Lambertus W. Bartels, Henk F.M. Smits and Chris J.G. Bakker, "Heating Around Intravascular Guidewires by Resonating RF Waves," Journal of Magnetic Resonance Imaging, 12:79-85, 2000.

Michael J. Weiner, Wilson Greatbatch, Patrick R. Connelly, U.S. Appl. No. 60/269,817, filed Feb. 20, 2001, entitled "Electromagnetic Interference Immune Cardiac Assist System."

Bruce L. Wilkoff M.D., "ICD Extraction Infected/Redundant Leads—Everyday Clinical Practice," Cleveland Clinic, ICD Lead Extraction, Every Day Practice.

Frank G. Shellock, Ph.D., "MRI Issues for Neuromodulation Devices," Institute for Magnetic Resonance Safety, Education, and Research (IMRSER).

* cited by examiner

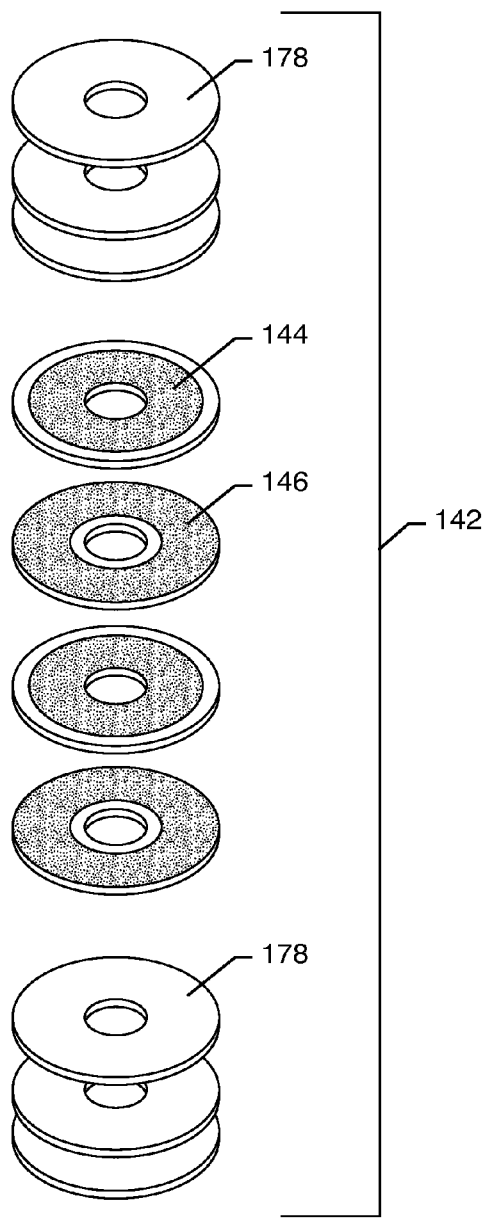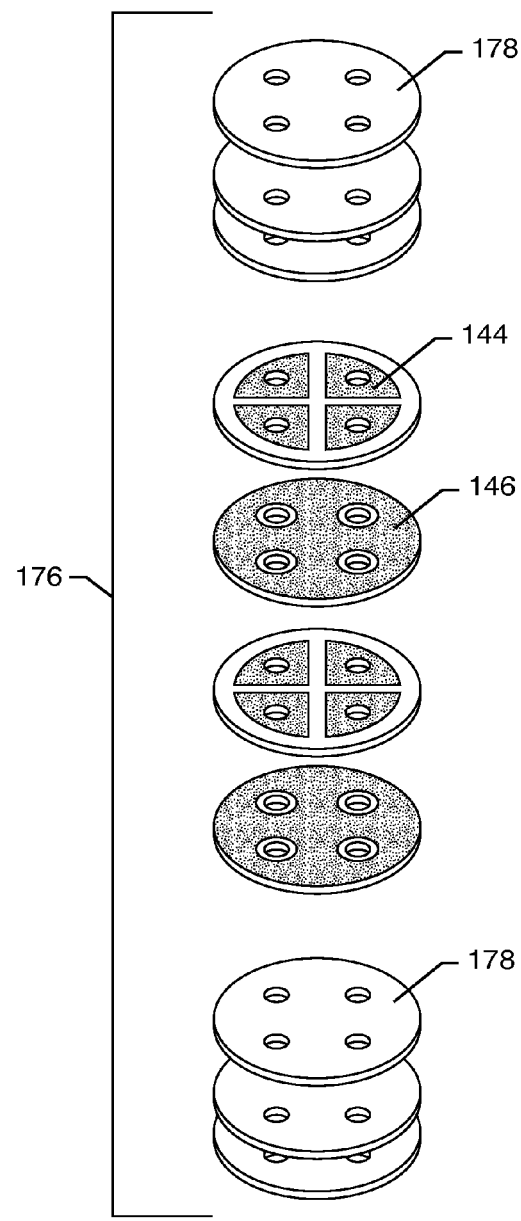
FIG. 12
PRIOR ART
FIG. 13
PRIOR ART

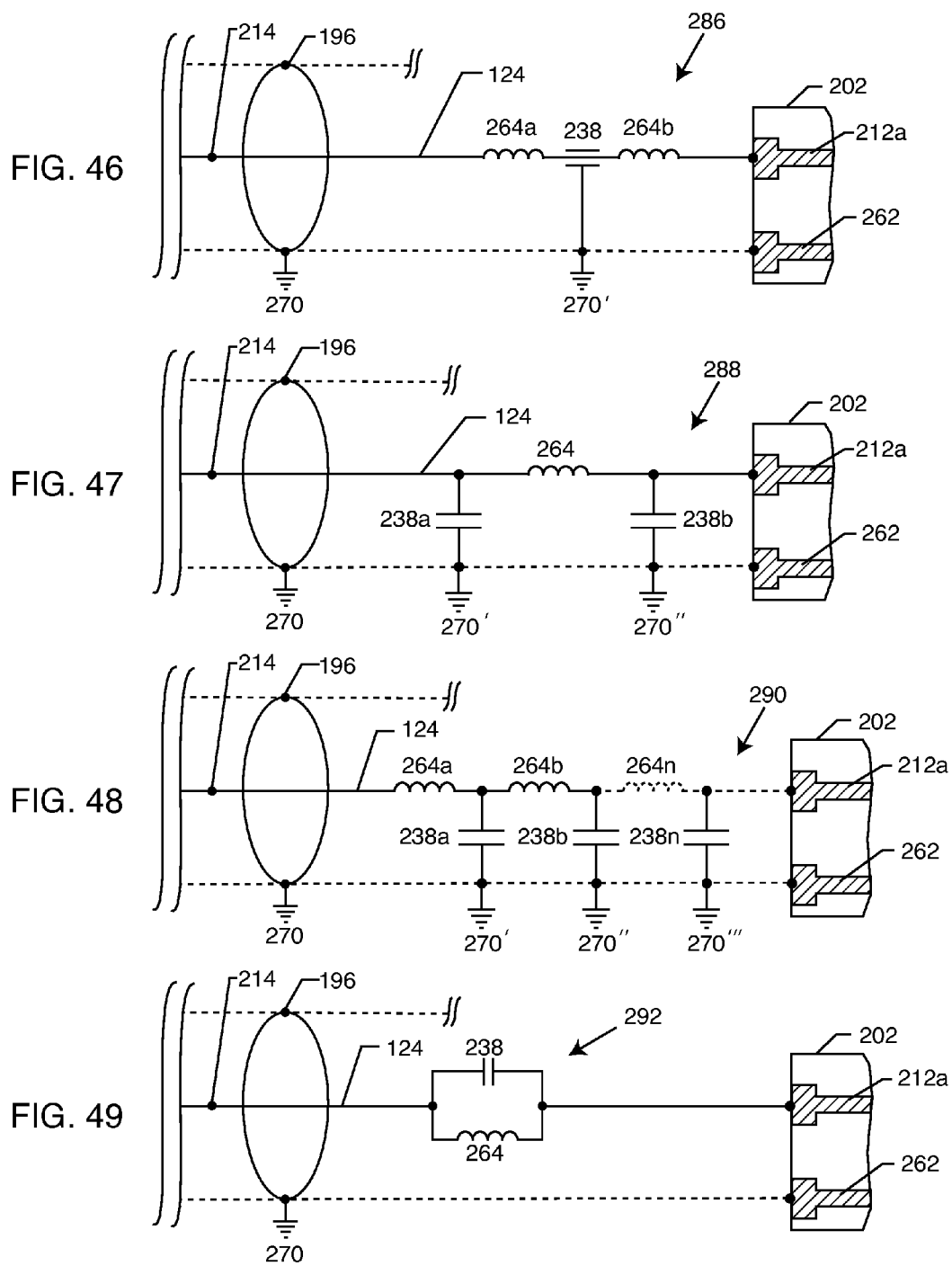

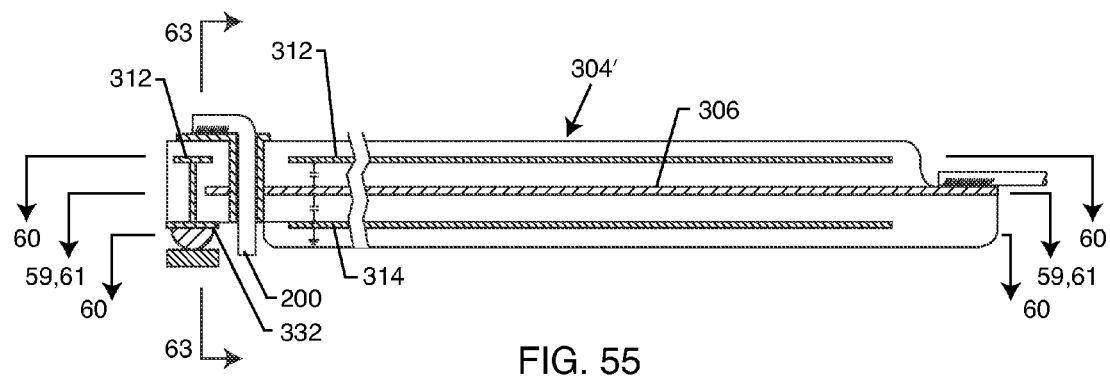
FIG. 55
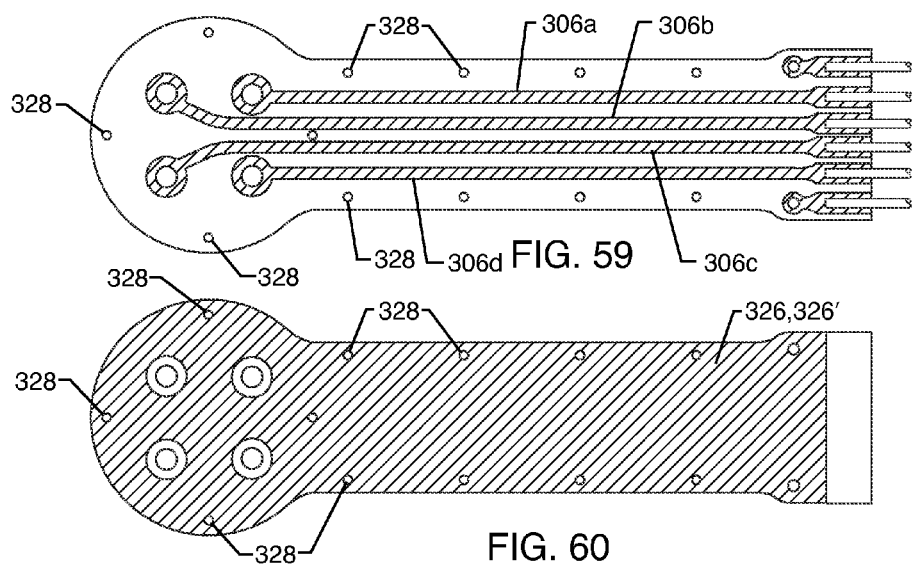
FIG. 59
FIG. 60
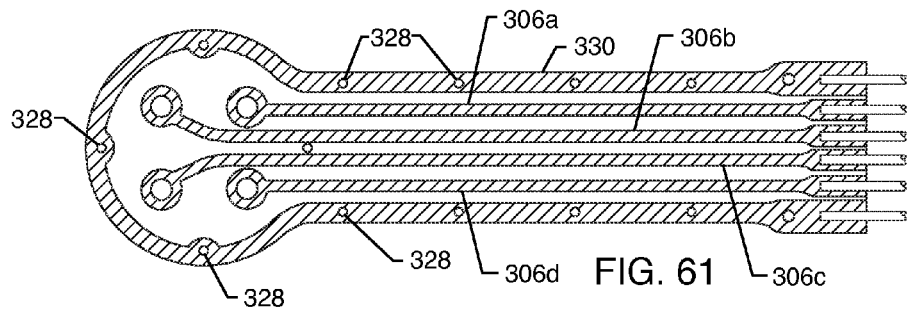
FIG. 61

EMI SHIELDED CONDUIT ASSEMBLY FOR AN ACTIVE IMPLANTABLE MEDICAL DEVICE

This present application claims priority to U.S. application Ser. No. 12/489,921 entitled FREQUENCY SELECTIVE PASSIVE COMPONENT NETWORKS FOR IMPLANTABLE LEADS OF ACTIVE IMPLANTABLE MEDICAL DEVICES UTILIZING AN ENERGY DISSIPATING SURFACE, now U.S. Pat. No. 7,751,903. The present invention generally relates to active implantable medical devices (AIMDs). More particularly, the present invention relates to an EMI shielded conduit for leads extending from the hermetic feedthrough terminal of an active implantable medical device to a remote electronic circuit board, substrate or network located within the AIMD hermetically sealed and electromagnetically shielded housing.

BACKGROUND OF THE INVENTION

Feedthrough hermetic terminals are generally well-known in the art for connecting electrical signals through the housing or case of an AIMD such as those illustrated in FIG. 1. For example, in implantable medical devices such as cardiac pacemakers, shown in FIG. 2, implantable cardioverter defibrillators, and the like, a hermetic terminal 100 comprises one or more conductive terminal pins 102a-102d supported by an insulative structure for feedthrough passage from the exterior to the interior of an AIMD electromagnetic shield housing 104. Many different insulator structures and related mounting methods are known in the art for use in AIMDs, wherein the insulative structure also provides a hermetic seal to prevent entry of body fluids into the housing of the AIMD. However, feedthrough terminal pins are typically connected to one or more implanted leads 106 and 106' are routed from the outside or body fluid side of the AIMD electromagnetic shield housing 104 to cardiac tissues such as those located in a right atrium 108 or in a right ventricle 110. These implanted leads 106 undesirably act as an antenna and thus tend to collect stray electromagnetic interference (EMI) signals from the patient environment for conducted transmission into the interior of the AIMD electromagnetic shield housing 104. Such EMI signals may interfere with the proper operation of AIMD electronic circuits. In general, the AIMD internal electronic circuits are located on a circuit board or substrate 112. Also shown is an RF telemetry pin 114. This acts as a telecommunications antenna coupled from the outside of the AIMD electromagnetic shield housing 104 and the hermetic terminal 100 to the interior of the AIMD to a telecommunications circuit board 116. It will be obvious to those skilled in the art that the circuit board 112 and the telecommunications circuit board 116 can be combined into one overall substrate or they may be broken down into several different substrates located within the AIMD electromagnetic shield housing 104. In many prior art devices, as shown in FIG. 2, there is a ceramic feedthrough filter capacitor 118 which is typical of many prior art devices. In this case the hermetic terminal 100 has been combined directly with frequency selective components such as the ceramic feedthrough filter capacitor 118 or MLCC chip capacitors or the like (not shown), to decouple or divert interfering signals from the point of lead ingress to the shielded housing of the AIMD. Examples of mounting MLCC chip capacitors to the hermetic terminals of AIMDs are more thoroughly described in U.S. Pat. Nos. 5,650,759 and 5,896,267, the contents of which are incorporated herein by reference. It is very important to decouple these signals at their point of ingress to the electromagnetically shielded AIMD so that such stray signals do not re-radiate or couple to sensitive circuits inside the AIMD electromagnetic shield housing 102. FIG. 3 is an example of good practice in the mounting of a prior art broadband EMI filter 120 such as the ceramic feedthrough capacitor 118. In this case, the broadband EMI filter 120 has been mounted directly to or adjacent to the hermetic terminal 100 at the point of ingress of an implanted lead 122. A leadwire 124 routed inside the AIMD electromagnetic shield housing 104 are free of high frequency EMI signals. Accordingly, the leadwires 124 cannot reradiate or couple undesirably to internal circuit board 112 electronic components. FIG. 4 is an example of prior art poor practice. In this case, the onboard EMI filter components have been mounted on the internal circuit board 112 inside of the AIMD electromagnetic shield housing 104. By locating the filtering on the internal circuit board 112, this presents a low impedance which tends to pull an undesirable EMI signal 126 that couples to the implanted lead 122 inside the AIMD electromagnetic shield housing 104. These EMI signals 126 can then reradiate as EMI re-radiation from the internal leadwires 124. It has been shown in the past that such re-radiation can cause AIMD internal electronic circuit malfunction.

Using a cardiac pacemaker as an example, the AIMD electromagnetic shield housing 104 is typically made of titanium, stainless steel, or other suitable biocompatible material which creates an equipotential shield housing. Seams are uniformly laser welded so that there are no openings. An alternative is use of a ceramic, plastic or composite housing with an electromagnetic shield coating disposed on either its interior and/or exterior surfaces. The AIMD electromagnetic shield housing 104 may also be coated with nano materials that form an RF shield. The AIMD electromagnetic shield housing 104 provides hermeticity to protect the sensitive electronic circuits from the intrusion of body fluids.

At high frequencies, the AIMD electromagnetic shield housing 104 both reflects and absorbs incident electromagnetic waves. For example, the evolution and design of such electromagnetically shielded titanium housings have made pacemakers relatively immune to microwave ovens and other high frequency interference sources. The AIMD electromagnetic shield housing 104 also forms a very convenient equipotential surface to which high frequency EMI signals conducted from the implanted leads 122 may be decoupled/diverted. This is typically done using passive or active filter elements which can be mounted directly on or adjacent to the point of AIMD housing implanted lead 122 ingress. In the prior art, the optimal location is to place such bypass (low-pass) filters on or adjacent to the hermetic feedthrough pin terminal. The ceramic feedthrough filter capacitors 118 are typically mounted on the hermetic terminal 100 and provide a low impedance at high frequencies from the leadwires 124 to the AIMD electromagnetic shield housing 104, thereby shorting or diverting high frequency EMI signals to the housing 104. When the high frequency EMI energy is diverted to the AIMD electromagnetic shield housing 104, it simply circulates as eddy currents resulting in a few milliwatts of insignificant power dissipation as a small amount of heat. This results in a miniscule and insignificant temperature rise of the AIMD electromagnetic shield housing 104.

Other (early) prior art designs attempted to provide effective filtering by providing on-board or circuit board substrate mounted low pass EMI filter elements. For example, Intermedics Corporation attempted to use MLCC chip capacitors mounted on a flex cable and/or circuit board or substrate near where the pacemaker sensing amplifiers and microcircuits were placed. Although, the filters did their job and acted as a low impedance, they tended to pull stray EMI RF currents from the outside world to the point of filtering. Because these filters were connected at the end of the flex cable or a leadwire inside of the AIMD housing, these stray EMI signals tended to radiate from the flex cable/leadwires and cross-couple to other sensitive electronics inside the AIMD housing. FIG. 5 is an illustration of the attempt by Intermedics to place an MLCC chip capacitor 128 on a flex cable 130 located within the AIMD electromagnetic shield housing 104. The flex cable 130 was unshielded but could have a ground circuit trace 132. It also has an active circuit trace 134. The MLCC chip capacitor 128 was located between a pair of electrical connections 136a, 136b between the ground circuit trace 132 and the active circuit trace 134. Unfortunately, this created an inductive loop 136 which very effectively reradiated EMI inside the AIMD electromagnetic shield housing 104. In the prior art, this is a dramatic illustration of the need to place filter components directly next to the hermetic terminal 100 connected between a leadwire 124 and a ferrule 138 so that no loops such as the inductive loop 136 are formed but reradiate EMI. This is why the prior art feedthrough capacitor as illustrated in FIGS. 2-13 are generally shown mounted directly to the ferrule 138 and the hermetic terminal 100 of the AIMD. It is a basic principle of good EMI filter engineering that filters be placed at a point of entry to a shielded housing where they can immediately decouple the stray EMI signals to the housing or overall shield of the electronics module.

Therefore it has become common to locate the EMI filters directly at the hermetic terminal 100 which is the point of ingress of the implanted lead 122 from the outside world (body fluid side) to the inside of the AIMD electromagnetic shield housing 104.

As used herein, the term lead, which is synonymous with implanted lead, shall mean the lead or leads that are routed from the exterior of the AIMD electromagnetic shield housing 104 into body tissues. The term leadwire refers to wiring, flex cables or circuit traces inside of the AIMD electromagnetic shield housing 104.

Moreover, as used herein, the term remote, as applied to a circuit board, substrate, capacitor, low pass filter, L-C trap filter, electronic filter, bandstop filter, high voltage suppression array, diode array, and/or short to housing switch network shall mean that any combination of these circuits are mounted remotely relative to the AIMD hermetic seal at or near the distal end of the shielded conduit (usually mounted on an AIMD circuit board or substrate). In general, the novel shielded conduit will both shield the leadwires routed from the AIMD hermetic terminal to the circuit board, remote substrate, capacitor, low pass filter, L-C trap filter, electronic filter, bandstop filter, high voltage suppression array, diode array, and/or short to housing switch network and at the same time also provide a low impedance RF ground return to the overall AIMD electromagnetic shield housing 104 for said remote circuits.

EMI filtered feedthrough hermetic terminals are shown and described in U.S. Pat. No. 4,424,551, U.S. Pat. No. 5,333,095, U.S. Pat. No. 5,905,627, U.S. Pat. No. 5,973,906, U.S. Pat. No. 5,959,829, and U.S. Pat. No. 5,759,197, the contents of which are incorporated herein. There are a number of problems associated with low pass EMI feedthrough filters mounted directly to the hermetic terminal 100, including increased cost, masking a hermetic seal leaker, and reduced reliability.

Cost is increased because it is difficult to reliably mount the filter elements (such as a multipin feedthrough capacitor) on or immediately adjacent to the hermetic terminal subassembly. The hermetic terminal subassembly itself is generally constructed at very high temperature. For example, with a gold brazed alumina hermetic seal subassembly, the gold brazing to the ferrule and terminal pins is done at approximately 800° C. If it is a glass seal composite ceramic subassembly, again very high temperatures are required to re-flow the glass. The subsequent mounting of the EMI filter element is typically done at much lower temperatures. However, when the filter is mounted directly to or against the hermetic terminal subassembly, it is subjected to significant installation stresses. The pacemaker manufacturer generally laser welds the ferrule of the hermetic seal subassembly into the titanium housing of the AIMD. This creates both a thermal shock, thermal rise and mechanical stress which the prior art filter elements must be able to withstand. Installation of these filter elements to the hermetic seal typically involves expensive silver-filled thermal-setting conductive flexible adhesives such as polyimides. In addition to being expensive, these materials are difficult to dispose into the correct positions and require carefully fixturing and cleaning operations. An additional cost comes from the fact that these life-saving devices go through high reliability screening. This includes thermal shock and burn-in of the electronic elements including the low pass filter hermetic seal subassembly. Failure of the electronic filter means that the entire hermetic seal subassembly is also scrap. This is an expensive proposition due to the fact that hermetic terminal subassembly is typically manufactured with biocompatible materials including platinum, platinum iridium pins, gold brazes and the like. In other words, a significant amount of the cost of this subassembly is due to the precious metals involved in its design.

Therefore, a significant problem in the prior art relates to the mounting of feedthrough or MLCC capacitors and other types of EMI filters on or adjacent to a hermetic terminal pin/seal subassembly. In the prior art, such hermetic seals are very carefully tested after installation into the AIMD housing to ensure that they meet a maximum hermetic seal leak rate. This is generally a $1 \times 10-7$ or $1 \times 10^{-8}$ cc per second maximum leak rate. The mounting of a low pass EMI filter assembly generally involves thermal-setting conductive adhesives, epoxies and bonding washers which can mask a leaking hermetic seal. There are a number of patents that allow channels or paths for leak detection including U.S. Pat. No. 6,566,978, the contents of which are incorporated herein. However, these channels/paths are difficult to manufacture and also add cost.

FIG. 1 illustrates various types of active implantable and external medical devices 140a-140i that are currently in use. FIG. 1 is a wire formed diagram of a generic human body showing a number of implanted medical devices. Numeral 140a represents a family of hearing devices which can include the group of cochlear implants, piezoelectric sound bridge transducers and the like. Numeral 140b represents a variety of neurostimulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of the seizure and also providing electrical stimulation to brain tissue to prevent a seizure from actually occurring. The leadwires associated with a deep brain stimulator are often placed using real time MRI imaging. Most commonly such leadwires are placed during real time MRI. Numeral 140c shows a cardiac pacemaker which is well-known in the art. Numeral 140d includes the family of left ventricular assist devices (LVAD's), and artificial hearts, including the recently introduced artificial heart known as the Abiocor. Numeral 140e includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. Numeral 140*f* includes a variety of bone growth stimulators for rapid healing of fractures. Numeral 140*g* includes urinary incontinence devices. Numeral 140*h* includes the family of pain relief spinal cord stimulators and anti-tremor stimulators. Numeral 140*h* also includes an entire family of other types of neurostimulators used to block pain. Numeral 140*i* includes a family of implantable cardioverter defibrillator (ICD) devices and also includes the family of congestive heart failure devices (CHF). This is also known in the art as cardio resynchronization therapy devices, otherwise known as CRT devices.

FIG. 6 is a prior art unipolar discoidal feedthrough capacitor 142, which has an active internal electrode plate set 144 and a ground electrode plate set 146. An inside diameter termination surface 148 is connected electrically to the active electrode plate set 144. An outside diameter termination surface 150 is both solderable and electrically conductive, and it is connected to the ground electrode plate set 146.

FIG. 7 is a cross-section of the unipolar discoidal feedthrough capacitor 142 of FIG. 6 shown mounted to a feedthrough hermetic terminal 152 of an active implantable medical device (AIMD). In prior art discoidal feedthrough capacitor devices 142, the leadwire 124 is continuous. The feedthrough hermetic terminal 152 is attached to, typically, a titanium housing 154, for example, of a cardiac pacemaker. An insulator 156, like alumina ceramic or glass, is disposed within the ferrule 138 and forms a hermetic seal against body fluids. The leadwire 124 extends through the feedthrough hermetic terminal 152, passing through aligned passageways through the insulator 156 and the unipolar discoidal feedthrough capacitor 142. A gold braze 158 forms a hermetic seal joint between the leadwire 124 and the insulator 156. A second gold braze 160 forms a hermetic seal joint between the alumina insulator 156 and the ferrule 138. A laser weld 162 provides a hermetic seal joint between the ferrule 138 and the titanium housing 154. The unipolar discoidal feedthrough capacitor 142 is shown surface mounted in accordance with U.S. Pat. No. 5,333,095, and has an electrical connection 164 between its inside diameter metallization 148 and hence the active electrode plate set 144 and the leadwire 124. There is also an outside diameter electrical connection 164 which connects to the outside diameter metallization 150 and hence the ground electrode plate set 146 to the ferrule 138. Feedthrough capacitors are very efficient high frequency devices that have minimal series inductance. This allows them to operate as EMI filters over very broad frequency ranges.

Referring once again to FIG. 7, one can see that another way to describe a prior art unipolar discoidal feedthrough capacitor 142 is as a three-terminal capacitor. Three-terminal devices generally act as transmission lines. One can see that there is a current 168 that passes into the leadwire 124. On the body fluid side there is generally an implanted lead 122 which can undesirably act as an antenna which can pick up energy from environmental emitters. This energy is known as electromagnetic interference (EMI). Cell phones, microwave ovens and the like have all been implicated in causing interference with active implantable medical devices. If this interference enters the leadwire 124 at a first terminal 170 (FIG. 7), it is attenuated along its length by the unipolar discoidal feedthrough capacitor 142. Upon exiting, the undesirable high frequency EMI has been cleaned off of the normal low frequency circuit current (such as pacemaker pacing pulses or biologic frequency sensors) so that the high frequency EMI has been significantly attenuated. Another way of looking at this is as the high frequency energy passes from the first terminal 170 to a second terminal 172 (FIGS. 7 and 8), it is diverted through the unipolar discoidal feedthrough capacitor 142 to a ground terminal 174 which is also known as the third terminal or terminal 3. In this case, the ground terminal 174 is the connection to the overall electromagnetically shielded housing of the AIMD. The unipolar discoidal feedthrough capacitor 142 of FIGS. 6-8, diverts unwanted high frequency EMI signals from the leadwire 124 to the AIMD electromagnetic shield housing 104 of the AIMD where it dissipates as a few milliwatts of harmless thermal energy.

The unipolar discoidal feedthrough capacitor 142 also performs two other important functions: (a) the internal active electrodes 144 and the internal ground electrodes 146 act as a continuous part of the overall electromagnetic shield housing of the electronic device or module which physically blocks direct entry of high frequency RF energy through the feedthrough hermetic terminal 152 or equivalent opening for leadwire ingress and egress in the otherwise completely shielded housing (such RF energy, if it does penetrate inside the shielded housing can couple to and interfere with sensitive electronic circuitry), and; (b) the unipolar discoidal feedthrough capacitor 142 very effectively shunts undesired high frequency EMI signals off of the leadwires 124 to the overall shield housing where such energy is dissipated in eddy currents resulting in a very small temperature rise.

FIG. 8 is a schematic diagram showing the unipolar discoidal feedthrough capacitor 142 previously described in connection with FIGS. 6 and 7. As one can see, it is a three-terminal device consistent with the first terminal 170, the second terminal 172 and the ground terminal 174 illustrated in FIG. 7.

FIG. 9 is a quadpolar prior art feedthrough capacitor 176 which is similar in construction to that previously described in FIG. 6 except that it has four through holes.

FIG. 10 is a cross-section showing the internal active electrodes 144 and ground electrodes 146 of the quadpolar feedthrough capacitor 176 of FIG. 9.

FIG. 11 is a schematic diagram showing the four discrete feedthrough capacitors comprising the quadpolar feedthrough capacitor 176 of FIGS. 9 and 10.

FIG. 12 is an exploded electrode view showing the inner and outer diameter electrodes of the unipolar discoidal feedthrough capacitor 142 of FIGS. 6 and 7. One can see the active electrode plates set 144 and the ground electrode plate set 146. A cover layer 178 is put on the top and bottom for added electrical installation and mechanical strength.

FIG. 13 is an exploded view of the interior electrodes of the prior art quadpolar feedthrough capacitor 176 of FIG. 9. The active electrode plate sets are shown as 144 and the ground electrode plates are shown as 146. The cover layers 178 serve the same purpose as previously described in connection with FIG. 12.

FIG. 14 is a prior art monolithic ceramic capacitor (MLCC) 180. These are made by the hundreds of millions per day to service consumer electronics and other markets. Virtually all computers, cell phones and other types of electronic devices have many of these. One can see that the MLCC 180 has a body 182 generally consisting of a high dielectric constant ceramic such as barium titinate. It also has a pair of solderable termination surfaces 184, 184' at either end. These solderable termination surfaces 184, 184' provide a convenient way to make a connection to the internal electrode plates 144, 146 of the MLCC capacitor 180. FIG. 14 can also take the shape and characteristics of a number of other types of capacitor technologies, including rectangular, cylindrical, round, tantalum, aluminum electrolytic, stacked film or any other type of capacitor technology.

FIG. 15 is a sectional view taken from section 15-15 in FIG. 14. The MCLL 180 includes a left hand electrode plate set 186 and a right hand electrode plate set 188. One can see that the left hand electrode plate set 186 is electrically connected to the external metallization surface 184. The opposite, right hand electrode plate set 188 is shown connected to the external metallization surface 184'. Prior art MLCC 180 and equivalent chip capacitors are also known as two-terminal capacitors. That is, there are only two ways electrical energy can connect to the body of the capacitor. In FIGS. 14 and 15, the first terminal 170 is on the left side and the second terminal 172 is on the right side.

FIG. 16 is the schematic diagram of the MLCC chip capacitor 180 illustrated in FIGS. 14 and 15.

FIG. 17 is a different type of prior art MLCC feedthrough capacitor 180 that is built into a special configuration known in the art by some as a flat-through capacitor 190. At low frequencies, the flat-through capacitor 190 exhibits ideal capacitance behavior versus frequency. That is, its attenuation curve versus frequency is nearly ideal. This is because it is truly a three-terminal device which acts as a transmission line in a manner similar to those of prior art unipolar discoidal feedthrough capacitors 142. This is better understood by referring to its internal electrode plate geometry as shown in FIG. 18, wherein a through or active electrode plate 144 is sandwiched between two ground electrode plates 146, 146'. The through or active electrode plate 144 is connected at both ends by termination surfaces 184 and 184'. When the flat-through capacitor 190 is mounted between the circuit trace lands 192 and 192' as shown in FIG. 17, this connects the circuit trace together between points 192 and 192'. Referring to the active electrode plate 144 in FIG. 18, one can see the current 168 entering. If this is a high frequency EMI current, it will be attenuated along its length by the capacitance of the flat-through capacitor 190 and emerge as a much smaller in amplitude EMI signal at the second terminal 172 as 168'. Similar to the unipolar discoidal feedthrough capacitor 142, the flat-through capacitor 190 is also a three-terminal capacitor as illustrated in FIG. 17. The point where the current 168 ingresses is at the first terminal 170. The point where the circuit current 170' egresses is known as the second terminal 172. Lastly, the ground terminal 174 is known as the third terminal. In other words, any RF currents that are flowing down the circuit trace lands 192 must pass through the active electrode plate 144 of the flathrough capacitor 190. This means that any RF signals are exposed for the full length of the active electrode plate 144 between the ground electrode plates 146, 146' and the capacitance that is formed between them. This has the effect of making a very novel shape for a three-terminal feedthrough capacitor. One negative to this type of flat-through capacitor 190 is that it is not conveniently mountable in such a way that it becomes an integral part of an overall shield.

There is always a frequency at which an undesirable RF coupling 194 (FIG. 17) across the device will occur. This usually does not happen until 100 MHz or above. At very high frequencies, such as above 1 GHz, this problem becomes quite serious. Another negative, as compared to the prior art unipolar discoidal feedthrough capacitor 142 (where the circuit current 168 passes through a robust leadwire 124 in a feedthrough hole), is that the flat-through capacitor 190 circuit current 168 must flow through the active electrodes 144 of the flat-through capacitor 190 itself (in the prior art unipolar discoidal feedthrough capacitor 142, the only current 168 that flows in the active electrodes 144 is high frequency EMI currents). Monolithic ceramic manufacturing limitations on electrode thickness and conductivity means that the prior art flat-through capacitors 190 have relatively high series resistance and can only be rated to a few hundred milliamps or a few amps at best (however, an implantable defibrillator must deliver a high voltage pulse of over 20-amps). Prior art MLCC and flat-through electrodes must be kept relatively thin to promote ceramic grain growth through the electrodes in order to keep the capacitor layers from delaminating during manufacturing or worse yet, during subsequent mechanical or thermal shocks which can cause latent failures.

FIG. 19 is a schematic diagram of the prior art flat-through capacitor 190 shown in FIG. 17. Note that this schematic diagram is the same as that for the unipolar discoidal feedthrough capacitor 142 shown in FIGS. 6 and 7. The difference is that the unipolar discoidal feedthrough capacitor 142 is inherently configured to be mounted as an integral part of an overall shield which precludes the problem of the RF coupling 194 (see FIGS. 9-11).

FIG. 20 illustrates the attenuation versus frequency response curve which is shown generically for the flat-through capacitor 192 of FIG. 17. If it were not for cross-coupling of RF energy, it would perform as an ideal or nearly perfect capacitor. However, because of this cross-coupling, there is always going to be a certain frequency at which the attenuation starts to parasitically drop off as shown. This drop off is very undesirable in active implantable medical device (AIMD) applications in that there would be less protection against high frequency EMI emitters such as cellular phones and the like. This parasitic drop off in attenuation due to cross-coupling is even a worse problem in military and space applications where EMI filter attenuation requirements of up to 10 or even 18 GHz, is important (implantable medical applications do not generally require filtering much above 3 GHz due to the effective reflection and absorption of human skin of RF energy at frequencies above 3 GHz). Space and military circuits have to operate in the presence of extremely high frequency emitters, such as GHz radars and the like.

Accordingly, there is a need for an EMI shielded conduit assembly for an active implantable medical device, and a related method of remotely mounting the low pass EMI filter or other electronic component or assembly at a location remote from the hermetic terminal subassembly. Ideally, this mounting would be either at or near the circuit board or substrate where automated low cost electronic assembly methods could be used. Moreover, there is a need for providing a shielded conduit which has the effect of extending the overall electromagnetic shield (titanium housing) to a remote location at the location of the low pass filter. Specifically, in the case of a feedthrough capacitor, there is a need for it to be mounted inside of the conduit or even on the circuit board. Ideally, the shield should extend all the way to the low pass filter elements such that no coupling or re-radiation inside of the device can occur. The present invention fulfills these needs and provides other benefits.

SUMMARY OF THE INVENTION

An EMI shielded conduit assembly for an active implantable medical device (AIMD) includes an EMI shield housing for the AIMD, a hermetic feedthrough terminal associated with the AIMD housing, an electronic circuit board, substrate or network disposed within the AIMD housing remote from the hermetic feedthrough terminal, at least one leadwire extending from the hermetic feedthrough terminal to the remote electronic circuit board, substrate or network and an EMI shield conductively coupled to the AIMD housing and substantially co-extending about the leadwire in non-conductive relation thereto. The EMI shielded conduit assembly may include a plurality of leadwires extending from the hermetic feedthrough terminal to the remote electronic circuit board, substrate or network. A non-conductive insulator may be disposed between each leadwire and its respective EMI shield. In this regard, the EMI shield may include multiple EMI shields conductively coupled to the AIMD housing and each co-extensively extending about at least one respective leadwire in non-conductive relation thereto.

The electronic circuit board, substrate or network preferably includes a low pass EMI filter, an L-C trap, a bandstop filter, a programmable short-to-housing switch network, or a combination thereof. The low pass EMI filter may include a capacitor, a feedthrough capacitor, an MLCC chip capacitor, a flat-through capacitor, an X2Y attenuator, a multi-element low-pass filter, an active electronic filter, or a combination thereof. The low pass EMI filter and the L-C trap may be grounded to the EMI shield. Moreover, the low pass filter, the L-C trap, or the bandstop filter may be disposed on the circuit board or the substrate. Preferably, the EMI shield extends from the hermetic feedthrough terminal to the low pass EMI filter, the L-C trap, or the bandstop filter.

The EMI shielded conduit assembly may further include a high voltage suppression network associated with the remote electronic circuit board, substrate or network. The high voltage suppression network is preferably grounded to the EMI shield. In one embodiment, the high voltage suppression network includes a diode array. The EMI shield itself preferably includes a conductive heat-shrink tubing, a conductive foil, wire, braid, mesh, circuit trace, or solid tubular material. The EMI shield is preferably radially spaced from the leadwires and may include a flex cable embodying at least one of the leadwires and the EMI shield.

The hermetic feedthrough terminal may include a ferrule conductively coupled to the AIMD housing. In this embodiment, the EMI shield is preferably conductively coupled to the ferrule. Additionally, the AIMD housing may further include a conductive equipotential surface, such as a metallic can.

Other features and advantages of the present invention will become apparent from the following more detailed description, when taken in conjunction with the accompanying drawings, which illustrate, by way of example, the principles of the invention

BRIEF DESCRIPTION OF THE DRAWINGS

The accompanying drawings illustrate the invention. In such drawings:

FIG. 12 is an exploded perspective view illustrating the electrode lay-ups of the unipolar feedthrough capacitor of FIGS. 6 and 7;

FIG. 13 is an exploded perspective view illustrating the electrode lay-ups of the quadpolar feedthrough capacitor shown in FIGS. 9 and 10;

FIG. 46 is a circuit diagram illustrating a T filter;

FIG. 47 is a circuit diagram illustrating a PI filter;

FIG. 48 is a circuit diagram illustrating an n-element low pass filter;

FIG. 49 is a circuit diagram illustrating a bandstop filter in series with a leadwire having an inductor and a capacitor in parallel;

FIG. 55 is a cross-sectional view of an improved flex cable embodying the present invention;

FIG. 59 is a sectional view taken along line 59-59 of FIG. 55;

FIG. 60 is a sectional view taken along line 60-60 of FIG. 55, illustrating one of a pair of coaxially surrounding shields disposed about the circuit trace;

FIG. 61 is a sectional view taken along the line 61-61 of FIG. 55, illustrating an alternative to the internal circuit traces described with respect to FIG. 59;

DETAILED DESCRIPTION OF THE PREFERRED EMBODIMENTS

In accordance with the present invention, the EMI shielded conduit assembly for an active implantable medical device (AIMD) comprises: (1) an EMI shielded housing for the AIMD; (2) a hermetic feedthrough terminal associated with the AIMD housing; (3) an electronic circuit board, substrate or network disposed within the AIMD housing remote from the hermetic feedthrough terminal; (4) at least one leadwire extending from the hermetic feedthrough terminal to the remote electronic circuit board, substrate or network; and (5) an EMI shield conductively coupled to the AIMD housing and co-extensively extending about the at least one leadwire in non-conductive relation. In the following detailed description, functionally equivalent components of various embodiments will be referred to by the same reference numbers or letters.

Accordingly, by removing the filter capacitor or low pass filter or other components from the hermetic seal to a remote location, one can test the hermetic seal free from any adjunct sealants and free from any concerns that subsequent assembly may mask a leaking hermetic seal subassembly.

Figure 21:
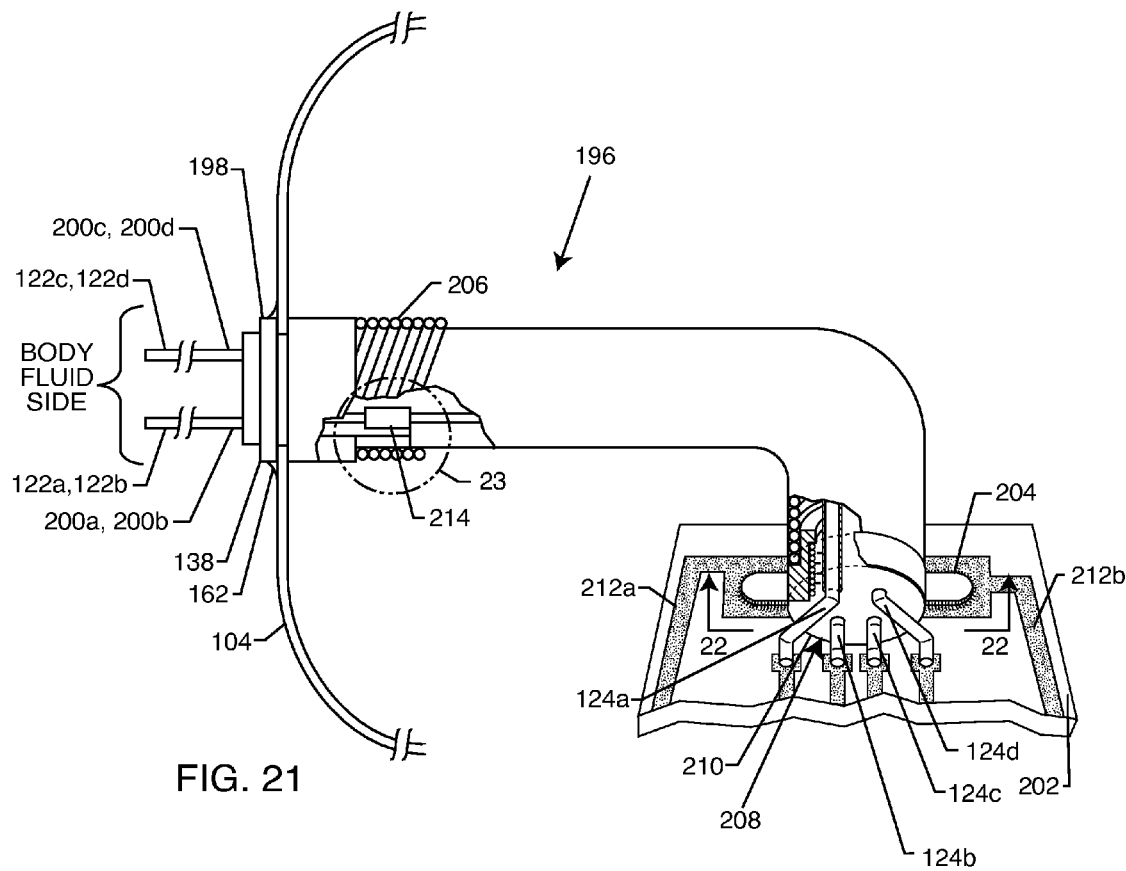
FIG. 21 is a fragmented and partially sectional view of an EMI shielded conduit assembly for an AIMD, in accordance with the present invention.

FIG. 21 illustrates the basic components of an EMI shielded conduit assembly 196 for an active implantable medical device (AIMD) as outlined above. The conductive ferrule 138 of a hermetic seal 198 is generally of titanium, platinum, or similar biocompatible metal. The laser weld 162 hermetically seals the AIMD electromagnetic housing 104. The hermetic seal 198 embodies a set of terminal pins 200a-200d attached to the implanted leads 122a-122d, which the terminal pins 200a-200d pass through in non-conductive relation. In a cardiac pacemaker application, there is a connector header block mounted outside the AIMD electromagnetic shield housing 104 in accordance with ISO standard IS-1 or IS-4. For simplicity, these prior art headers and connector blocks are not shown. The hermetic seal 198 typically comprises an alumina ceramic or glass insulator (not shown). It is important that the metallic ferrule 138 be an electrically continuous part of the overall AIMD electromagnetic shield housing 104.

The novel EMI shielded conduit assembly 196 connects electrically to the ferrule 138 of the hermetic terminal seal 198. If there is no ferrule present, the EMI shielded conduit assembly 196 may be electrically connected directly to the AIMD electromagnetic shield housing 104. This conductive EMI shielded conduit assembly 196 extends down to an AIMD electronic circuit board, substrate or network 202. In a preferred embodiment, there are a set of conductive support tabs or feet 204 which are electrically connected to an EMI shield 206. As will be further described, the EMI shield 206 can be continuous solid (flexible) tubing, a shield braid, shielded wires, shielded foil, shielded mesh or even conductive circuit traces within a flex cable. It is important that this EMI shield 206 at least partially co-extensively surround the AIMD internal leadwires 124a-124d. This is because the implanted leads 122a-122d, for example, in the case of a cardiac pacemaker, are routed endocardially to cardiac chambers. These implanted leads 122a-122d can also undesirably act as antennas which can pick up stray and unwanted EMI. One purpose of the conductive conduit or the EMI shield 206 is to prevent re-radiation of the EMI inside the AIMD electromagnetic shield housing 104 before it reaches the electronic circuit board, substrate or network 202 at location 208. In this case, a filter capacitor component 210 is shown as an integral part of the overall EMI shielded conduit assembly 196. As will be shown in subsequent drawings, it can be eliminated, it can be placed on the circuit board 202 or consist of alternate components. The EMI filter, in this case, is a quadpolar low pass filter consisting of the filter capacitor component 210. This is identical to the prior art quadpolar feedthrough capacitor 176 shown in FIGS. 9-11 and 13. The conductive support feet 204 are electrically connected to the EMI shield 206 and are also connected to a set of ground circuit traces 212a-212b on the circuit board 202. The implanted leads 124a-124d and the hermetic terminal pins 200a-200d are exposed to body fluids and have to be of suitable biocompatible materials, such as platinum, platinum-iridium, niobium, palladium and the like. A circuit junction connection 214 is shown to make a connection from the hermetic seal terminal pin(s) 200a-200d to the much lower cost leadwires 124a-124d. The circuit junction connections 214 can be a simple solder joint, a crimp or twist connector as illustrated, a plug-in pin, or any other method of joining two leadwires together.

Figure 23:
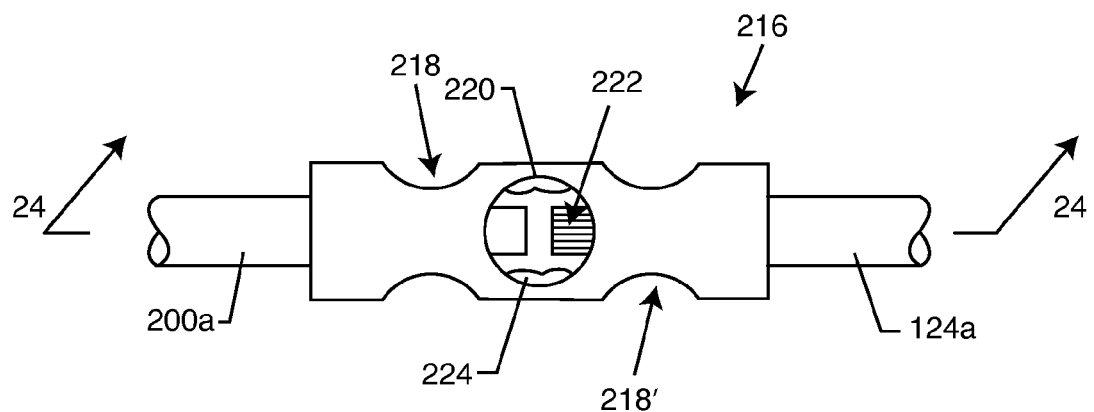
FIG. 23 is an enlarged view of a circuit junction, taken of the area indicated by the reference number 23 in FIG. 21.

FIG. 23 is a blown-up view of the circuit junction connection 214 of FIG. 21. Shown is a novel crimp connection 216. The crimp connection 216 has a crimp 218 to the hermetic terminal pin 200a and also includes a crimp 218' to the leadwire 124a. An optional hole 220 has been provided for convenient soldering or laser welding of an exposed leadwire end 222. In a preferred embodiment, the leadwire 124a would be of stranded insulated wire. One can see that the insulation has been removed by the leadwire end 222 so that it will contact soldering, the crimp 218, the laser weld 162, and a braze or thermal-setting conductive adhesive material 224.

Figure 24:
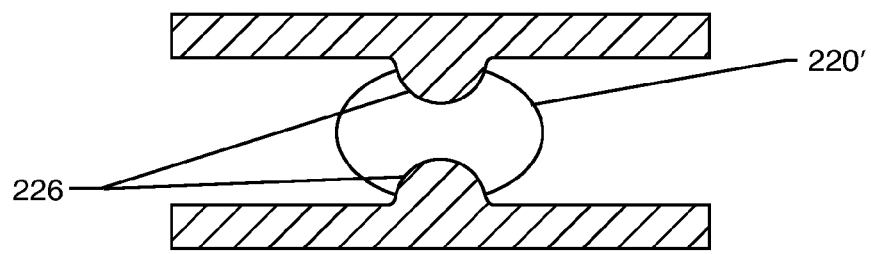
FIG. 24 is an enlarged cross-sectional view of the circuit junction, taken along the line 24-24 of FIG. 23.

FIG. 24 is a cross-section taken generally from section 24-24 from FIG. 23. The cross-section is shown prior to crimping and shows that the hole 220 need not be round. In fact, a hole 220' in FIG. 24 is oval, but could also be elliptical, or any other shape. Also shown are a pair of optional internal indents 226 which are convenient when one places the terminal pin 200a and the leadwire 124a into place. The indents 226 stop the leadwire from pushing in too far so it can be properly located for crimping.

Circuit junction connection 214 can be eliminated if the wires coming out of the hermetic seal 198 are made sufficiently long enough. In this case, insulation tubing (not shown) would be placed over each of the leadwires 124a-124d (which in this case, become the same as the terminal pins 200a-200d). Said tubing could also be non-conductive heat-shrink tubing. Then the EMI shield 206 could be slipped over the leadwires and then electrically connected to the AIMD electromagnetic shield housing 104 or to the conductive ferrule 138 of the hermetic seal 198.

Figure 1:
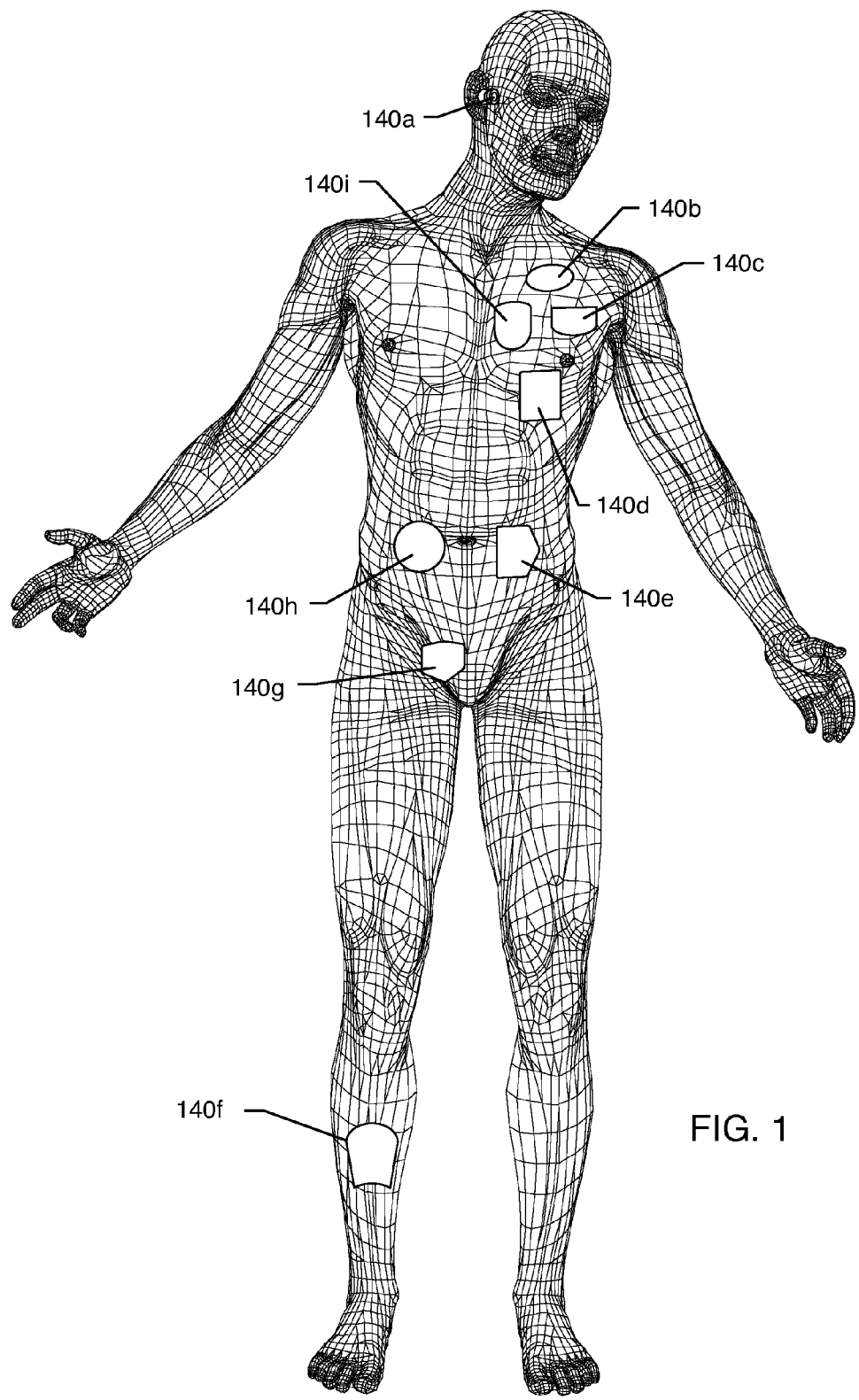
FIG. 1 is a wire-form diagram of a generic human body showing a number of exemplary active implantable medical devices (AIMD)
Figure 2:
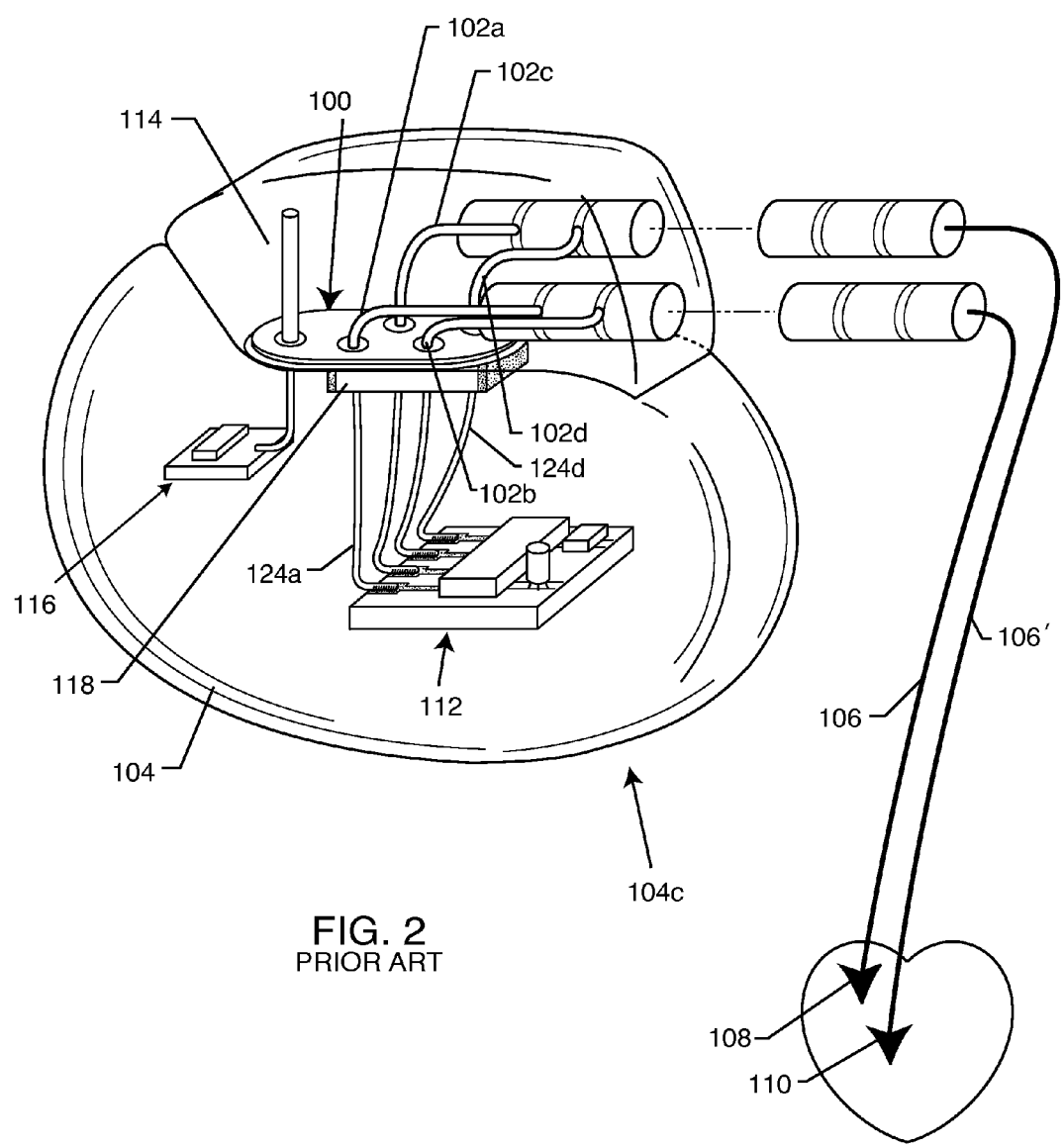
FIG. 2 is an illustration of a human heart and a sample cardiac pacemaker having implantable leads implanted in the right atrium or right ventricular of the heart.
Figure 3:
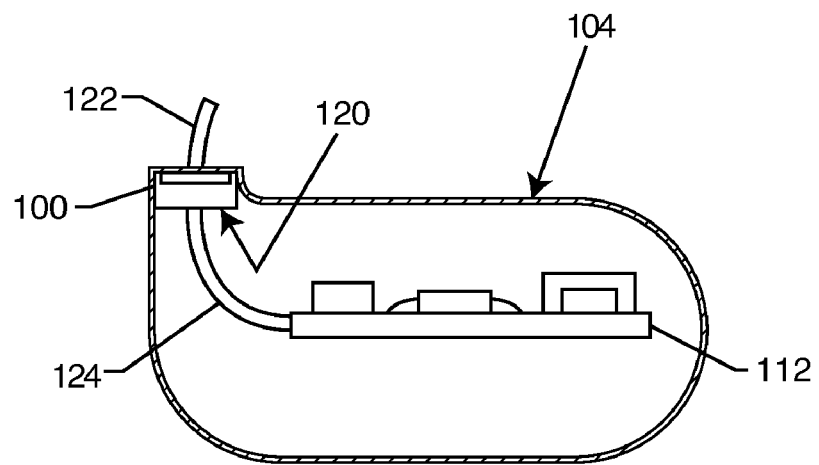
FIG. 3 is a sectional view of an AIMD housing having the EMI filter mounted directly to the hermetic terminal at the point of ingress of the implantable leadwires.
Figure 4:
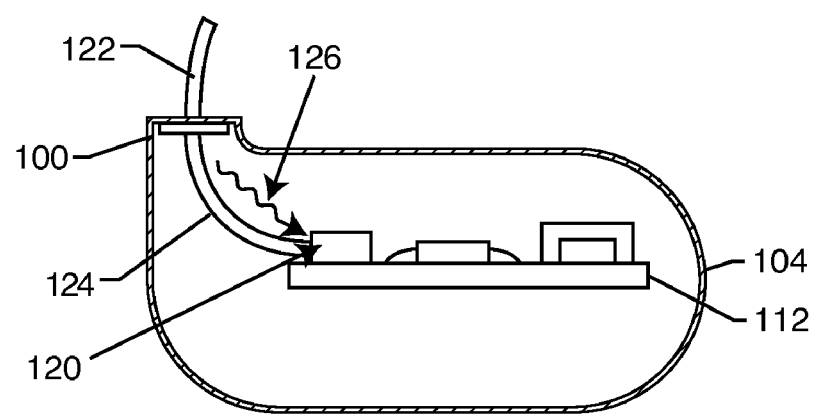
FIG. 4 is a sectional view similar to FIG. 3, of an AIMD housing having an onboard EMI filter on the internal circuit board such that EMI signals re-radiate from internal leadwires to the internal circuit board.
Figure 5:
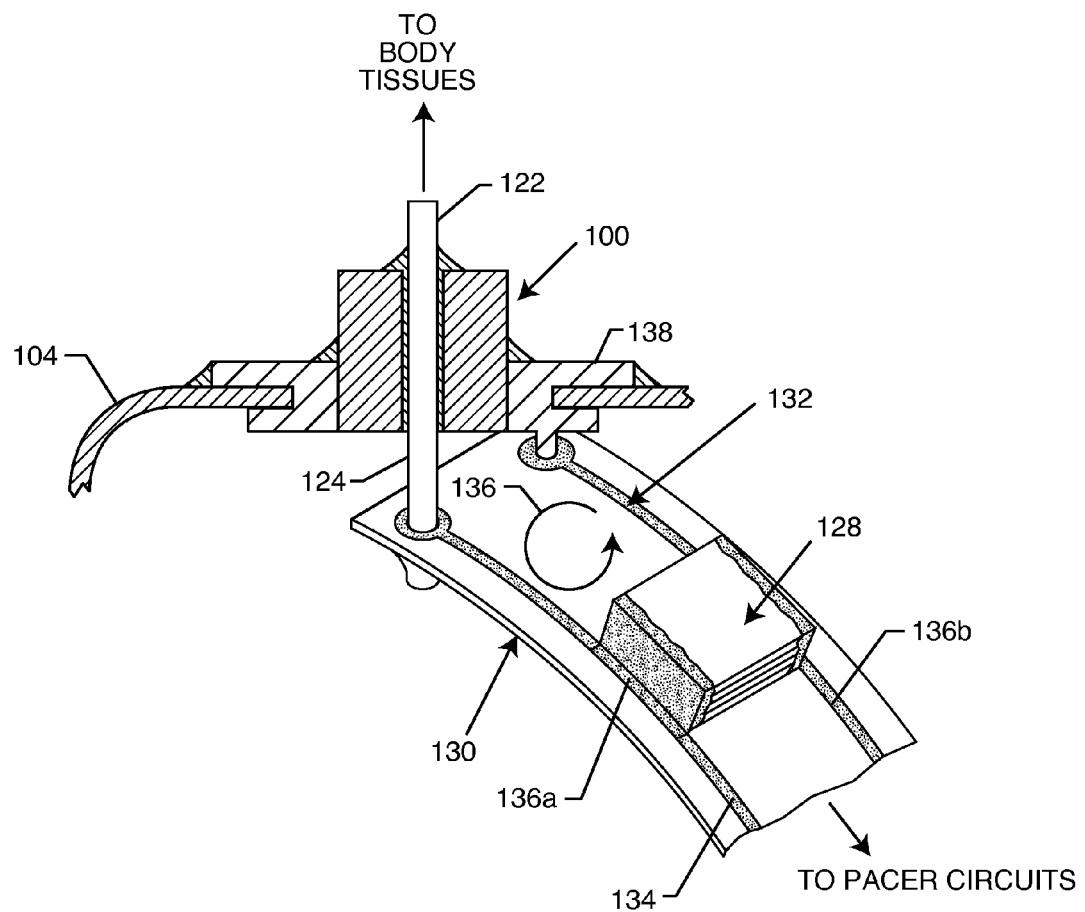
FIG. 5 illustrates an MLCC chip capacitor on a flex cable located within the AIMD housing.
Figure 6:
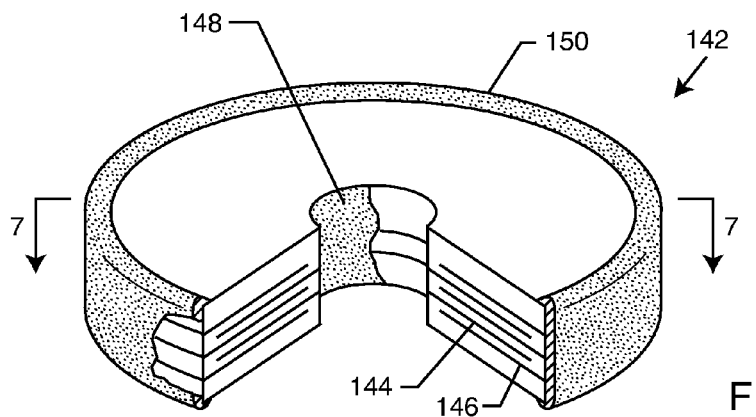
FIG. 6 is a fragmented perspective view of a prior art unipolar discoidal feedthrough capacitor.
Figure 7:
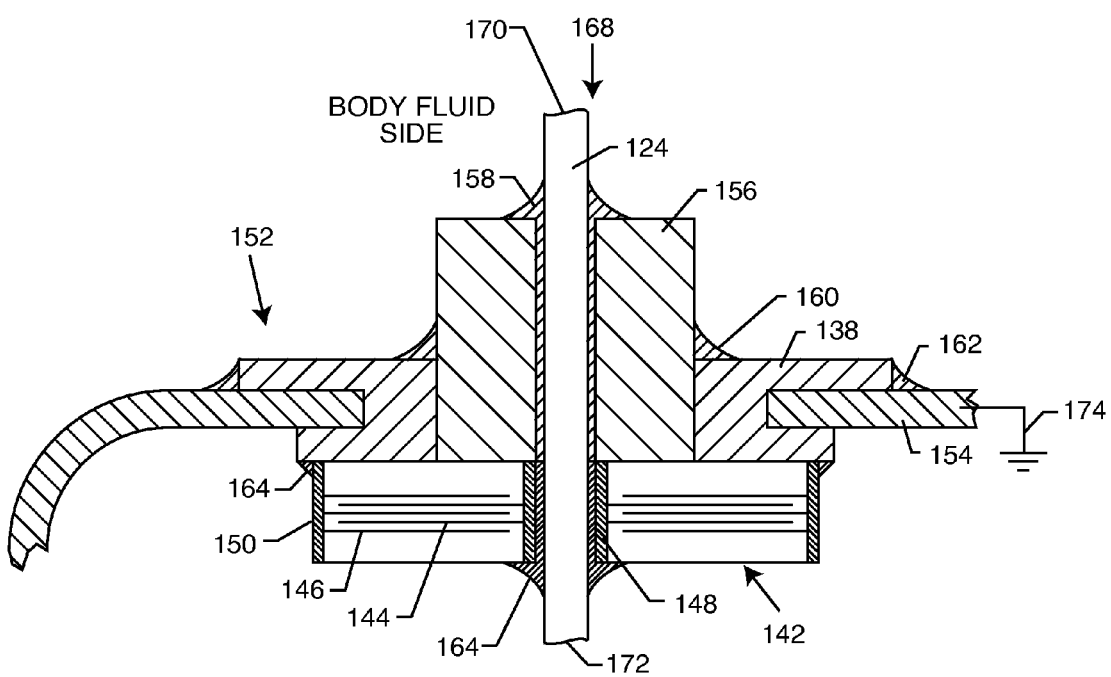
FIG. 7 is a cross-sectional view of the feedthrough capacitor of FIG. 6, taken about the line 7-7, shown mounted to a hermetic terminal of an AIMD.
Figure 8:
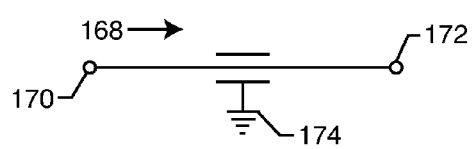
FIG. 8 is an electrical schematic diagram of the feedthrough capacitor of FIGS. 6 and 7.
Figure 9:
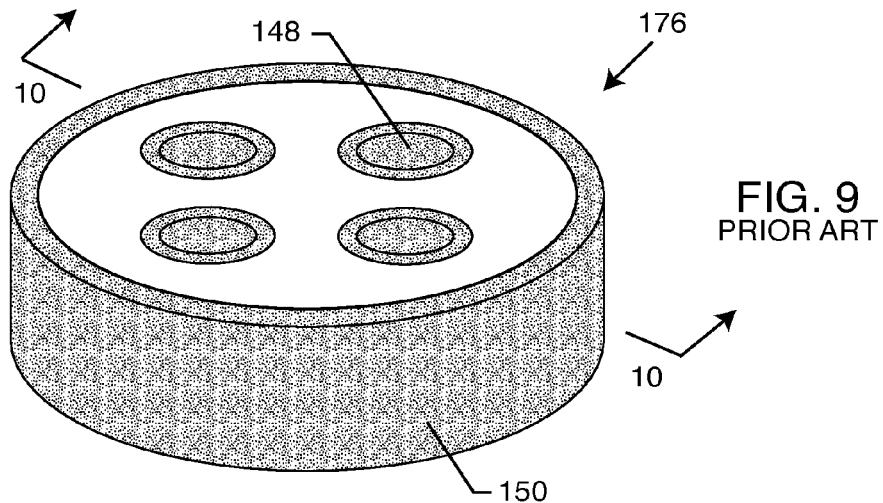
FIG. 9 is a perspective view of a quadpolar feedthrough capacitor.
Figure 10:
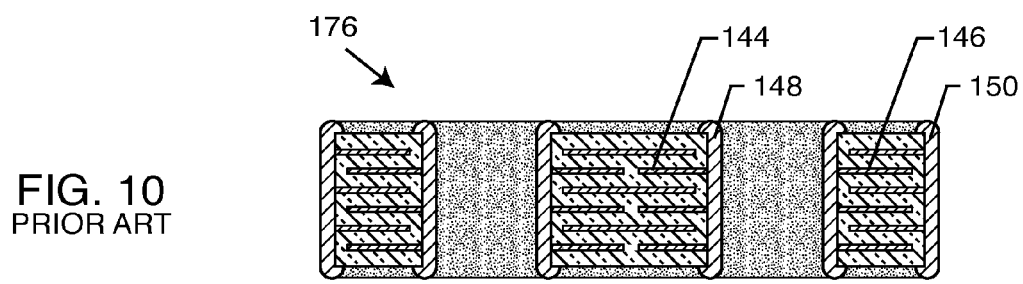
FIG. 10 is a cross-sectional view of the quadpolar feedthrough capacitor, taken along the line 10-10 of FIG. 9.
Figure 11:
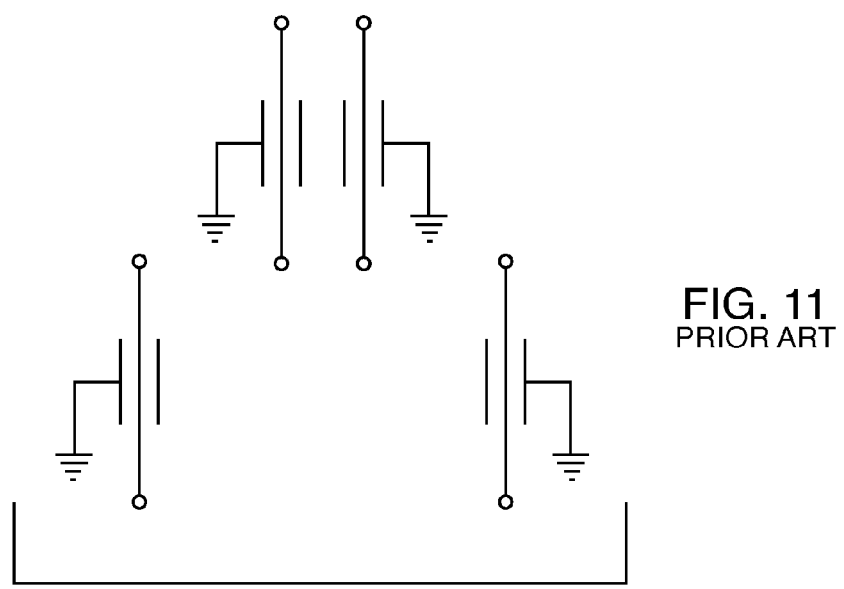
FIG. 11 is an electrical schematic diagram of the quadpolar feedthrough capacitor of FIGS. 9 and 10.
Figure 14:
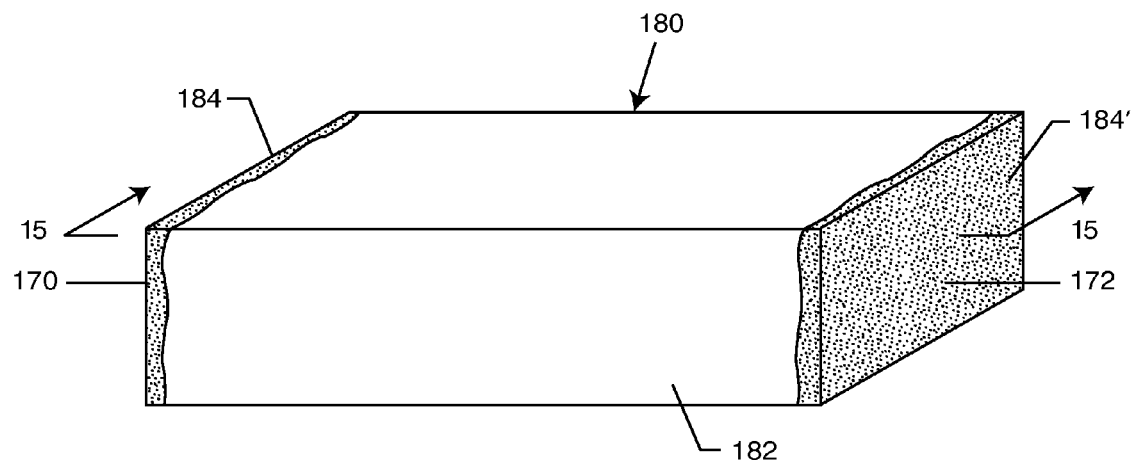
FIG. 14 is a perspective view of a monolithic ceramic capacitor (MLCC)
Figure 15:
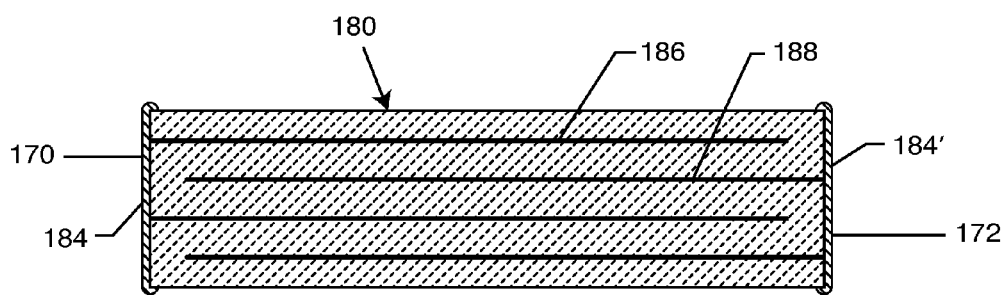
FIG. 15 is a cross-sectional view of the monolithic ceramic capacitor, taken along the line 15-15 of FIG. 14.
Figure 16:
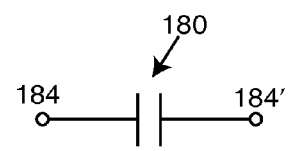
FIG. 16 is an electrical schematic diagram of an ideal MLCC capacitor as illustrated in FIGS. 14 and 15.
Figure 17:
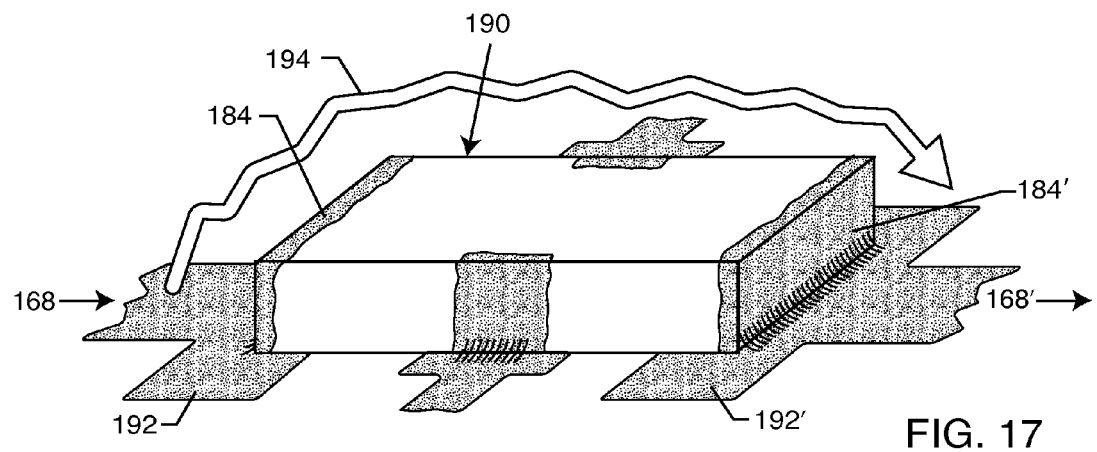
FIG. 17 is a perspective view of a prior art flat-through capacitor.
Figure 18:
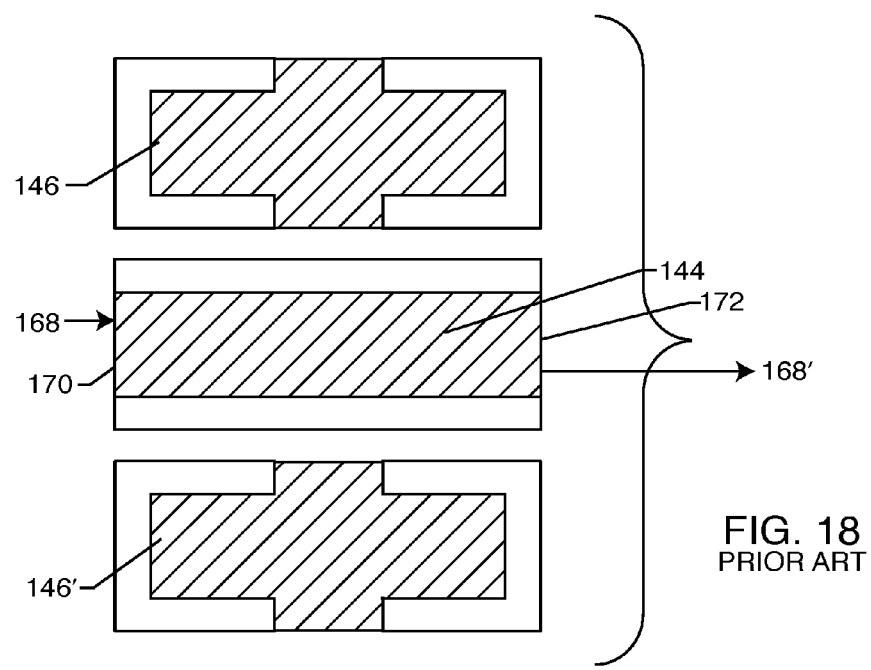
FIG. 18 illustrates the internal electrode array of the flat-through capacitor of FIG. 17.
Figure 19:
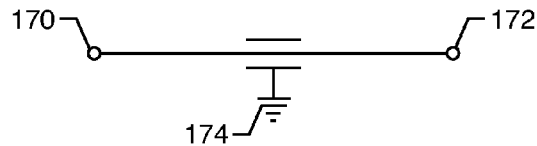
FIG. 19 is an electrical schematic drawing of the prior art flat-through capacitor of FIGS. 17 and 18.
Figure 20:
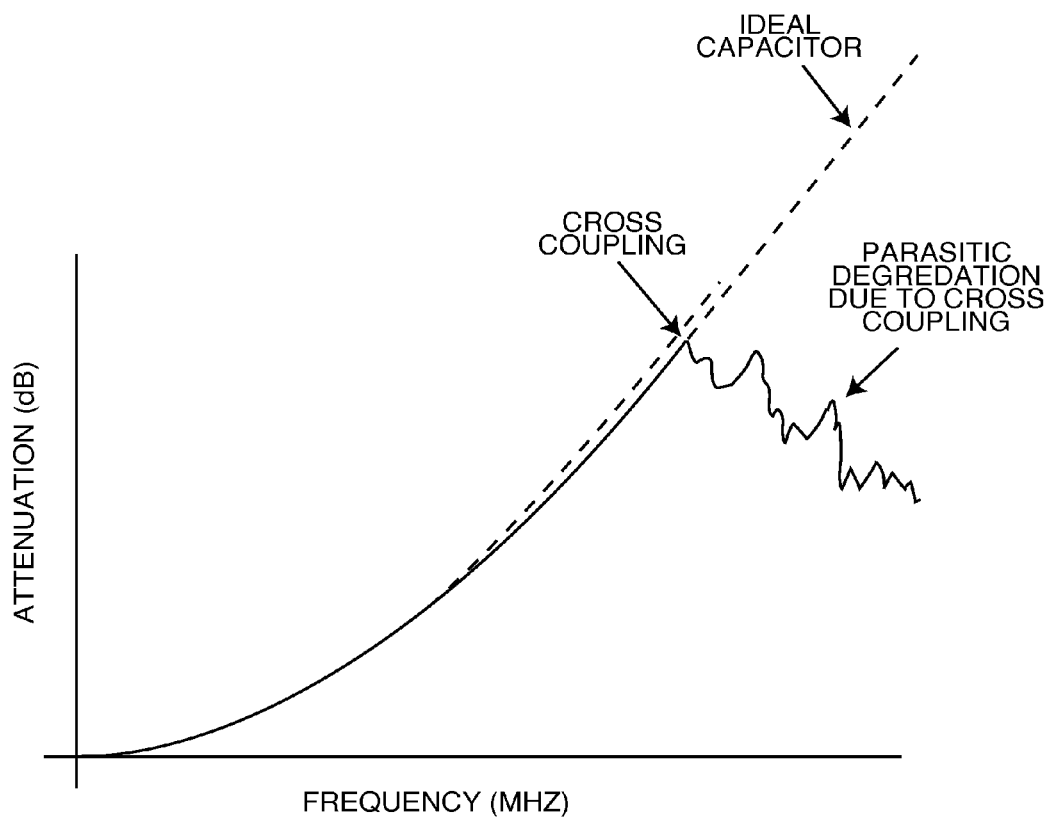
FIG. 20 is a graph illustrating the attenuation verses frequency response of the flat-through capacitor of FIGS. 17 and 18.

Since the leadwires 124a-124d are inside the hermetically sealed AIMD electromagnetic shield housing 104, these leadwires 124a-124d do not need to be biocompatible. In fact, they can be low cost tinned copper or the like. This is important for ease of assembly and to keep the cost down of the overall assembly. The filter capacitor component 210 of FIG. 21 has its outside diameter termination or metallization surface 150 (FIGS. 6 and 9) electrically and mechanically attached to the EMI shield 206. This provides a solid low impedance RF ground. Accordingly, the EMI shielded conduit assembly 196 becomes an extension of the overall electromagnetic shield of the AIMD electromagnetic shield housing 104. The EMI shielded conduit assembly 196 could also be formed from low cost conductive (shielded) heat-shrink tubing. The heat-shrink tubing would be heated to cause it to simultaneously be shrunk down over the four insulated leadwires 124a-124d, and at the same time be shrunk down around the outside diameter or perimeter of the ferrule 138 of the hermetic seal 198 to form the ground connection to the AIMD electromagnetic shield housing 104. It is very important that the overall coaxial or co-extensive EMI shield 206 be circumferentially and longitudinally nearly continuous and of very low inductance so that the EMI filter capacitor component 210 can provide proper attenuation at high frequencies. The support feet 204 can alternatively be non-conductive, in which case they are simply there to provide mechanical attachment and resistance to shock and vibration loads. Or, as shown, the support feet 204 can be conductive and connect to the ground circuit traces 212a and 212b. The ground circuit traces 212a and 212b are very useful for AIMD circuitry. For example, this low impedance ground can be used for connection of high voltage suppression arrays, such as diode arrays. As will be further illustrated, these ground circuit traces 212a and 212b are very useful to ground in or on an electronic circuit board, substrate or network. The ground circuit traces 212a and 212b are also very useful for combinations of bandstop filters, L-C trap filters, low pass filters, electronic filters, a short-to-housing switch network, and the like. They could also be used for reference grounding or grounding of telemetry circuits and the like. In summary, in addition to shielding of the leadwires, the EMI shield conduit also provides a low impedance circuit path for RF grounding of the remote EMI filter and/or other AIMD circuits.

Figure 22:
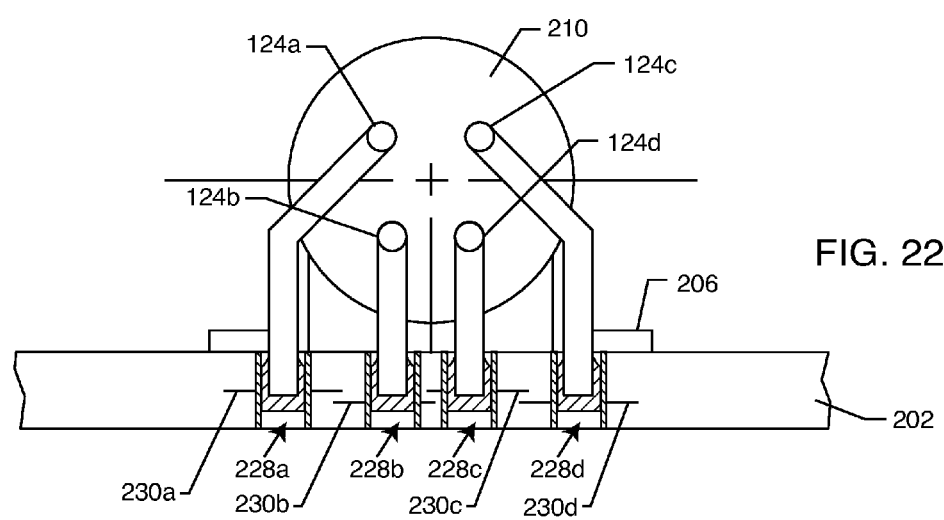
FIG. 22 is an end view of the EMI shielded conduit assembly taken generally from the line 22-22 of FIG. 21.

FIG. 22 is an end view taken generally from section 22-22 from FIG. 21. Shown are the end views of the leadwires 124a-124d as they exit the filter capacitor component 210.

One can also see the support feet 206 connected to the ground circuit traces 212a and 212b of the circuit board 202 (FIG. 21). In the case of a cardiac pacemaker, the circuit board 202 would also be known as the pacer hybrid board which contains various electronic modules, microelectronic chips, cardiac sense circuits and so on. Also shown are alternative via holes 228a-228d which connect to the leadwires 124a-124d. These can go to external or the interior circuit traces 230a-230d of the multilayer circuit board 202.

Figure 25:
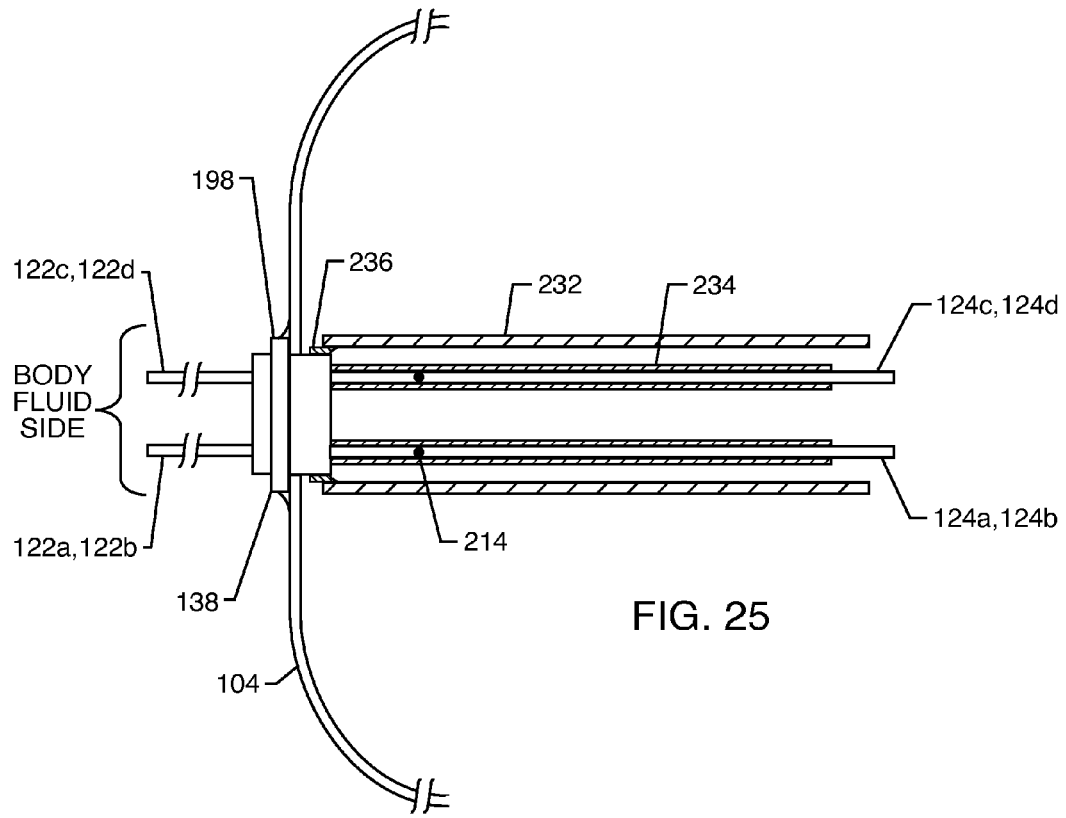
FIG. 25 is a sectional view similar to FIG. 21, except that the shielded conduit is replaced by a conductive heat-shrink tubing.

FIG. 25 is very similar to the left side of FIG. 21 except that the novel EMI shielded conduit assembly 196 has been replaced by a conductive heat-shrink tubing 232. Referring to FIG. 25, a non-conductive heat-shrink insulation tubing 234 is slipped down over the leadwires 124a-124d as shown. The insulation tubing 234 does not have to be heat-shrink tubing in this case. It could be a thin wall slip-on insulation tubing, such as Kapton or the like. Since the conductive ferrule 138 of the hermetic seal 198 is typically of titanium, it is prone to formation of oxides. These oxides can degrade electrical connections. This is not generally a problem when the ferrule 138 is laser welded into the conductive AIMD electromagnetic shield housing 104. This is because the laser weld burns through any oxides and forms a solid metallurgical joint. However, shrinking down the conductive heat-shrink tubing 232 directly onto an oxidized titanium ferrule would make for a very poor ground connection. Accordingly, there is a preparation surface 236 that is first deposited on the ferrule 138. This can be of conductive metal plating, a braze, a gold braze, or even a sputtering such as platinum or gold sputtering. This provides an oxide free surface to which the EMI shielded conduit assembly 196, which can be the conductive heat-shrink tubing 232, can both mechanically and electrically attach. The importance of an oxide free connection is thoroughly described in U.S. Pat. No. 6,765,779, the contents of which are incorporated herein by reference.

Figure 26:
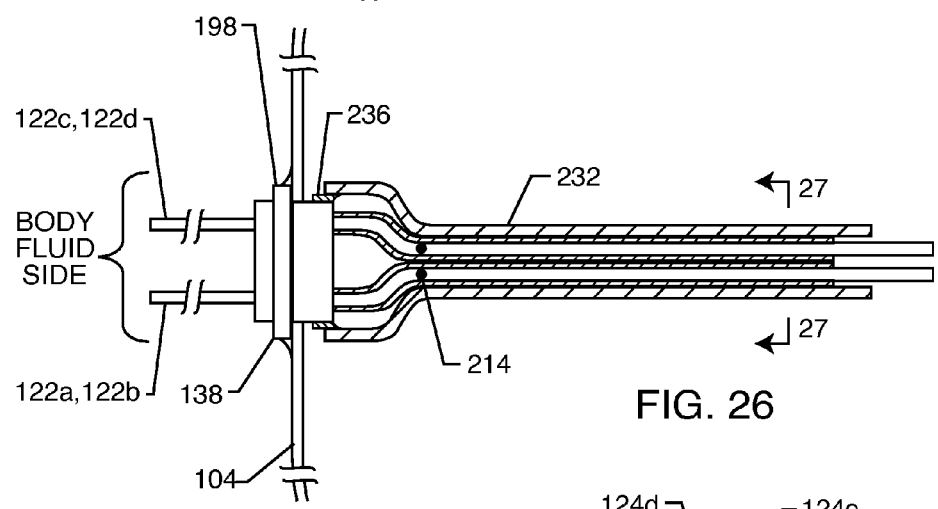
FIG. 26 illustrates the heat-shrink tubing shrunk around four leadwires.
Figure 27:
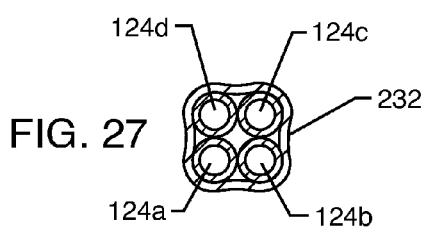
FIG. 27 is an end sectional view taken generally along the line 27-27 of FIG. 26, illustrating the four leadwires within the shrunk heat-shrink tubing.

FIG. 26 is the same view as FIG. 25 after heat has been applied to shrink the conductive heat-shrink tubing 232. FIG. 27 is an end view taken generally from section 27-27 from FIG. 26. It shows the end view of the four leadwires 124a-124d.

Figure 28:
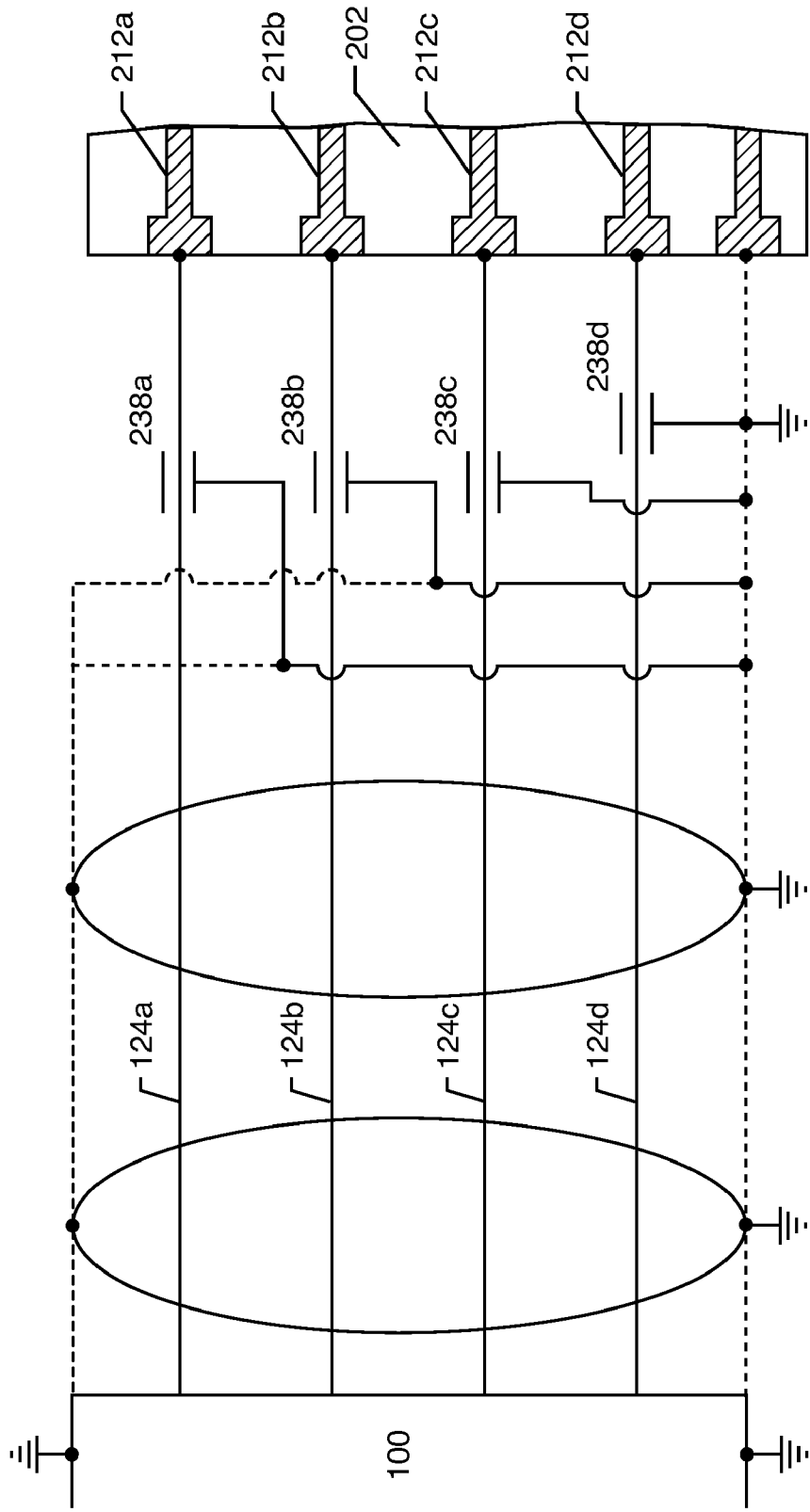
FIG. 28 is an electrical schematic diagram of the EMI shielded conduit assembly shown in FIGS. 21-27.

FIG. 28 is a functional schematic diagram of the novel shielded conduit remote filter as previously discussed in FIGS. 21 through 27. Referring to FIG. 28, there are four capacitors 238a-238d which are integral to the monolithic quadpolar feedthrough capacitor 176 illustrated in FIGS. 9-11 and 13. As previously described, the capacitors 238a-238d may be eliminated in certain AIMD designs where the AIMD internal unshielded leadwires or circuit traces are short in length compared to the wavelength of the EMI signals. In this case, the feedthrough capacitor would be eliminated and just the shielded conduit would be routed to the circuit board 202 as shown. This approach is particularly applicable to AIMDs that do not have sense circuits such as many implantable neurostimulators. AIMDs that do not have biologic sense circuits are inherently less sensitive to EMI. The leadwires 124a-124d illustrated in FIG. 28 are shown connected to the AIMD electronic circuit board, substrate or network 202 which can include a variety of electronic circuits including microchips. The purpose of the quadpolar feedthrough capacitor 176 is to provide a single element low pass filter to ground on each leadwire 124a-124d in order to protect the sensitive electronics on the circuit board 202 from EMI that can be coupled from the implanted leads 122a-122d. This is particularly important if the AIMD electronic circuit board, substrate or network 202 has biologic sensing circuits which is common in the prior art for cardiac pacemakers and ICDs.

Figure 29:
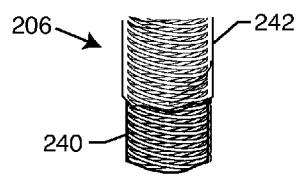
FIG. 29 is a fragmented perspective view of a particular type of EMI shield having a braid shielding.
Figure 30:
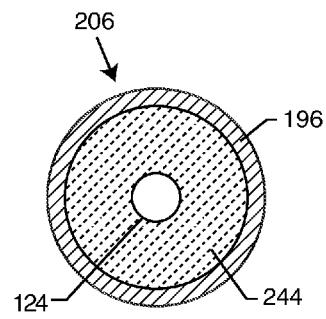
FIG. 30 is an end view of an EMI shield having an insulation material disposed between the leadwire and the EMI shield conduit.
Figure 31:
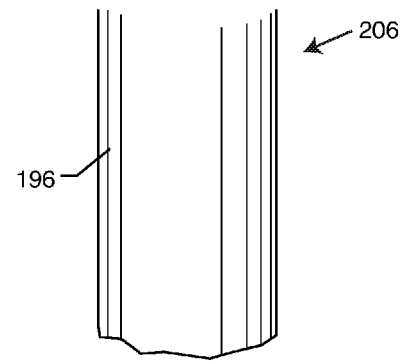
FIG. 31 is an elevational view of the solid copper EMI shield conduit of FIG. 30.

FIG. 29 illustrates a particular type of EMI shield 206 called braid shielding. In this case, a set of fine wires 240 are woven back and forth underneath an insulated surface 242 (transparent) as shown. FIGS. 30 and 31 show that the novel EMI shielded conduit assembly 196 can be of solid material such as soft copper. FIG. 30 is an end view illustrating the solid tubing of the EMI shielded conduit assembly 196 and the unipolar leadwire 124 disposed within an insulative material 244. The insulative or dielectric material 244 is used as shown.

Figure 32:
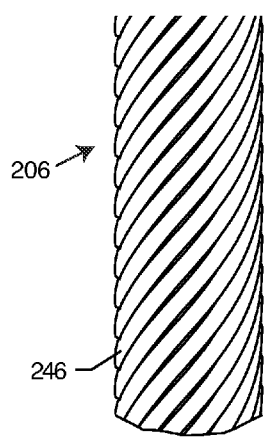
FIG. 32 is a fragmented perspective view of a coaxial wound wire forming an EMI shield conduit.
Figure 33:
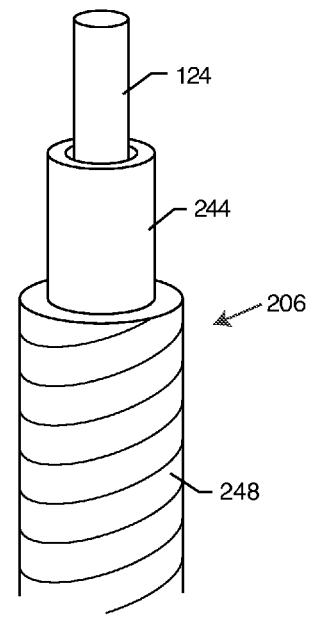
FIG. 33 is a perspective view of an alternative EMI shield conduit having a conductive foil wound around insulation material disposed around the leadwire.
Figure 34:
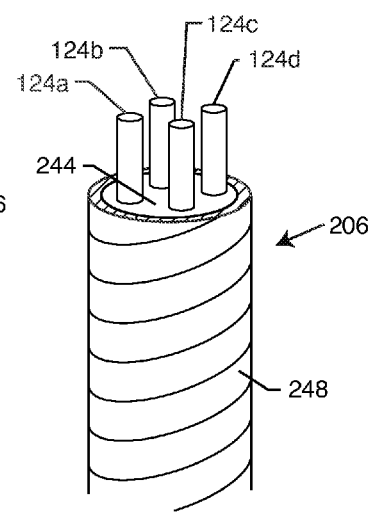
FIG. 34 is a perspective view similar to FIG. 33, further illustrating multiple leadwires disposed within the insulation material surrounded by the conductive foil.

FIG. 32 illustrates the use of a coaxial wound wire 246 to form the EMI shield 206. FIG. 33 shows the use of a metallic thin conductive foil, or foils, 248 which can be formed, wound, or woven around the insulative material 244 to form the EMI shield 206 around the leadwire 124. FIG. 34 is very similar to FIG. 30, but shows four leadwires 124a-124d.

Figure 35:
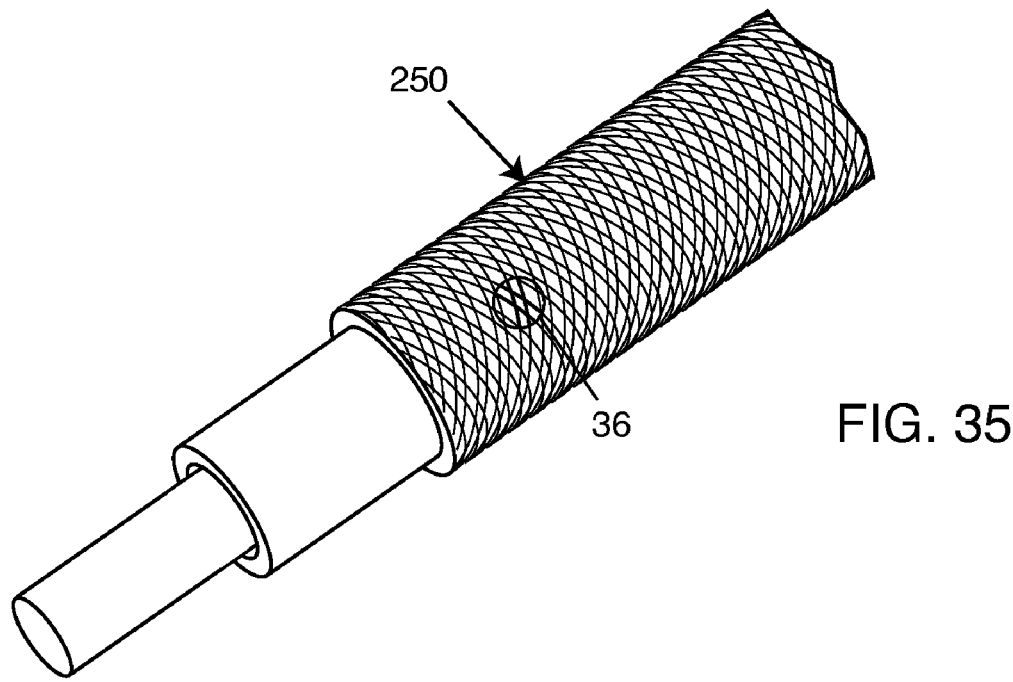
FIG. 35 is fragmented perspective view of an EMI shielded conduit formed from a shielded mesh interwoven with conductive strands.
Figure 36:
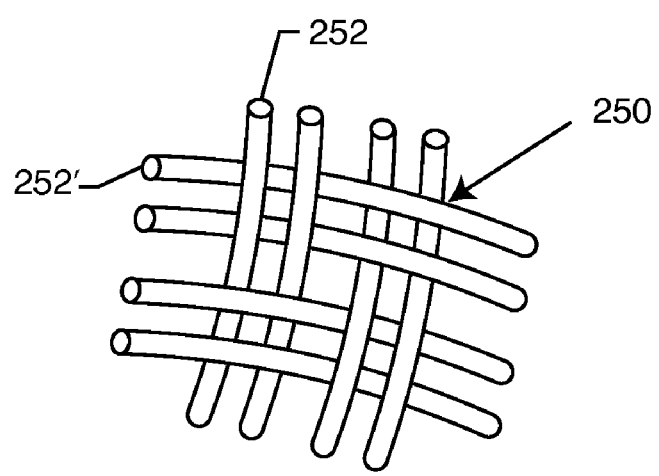
FIG. 36 is an enlarged view of the shielded mesh interwoven with the conductive strands, taken about the area designated by reference number 36 in FIG. 35.
Figure 76:
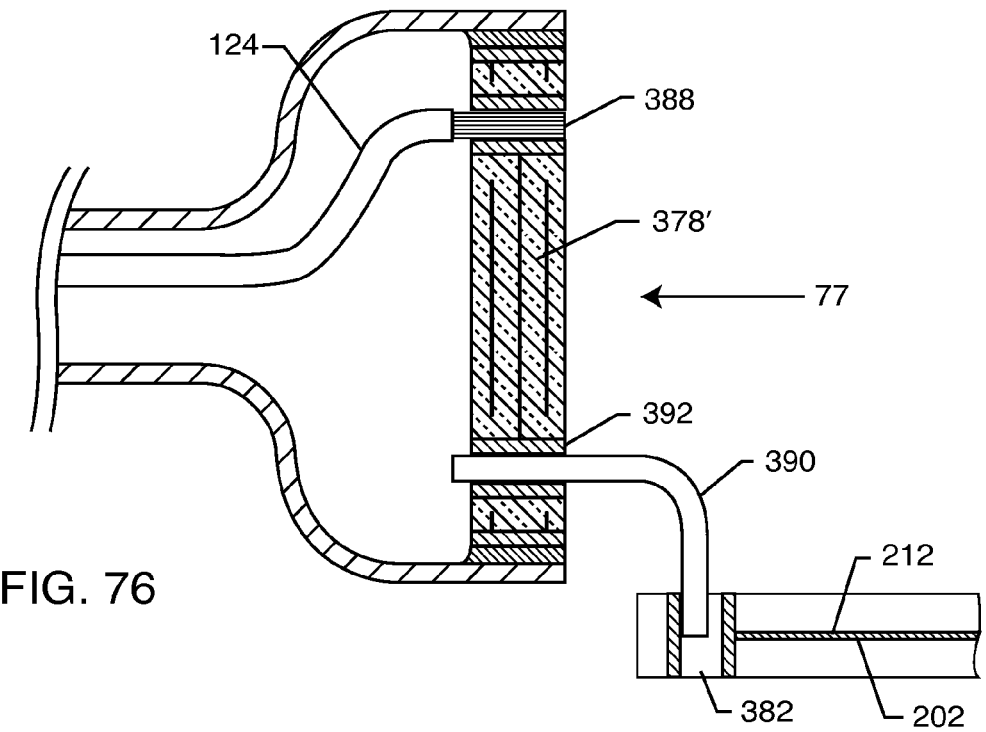
FIG. 76 is a schematic illustrating an alternative embodiment of a flat-through capacitor electrically and mechanically connected directly to the inside of a surface of the cover assembly.

FIG. 35 illustrates a shielded mesh 250 interwoven with a set of conductive strands 252 (FIG. 76). FIG. 36 is an enlarged view of area 36 in FIG. 35 showing how the conductive strands 252, 252' are woven. It is very important that the weaving be fairly tight so stray high frequency EMI cannot penetrate the shield and that the inductance of the shield conduit be relatively low.

Figure 37:
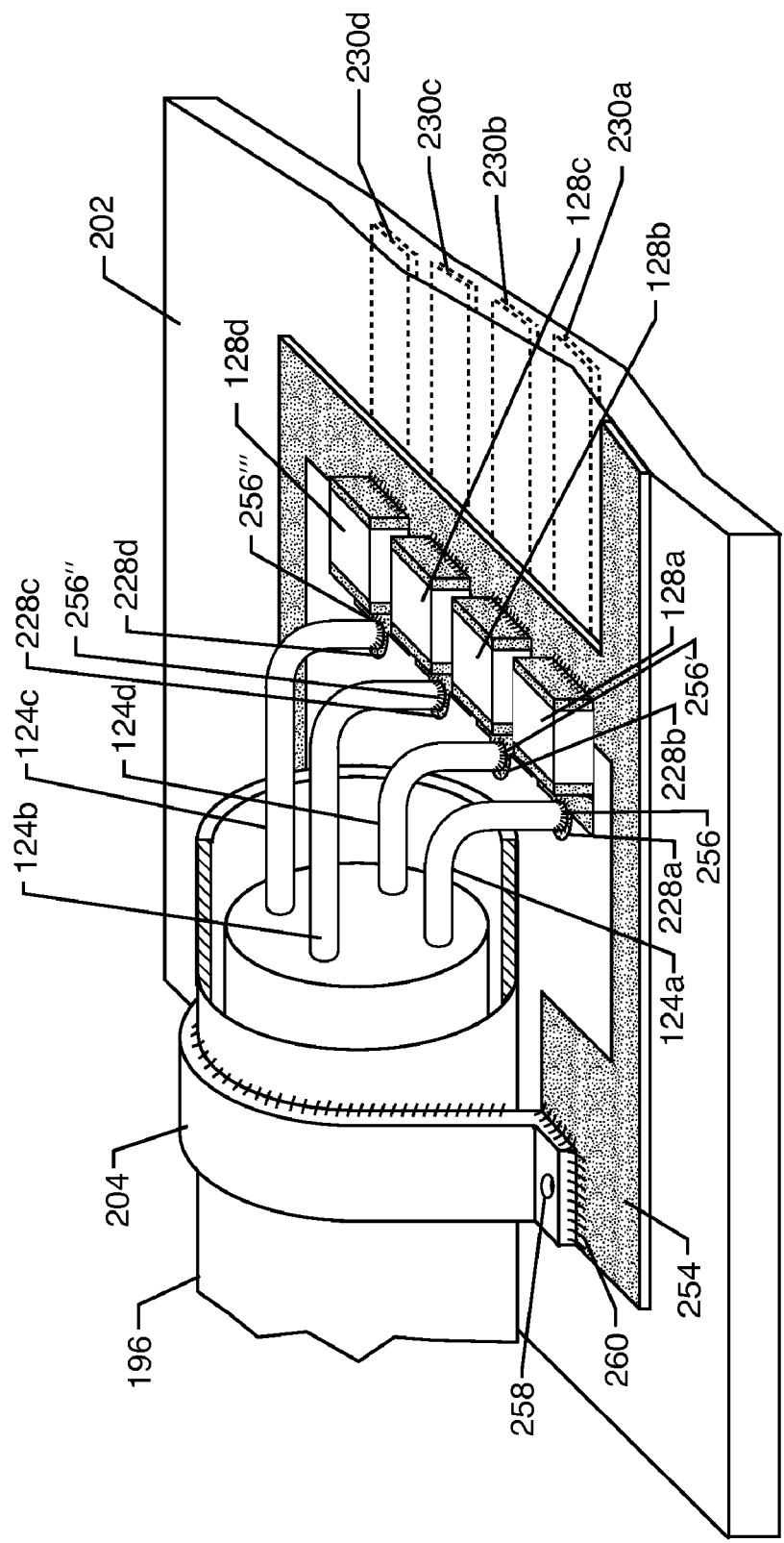
FIG. 37 is a fragmented perspective view of an EMI shield conduit mounted to a circuit board having multiple MLCC chip capacitors.

FIG. 37 shows an alternative embodiment of the EMI shielded conduit assembly 196 that was previously shown in FIG. 21. In this case, the filter capacitor component 210 that was shown in FIG. 21 could still be used, but it would be mounted on the circuit board 202 in place of the four MLCC chip capacitors 128a-128d shown in FIG. 37. The filter capacitor component 210 would ideally be mounted face down on the circuit board 202 with its outside diameter ground metallization 150 (FIG. 9) electrically attached to a surrounding ground plane 254 which is also connected to the proximal end of the EMI shielded conduit assembly 196. Referring once again to FIG. 37, one can see that in this embodiment the leadwires 124a-124d are routed within the overall EMI shielded conduit assembly 196 to the left hand side of the prior art MLCC chip capacitors 128a-128d. The conductive support foot assembly 204 is shown electrically and mechanically connected to a ground plane 254. This ground plane 254 is desirably wide and continuous so it will form an effective low impedance high frequency equipotential surface. The right hand side of the prior art MLCC chip capacitors 128a-128d are electrically connected to this ground plane 254. Referring once again to FIG. 37, one can see that the ground plane circuit trace 254 is electrically connected to the EMI shielded conduit assembly 196. It is very important that this circuit path be very low in impedance. That is, it is important that at high frequency, the surface of the ground plane 254 be held at approximately the same potential as the overall AIMD electromagnetic shield housing 104. To accomplish this, the EMI shielded conduit assembly 196 must be of relatively large cross-sectional area. This can be imagined if one were to slit it and then roll it out flat and look at it from edge view. This forms, in the art, an equivalent RF grounding strap. In summary, the novel EMI shielded conduit assembly 196 forms two very important purposes: (1) it effectively shields and prevents EMI re-radiation inside the AIMD housing from the leadwires 124a-124d; and (2) it provides a very low impedance connection back to the AIMD electromagnetic shield housing 104 to the circuit board ground path 254. The leadwires 124a-124d are electrically connected through the via holes 228a-228d using an electrical connective material 256-256''', such as solder or thermal-setting conductive adhesive. The MLCC capacitors 128a-128d are also electrically connected to the ground plane 254 through electrical connections 256-256'''. The shielded support foot 204 is in the form of a ring and is electrically connected either through holes 258 or by way of an outside electrical connection 260 as shown. It is important that the portion of the leadwires 124a-124d that exits the EMI shielded conduit assembly 196 be kept quite short so they will not become an effective re-radiating antenna or stray capacitance which would allow EMI to couple to sensitive circuits such as pacemaker sense circuits. The assemblies shown in FIG. 37 are all mounted to the AIMD electronic circuit board, substrate or network 202 which supports other surface mounted or imbedded AIMD electronic components (not shown). The via holes 228a-228d connect to internal circuit traces 230a-230d as shown.

Figure 38:
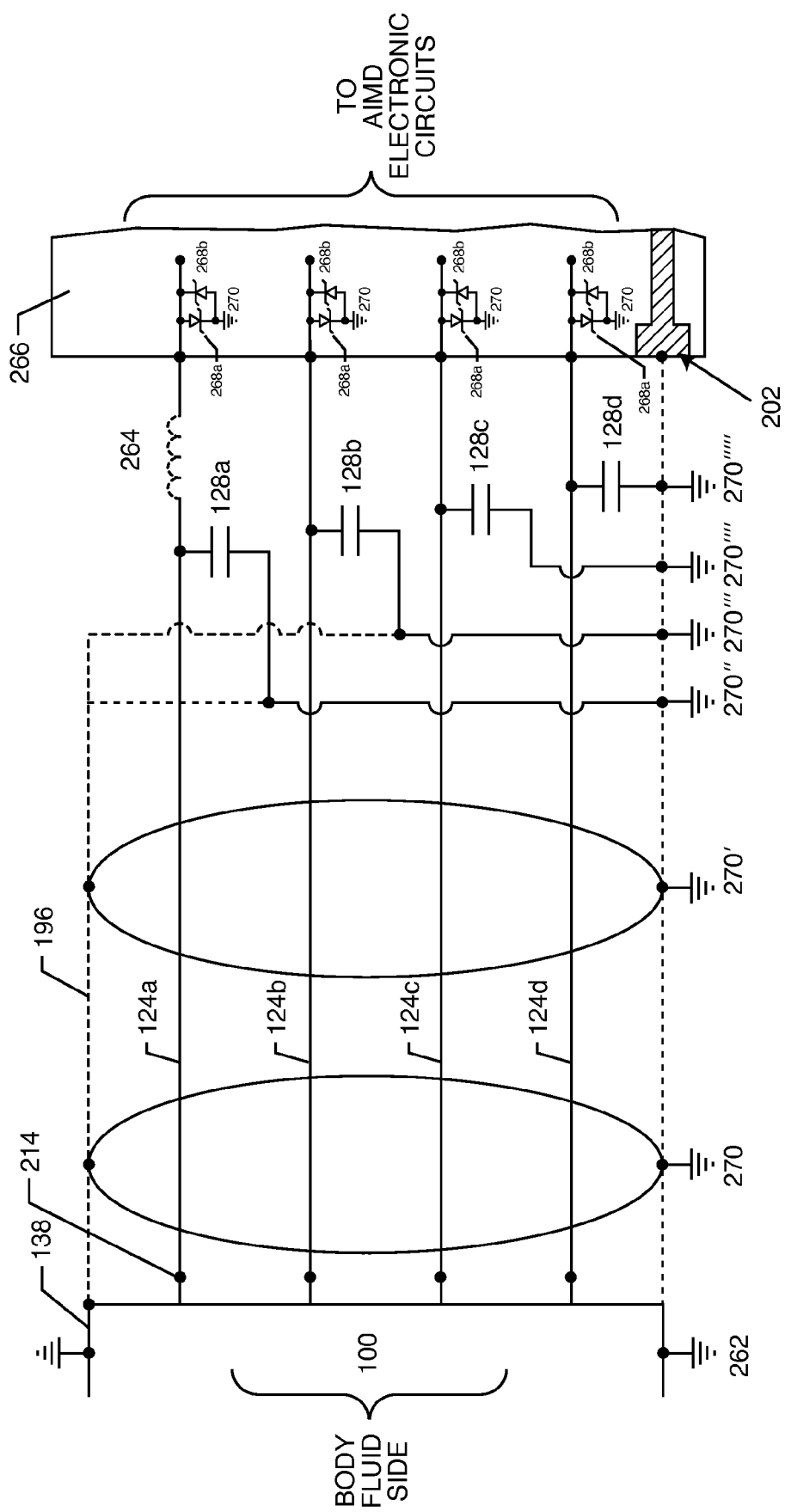
FIG. 38 is an electrical schematic diagram of the remote MLCC mounted filter illustrated in FIG. 37.

FIG. 38 is a schematic diagram of the remote MLCC chip capacitor 128 as illustrated in FIG. 37. Referring to FIG. 38, one can see on the left side the hermetic terminal 100. Its ferrule 138 is coupled to a ground 262, which is coupled to the overall AIMD electromagnetic shield housing 104. The EMI shielded conduit assembly 196 is also shown electrically grounded to the hermetic terminal 100. It is important that this be a low impedance oxide free connection. This connection from the EMI shielded conduit assembly 196 can be accomplished by a clamp (not shown) which binds the conductive EMI shielded conduit assembly 196 to the outside diameter of the ferrule 138. As previously described, the titanium ferrule 138 of the hermetic terminal 100 would be pretreated with plating, gold braze, or the like to prevent oxidation. An alternative would be to solder, braze or attach with conductive adhesives the EMI shielded conduit assembly 196 to the ferrule gold braze of the hermetic seal assembly (ref. the methods described in U.S. Pat. No. 6,765,779, the contents of which are incorporated herein). The remote EMI filter (or optionally an unfiltered circuit board), in this case, consists of the four MLCC chip capacitors 128a-128d as shown. These also form in the art what is known as a quadpolar single element low pass filter. An optional inductor element 264 has been shown in the leadwire 124a. It will be obvious to those skilled in the art that additional capacitors and inductors can be added to form L, PI, T, LL or "n" element low pass filters in any or all leadwires 124a-124d. Referring once again to FIG. 38, one can see that the low pass filter elements are also closely coupled to a high voltage suppression array 266. The high voltage suppression array 266 can consist of back-to-back diodes 268a and 268b as shown, zener diodes, Transorbs®, and the like. It is important that the high voltage suppression diodes have a low impedance connection to a circuit ground 270 so they can be fast acting. This is important to protect against external high voltage events such as electrostatic discharge or automatic external defibrillation (AED) events. An important feature of the EMI shielded conduit assembly 196 is that it provides the required low impedance circuit path to ground. Referring once again to FIG. 38, one can see that the MLCC capacitors 128a-128d are all connected to the conduit circuit ground 270 and in a preferred embodiment, the high voltage suppression array 266 is also connected to the same low impedance circuit ground 270 as shown.

Figure 39:
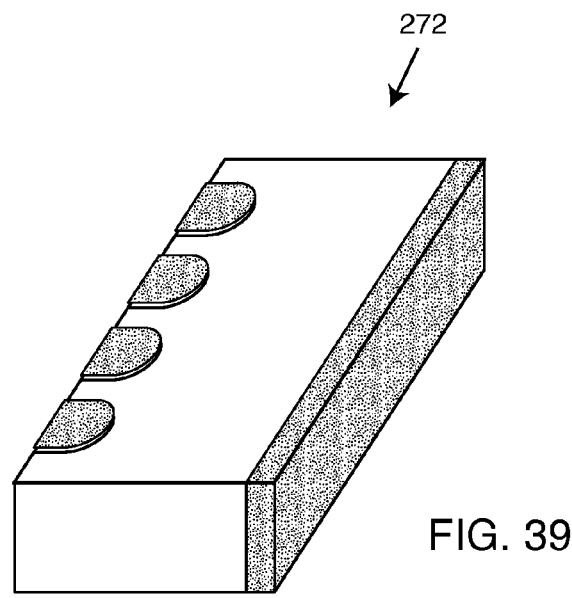
FIG. 39 is a perspective view of a multi-element chip capacitor monolithic array that may be used in place of the four separate MLCC capacitors shown in FIG. 37.
Figure 40:
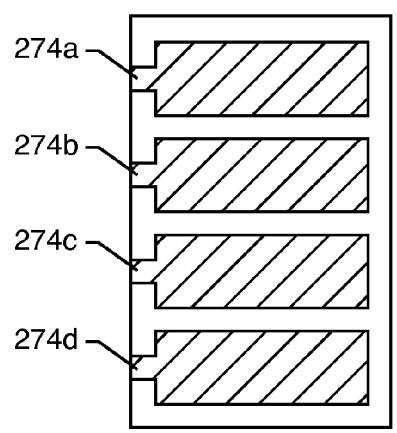
FIG. 40 shows the internal active electrodes (AE) of the multi-element chip capacitor monolithic array of FIG. 39.
Figure 41:
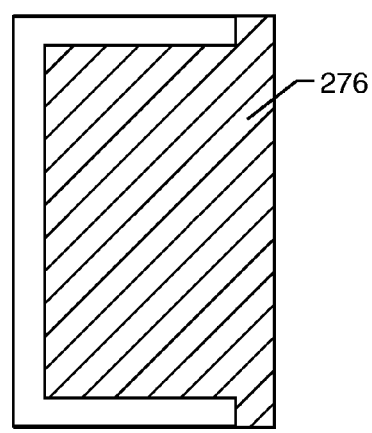
FIG. 41 illustrates an internal ground electrode (GE) of the multi-element chip capacitor monolithic array of FIG. 39.

FIG. 39 is generally taken from section 39-39 in FIG. 37. Shown is a multi-element chip capacitor monolithic array 272 which is better understood by referring to an internal active electrode 274a-274d and an internal ground electrode 276 in FIGS. 40 and 41. The capacitor array 272 of FIG. 39 is very similar to prior art MLCC chip capacitors, but the single quadpolar chip is more volumetrically efficient. This is accomplished by placing all four chip capacitors in a single monolithic package. The multi-element chip capacitor monolithic array 272 shown in FIG. 39 can also be replaced by the flat-through capacitor 190 as shown in FIGS. 17 through 20, an active electronic filter, or even an X2Y attenuator. An X2Y attenuator is generally a specially configured ceramic chip capacitor with unique internal electrode geometry. Examples of some X2Y attenuators can be found in U.S. Pat. No. 5,909, 350; U.S. Pat. No. 6,018,448; U.S. Pat. No. 6,097,581; U.S. Pat. No. 6,157,528; U.S. Pat. No. 6,282,074; U.S. Pat. No. 6,388,856; U.S. Pat. No. 6,373,673; WO2005/1015719; US2004/0027771; US2004/0032304; U.S. Pat. No. 6,469, 595; U.S. Pat. No. 6,498,710; U.S. Pat. No. 6,509,807; U.S. Pat. No. 6,522,516; U.S. Pat. No. 6,549,389; U.S. Pat. No. 6,563,688; U.S. Pat. No. 6,580,595; U.S. Pat. No. 6,594,128; U.S. Pat. No. 6,603,646; U.S. Pat. No. 6,606,011; U.S. Pat. No. 6,636,406; U.S. Pat. No. 6,650,525; U.S. Pat. No. 6,687, 108; U.S. Pat. No. 6,738,249; and U.S. Pat. No. 6,806,806, the contents of which are all incorporated herein.

Figure 42:
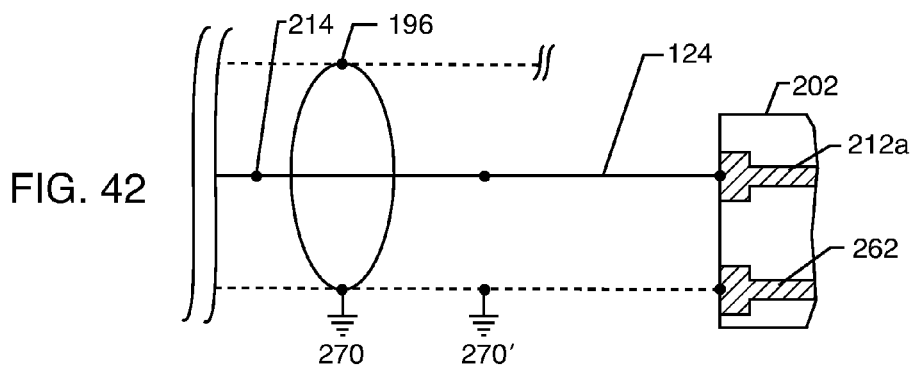
FIG. 42 is a circuit diagram illustrating an embodiment wherein the EMI shield conduit has no low pass filter.

FIGS. 42 to 53 show various circuit schematic combinations which illustrate a number of ways that the novel EMI shielded conduit assembly 196 may be configured with remote circuit boards/substrates 202, low pass filters LP, BSFs, L-C traps, active electronic filters, high voltage suppression (circuit protection) arrays, and electronic short-to-housing switch networks. Reference is made to U.S. patent application Ser. No. 12/489,921 for examples of how such electronic components can be advantageously used in connection with the present invention. FIGS. 42 to 52 are all illustrated for one leadwire 124 or circuit path of the AIMD only. It will be obvious to those skilled in the art the AIMD can have any number of circuit leadwires 124 that are routed through one or more hermetic seal 198 terminal pins 200 to the implanted leads 122 to which the present invention applies. FIG. 42 illustrates the case with no passive low pass filter where the circuit traces $212_a$ to $212_n$ are short relative to the EMI frequency wavelength and/or the AIMD is not very sensitive to EMI.

Figure 43:
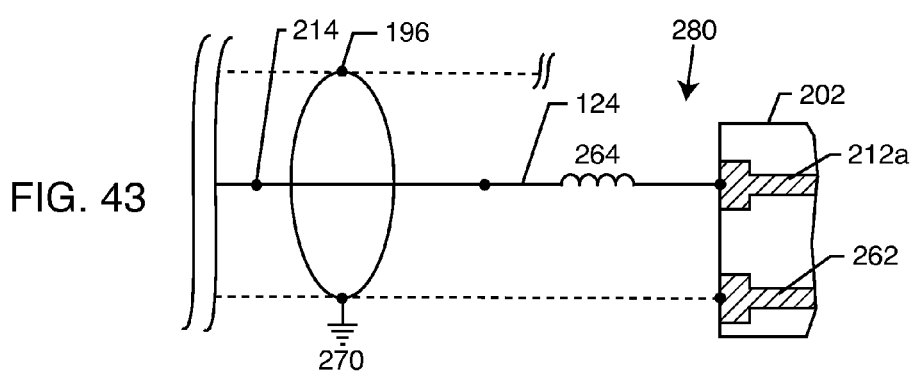
FIG. 43 is a circuit diagram illustrating a single element inductor low pass filter.
Figure 44:
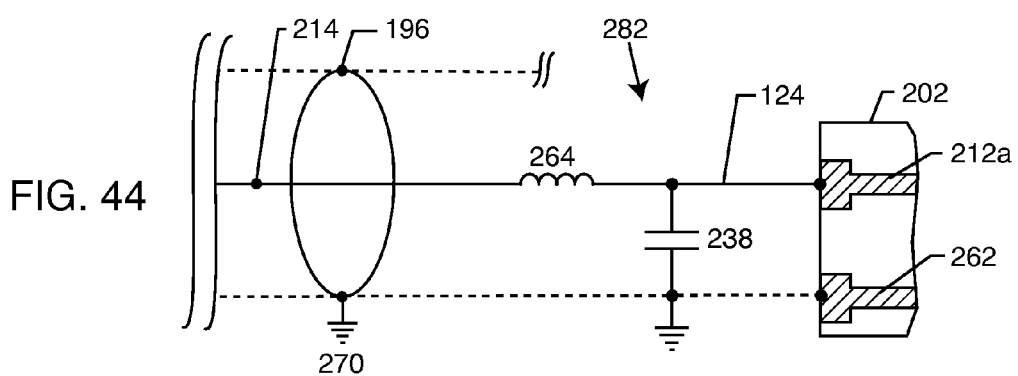
FIG. 44 is a circuit diagram illustrating an L section low pass filter including an inductor and a capacitor.
Figure 45:
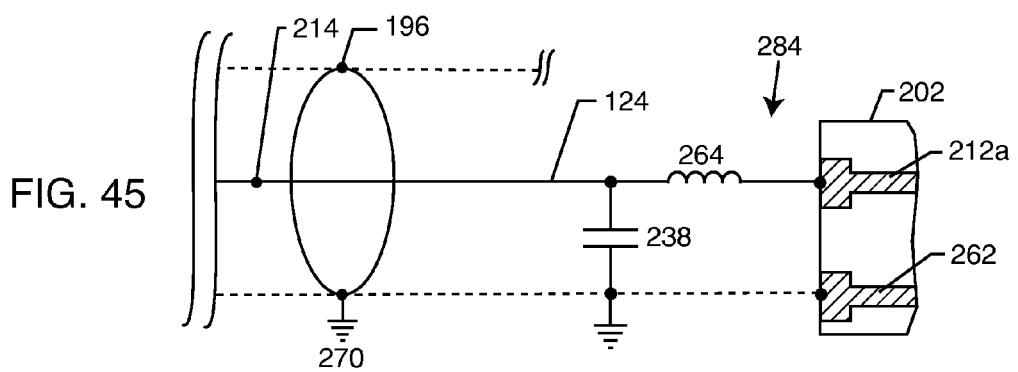
FIG. 45 is a circuit diagram illustrating a reverse low pass filter where the capacitor points toward the hermetic seal.

FIG. 43 illustrates an inductor 264 single element low pass filter 280. FIG. 44 illustrates what is known in the prior art as an "L" section low pass filter 282 consisting of the inductor 264 and the capacitor 238. In this case, the inductor 264 points toward the hermetic seal (body fluid side). FIG. 45 is a reverse "L" low pass filter 284 where the capacitor 238 points toward the hermetic seal (body fluid side). FIG. 46 is known in the art as a "T" filter 286. FIG. 47 is known as a PI filter 288. FIG. 48 generally shows an n-element low pass filter 290. Either the inductor (264a as shown) or the capacitor 238a can be the first component on the hermetic seal (body fluid side).

FIG. 49 illustrates a bandstop filter (BSF) 292 in series with the leadwire 124 consisting of the inductor 264 and the capacitor 238 in parallel (there can also be a resistive element, which is not shown). Refer to U.S. Pat. No. 7,363,090 and U.S. Publication 2006/0247684, which are herein incorporated by reference, for a full explanation of BSF characteristics, resonance equations, bandwidth and impedance vs. frequency curves. Also included in the references is the importance of controlling BSF quality factor (Q) and bandwidth.

Figure 50:
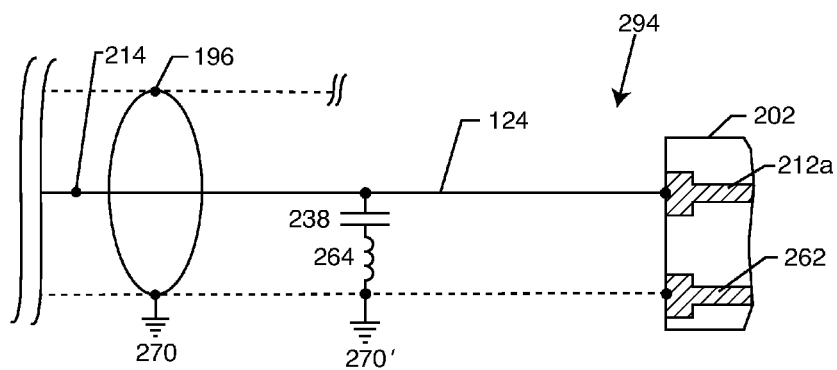
FIG. 50 is a circuit diagram illustrating an L-C trap filter.

FIG. 50 illustrates an L-C trap filter 294. The L-C trap filter 294 connects from the leadwire 124 to the low impedance circuit ground 262 and consists of the capacitor 238 in series with the inductor 264 (there can also be a resistive element, which is not shown). Refer to U.S. Pat. No. 6,424,234, which is herein incorporated by reference, for a full explanation of L-C trap filter characteristics, resonance equations, bandwidth and impedance vs. frequency curves.

Figure 51:
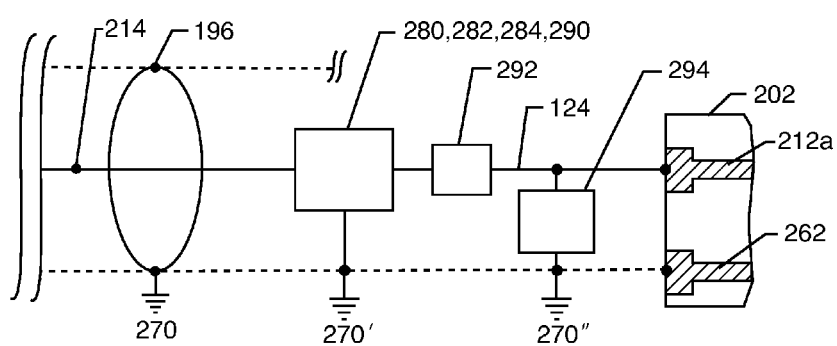
FIG. 51 is a circuit diagram illustrating the combination of a low pass filter, a bandstop filter and an L-C trap filter.
Figure 52:
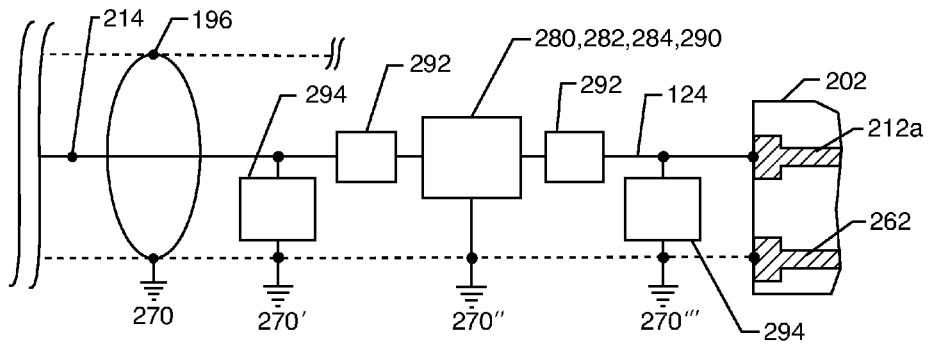
FIG. 52 is a circuit diagram illustrating the combination of an L-C trap filter, a bandstop filter, an LP filter, a second bandstop filter and a second L-C trap filter.

FIGS. 51 and 52 illustrate that any of the low pass filters 280-284 and 290 can be wired in various combinations with the BSF filter 292 and/or the L-C trap filter 294 to form any passive filter that one wishes to realize.

Figure 53:
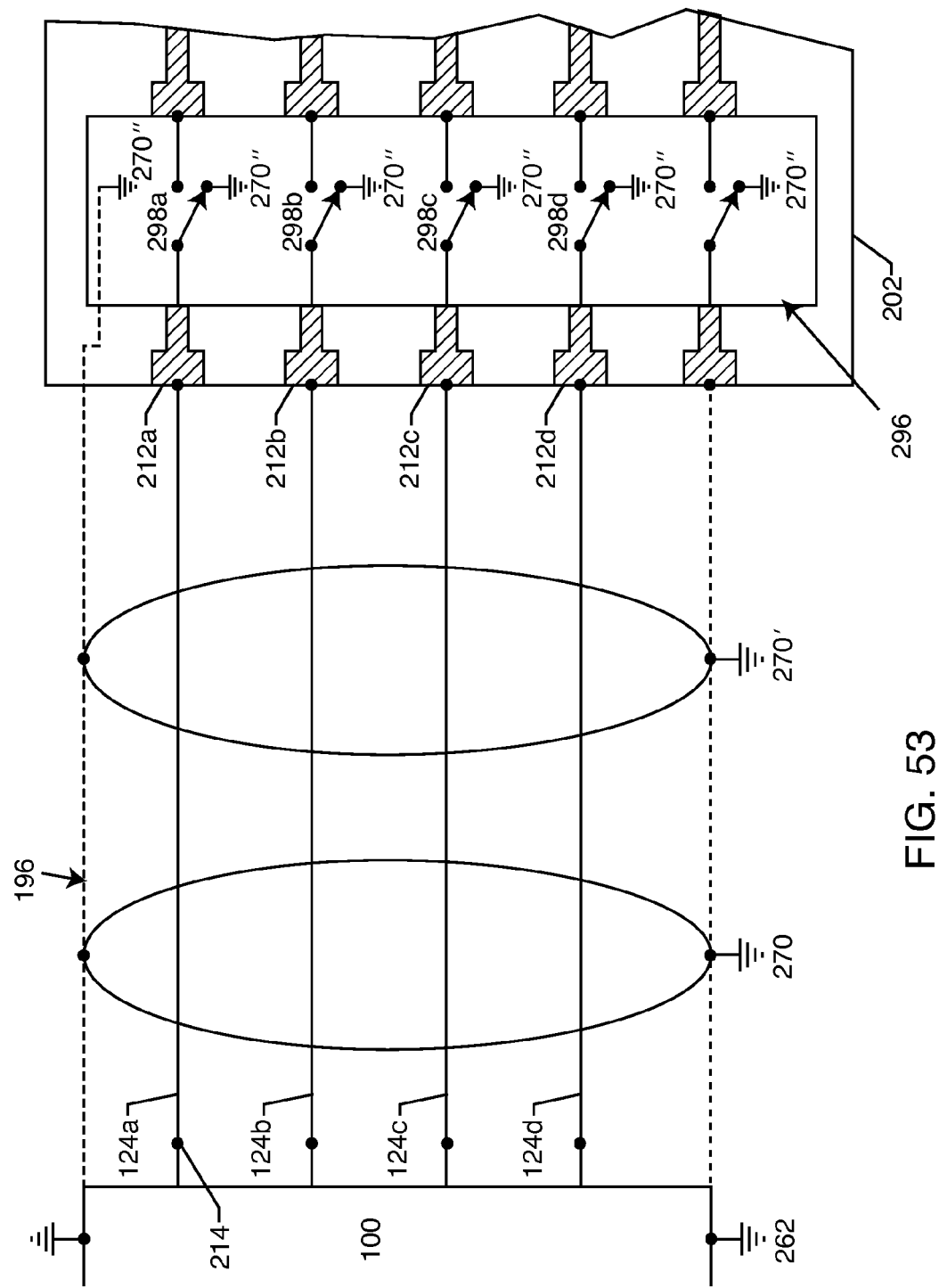
FIG. 53 is a circuit diagram illustrating an automatic or programmable electronic short-to-housing switch network chip or electronic switch array.

In all of these circuits, the EMI shielded conduit assembly 196 forms the circuit ground 262 for the circuit board 202, the low pass filter 280-284 and 290, the L-C trap filter 294, the high voltage suppression array 266, a telemetry circuit, a general circuit board/substrate reference (this is particularly important when the AIMD housing becomes a pacing or sensing electrode), an active electronic filter circuit, and/or the RF low impedance ground for a short-to-housing switch network. As shown in FIGS. 51 and 52, combining any of the low pass filters 280-284 and 290 with the bandstop filters 292 and/or the L-C trap filters 294 can be very effective for MRI environments. Trap filters can be used to dissipate maximal energy away from the implanted leads to the AIMD electromagnetic shield housing 104. FIG. 53 illustrates an automatic or programmable electronic short-to-housing switch network chip or electronic switch array which can be a dedicated chip or a portion of the hybrid or microchip of the AIMD which forms many other functions. Electronic switches which form a short to the AIMD housing are more fully described in U.S. patent application Ser. No. 12/489,921. In a preferred embodiment, the electronic switch array 296 of FIG. 53 would have its switches normally closed (in FIG. 53, they are shown in the open position). This allows the AIMD to operate normally, sense biologic signals, and delivery needed therapy such as pacing pulses to body tissue. The switches are shown in FIG. 53 in the open position wherein the wipers of the switches 298a-298d are connected toward the hermetic terminal 100 (body fluid) side of the leadwires 124a-124d. When the switches 298a-298d are switched open as shown, the wipers are connected to the circuit ground 270″ which is provided by the novel EMI shielded conduit assembly 196. At the same time, the leadwires 124a-124d are disconnected from other AIMD electronic circuits. In the open position as shown, the wiper connection forms a low impedance RF ground which shorts out each one of the leadwires 124a-124d effectively through the EMI shielded conduit assembly 196 to the AIMD electromagnetic shield housing 104. The switches 298a-298d can have mechanical wipers, however, in the preferred embodiment, these would be any type of electronic switches such as involving P-N junctions well known in the prior art.

The switches would be controlled (programmed) through AIMD programming and telemetry. With a field sensor, the switches could also be configured to switch automatically, say in the presence of a powerful magnetic field such as the static $B_0$ field of an MRI scanner. For a patient who was not dependant on their AIMD as a life saving device (most neurostimulator patients, and non-pacemaker dependant pacemaker patients), the switch array ESA would be used when the AIMD and/or its implanted leads are exposed to powerful electromagnetic fields, such as those produced by a clinical MRI scanner. Through AIMD telemetry, the electronic switch array is easily programmed into its MR Conditional Mode prior to the MRI scan. This mode switches the switches 298a-298d in the electronic switch array to the open (shorted position) as shown in FIG. 53. In a preferred MRI Conditional mode, the AIMD could also be programmed into an quiescent mode wherein it was not trying to sense biologic signals or deliver therapeutic pulses.

During the MRI (or other field exposure), the position of the switches 298a-298d shown in FIG. 53 accomplishes two very important things. The first is that the sensitive electronic circuitry (not shown) of the AIMD is disconnected and therefore becomes highly resistant to being influenced by EMI from the MRI scanner (or other high energy EMI source). The second major advantage is the shorting of the leadwires 124 to the low impedance EMI shielded conduit (circuit ground). This will pull unwanted induced RF energy out of the implanted leadwires 124 and divert said energy to the large surface area of the AIMD housing. This will greatly help to reduce implanted distal electrode heating at the points of tissue interface. By dissipating the induced MRI RF energy over the relatively large surface area of the AIMD electromagnetic shield housing 104, only a few degrees of harmless thermal energy will occur. This is in contrast to 20 or 30 degrees (or more) of possible temperature rise at the distal electrodes of the elongated implanted leadwires 124 without these features.

Another advantage of the electronic switch array ESA configuration illustrated in FIG. 53 is that the induced RF MRI energy that is picked up by the implanted leads 122 is diverted to the AIMD electromagnetic shield housing 104 which is usually not implanted in an area of the human body that is as sensitive to thermal injury. For example, for a cardiac pacemaker, a spinal cord stimulator or a deep brain stimulator, it is much better to have a few degrees of temperature rise in a pectoral muscle pocket than to have a temperature rise in the myocardium, the spinal cord or the brain. In summary, in FIG. 53, the novel EMI shielded conduit assembly 196 works in conjunction with the electronic switch array 296. When the switches 298a-298d are opened into the shorted position illustrated, high RF currents may flow through leadwires 124a-124d as the RF energy flows to the AIMD electromagnetic shield housing 104. It is important that these high RF currents be contained within the EMI shield or re-radiation or cross coupling to sensitive AIMD circuits could occur. In addition, it is an important feature that the novel EMI shielded conduits form a very low impedance short from the switch array to the AIMD electromagnetic shield housing 104. This is very important to both pull maximum unwanted RF energy from the implanted leads 122 and to form a true RF ground so that RF voltages will not become excessive on AIMD internal circuit traces where they could couple to and interfere with AIMD electronics.

Figure 54:
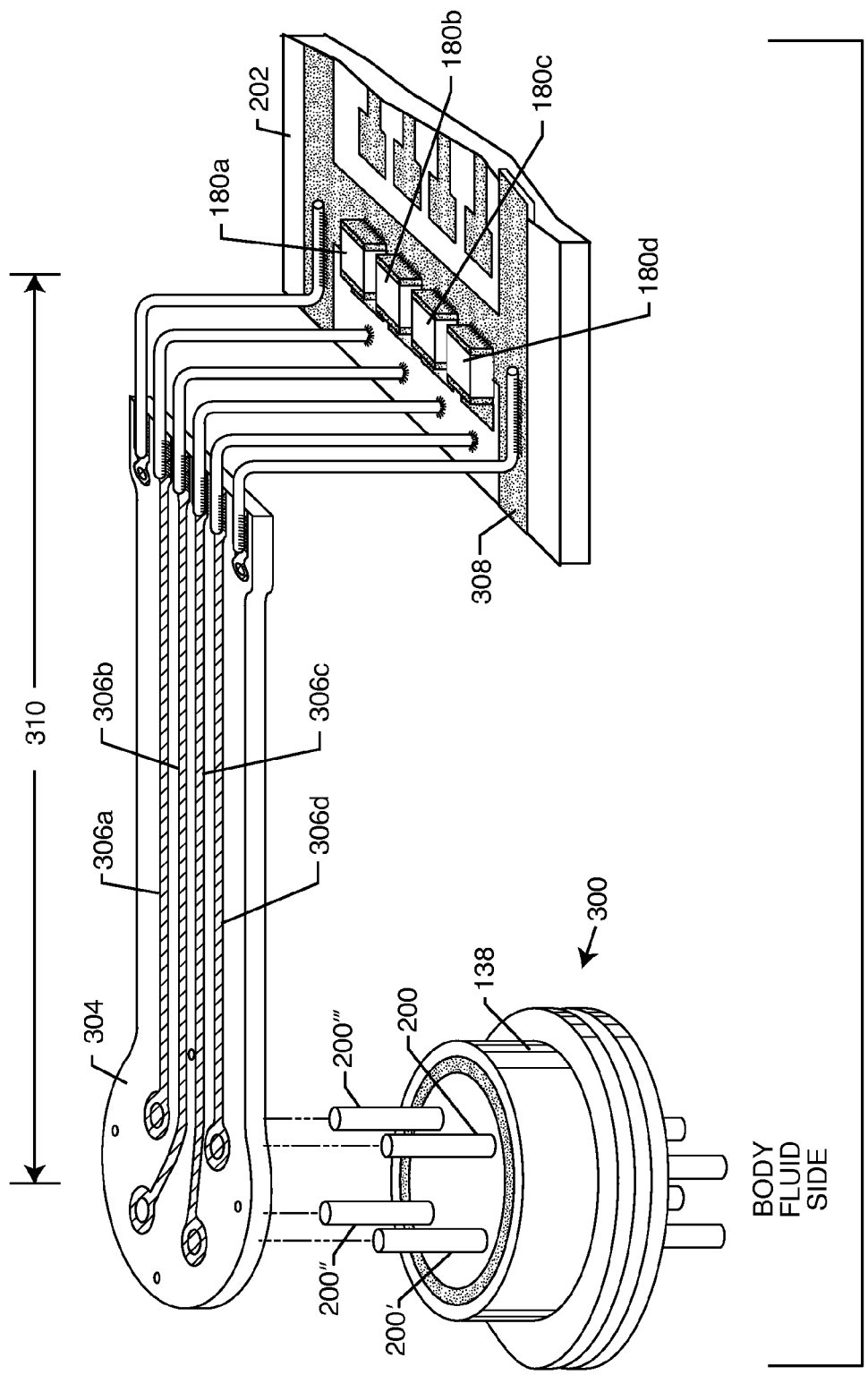
FIG. 54 illustrates a prior art connection of a flex cable to leadwires that pass through hermetic terminal in non-conductive relationship.

FIG. 54 illustrates a prior art quadpolar hermetic terminal 300 with a conductive ferrule 302. Shown are four hermetic seal terminal pins 200-200‴ and a prior art flex cable 304 with circuit traces 306a-306d that are routed to a circuit board or substrate 202. This is a prior art attempt to provide EMI filtering through MLCC capacitors 180a-180d. There is a ground connection 308 which grounds the circuit substrate. There are many attempts in the prior art to form an exposed flex cable or leadwire configuration as shown in FIG. 54. Due to lack of shielding and a high impedance ground path (loop) these attempts result in very poor EMI filter performance of the overall AIMD. The reason is the circuit path of the circuit traces 306a-306d is relatively long compared to the wavelength of most EMI energy. Therefore, these circuit traces 306a-306d become very effective re-radiating antennas. This is called "the genie in the bottle" affect. Once the EMI gets inside the overall AIMD shielded housing, it can cross-couple or re-radiate to adjacent sensitive circuits, such as pacemaker biologic sense circuits. Moreover, another problem associated with the prior art arrangement shown in FIG. 54 arises due to the narrowness of the circuit traces 306a-306d and their relatively long length 310, which creates substantial inductance and impedance. Therefore, at high frequency, this essentially puts a high ohmic impedance between the point where the terminal pins 200-200‴ ingress and the point of the attempted EMI filtering at the MLCC capacitors 180a-180d. What this means is the EMI energy that is intercepted by the MLCC capacitors 180a-180d is not effectively decoupled to the overall AIMD electromagnetic shield housing 104. This is why, in the prior art, the mounting of filter components, such as feedthrough capacitors, directly to the ferrule of the hermetic terminal has been the preferred approach.

FIG. 55 is a cross-sectional view of an improved flex cable 304' incorporating the novel features described herein, and is very similar to FIG. 54. In this case, the circuit trace 306 has been imbedded between a top shield plane 312 and a bottom shield plane 314. As described in U.S. 2009/0243756, a parasitic capacitance is desirably formed between the circuit trace 306 and the surrounding ground shield planes 314, 316. This aids in high frequency filter attenuation. FIG. 55 forms an EMI shield extension of the overall AIMD electromagnetic shield housing 104.

Figure 56:
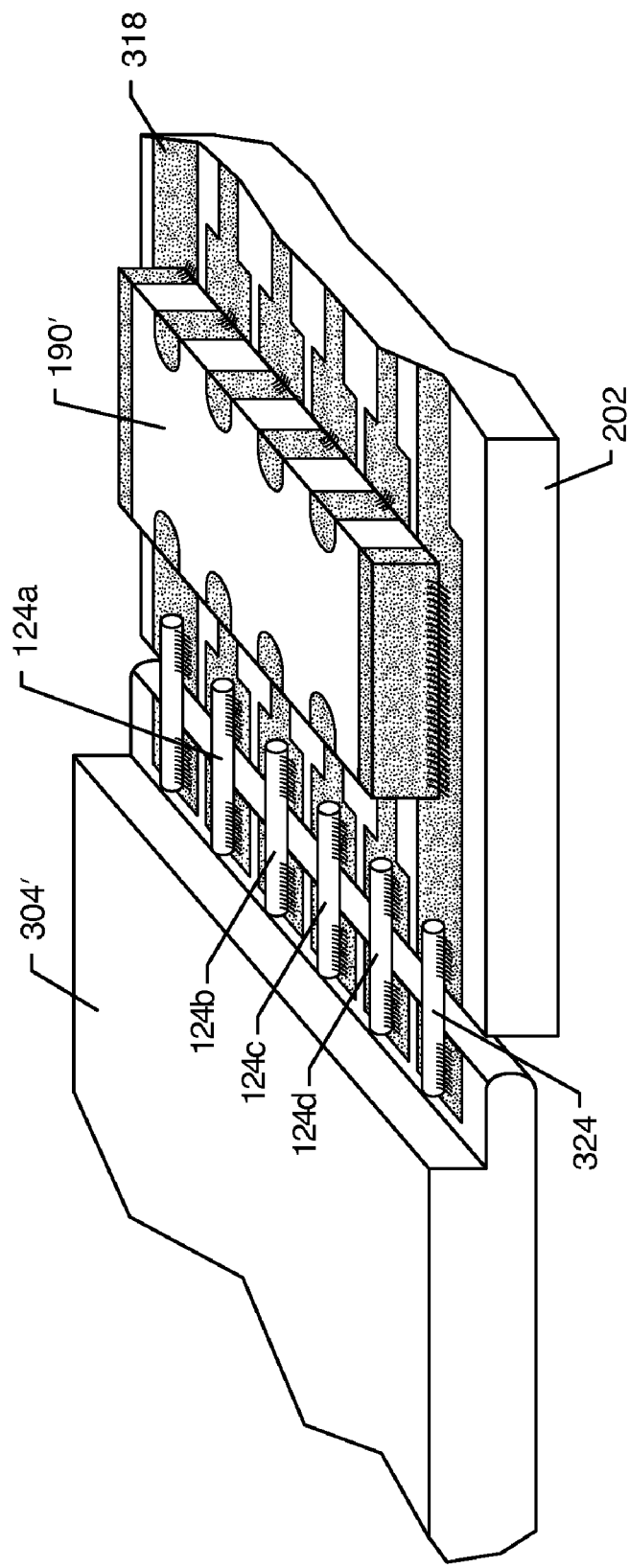
FIG. 56 is a perspective view of the flex cable of FIG. 55 connected to a circuit board or substrate having a flat-through capacitor.
Figure 57:
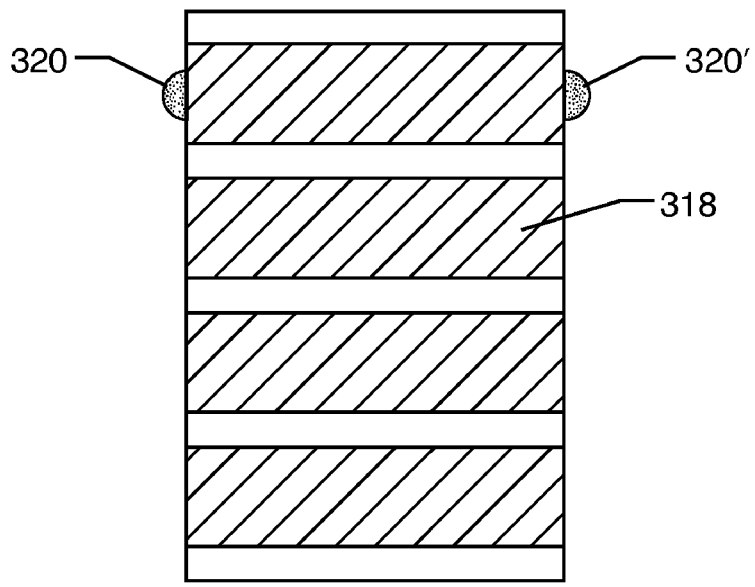
FIG. 57 illustrates the lay-up of the active electrode plate set (AEP) for the flat-through capacitor of FIG. 56.
Figure 58:
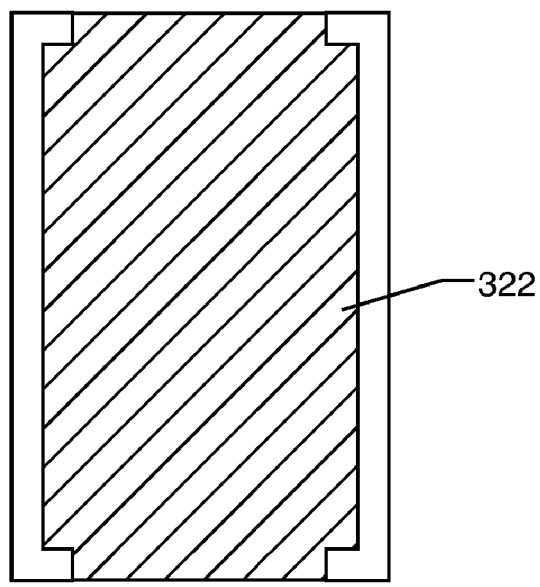
FIG. 58 illustrates the lay-up of the ground electrode plate (GEP) of the flat-through capacitor of FIG. 56.

FIG. 56 illustrates the flex cable 304' from FIG. 55 attached to circuit board 202. Shown is a surface mounted flat-through capacitor 190'. The flat-through capacitor 190' is very similar to the unipolar flat-through capacitor 190 shown in FIGS. 17 and 18, but is different in that the flat-through capacitor 190' of FIG. 56 has four capacitors with a single ground plane 318. An active electrode plate set (AEP) 318 for the flat-through capacitor 190' of FIG. 56 is shown in FIG. 57. A pair of metallization surfaces 320 and 320' correlate to those indicated in FIG. 56. A ground electrode plate (GEP) 322 is illustrated in FIG. 58. Referring once again to the ground electrode plates 318, 322 of FIGS. 57 and 58, these would typically be stacked up and interleaved to achieve the desired effective capacitance area (ECA). By having multiple active layers AEP 318 and multiple ground layers GEP 322 stacked and interleaved, one can achieve a very high capacitance value. In addition, one lowers the resistance between the metallization surfaces 320 and 320' because of the parallel plates. This increases the current handling capacity between the metallization surfaces 320 and 320' of the flat-through capacitor 190'. For the flat-through capacitor 190' to effectively act as a low pass filter, it is important that a set of ground wires 324 coming from the flex cable 304' present a very low impedance to the overall AIMD electromagnetic shield housing 104. This is best achieved through the wide ground shield plates 326, 326' as shown in FIG. 60. Referring to FIG. 60, one can see that the ground shield plates 326, 326' are stitched together with a number of conductive via holes 328 as shown. This creates a Faraday cage shield which co-extensively surrounds and shields all of the circuit traces 306a-306d (FIGS. 59 and 61).

Referring once again to FIG. 56, the flat-through capacitor 190' can be replaced or used in combination with prior art circuit board electronics, prior art high voltage suppression arrays, X2Y attenuators, other potential low pass filters, active filters and even electronic short-to-housing switch networks.

Referring once again to FIG. 56, by keeping the leadwires 124a-124d relatively short as they exit the shielded flex 304', one can prevent re-radiation or cross-coupling to adjacent circuits at high frequency. ANSI/AAMI Standard PC69 describes radiated tests in the 450 to 3000 MHz range. By keeping the circuit traces 306 that connect to a circuit board or low pass filter or flat-through filter to about 10 mm in length, one can be assured that re-radiation or coupling of EMI inside the AIMD housing will not occur.

FIG. 59 is generally taken from section 59-59 of FIG. 55. Shown are the circuit traces 306a-306d.

FIG. 60 is taken from the two layers 60-60 of FIG. 55. Accordingly, the circuit traces 306a-306d are sandwiched between the ground shield plates 326, 326' top to bottom as illustrated in FIG. 60. The ground shield plates 326, 326' of FIG. 60 serve to effectively shield the imbedded circuit traces 306a-306d from EMI. Further, the ground shield plates 326, 326' form a very low impedance path from the electronic circuit board, substrate or network 202 back to the AIMD electromagnetic shield housing 104.

FIG. 61 is generally taken from layer 61-61 of FIG. 55. This is very similar to FIG. 59 except that an edge ground 330 has been provided to further surround circuit traces 306a-306d. There are also a number of via holes 328 as shown in FIGS. 59 and 60 which help to stitch all the ground planes together. This is important so that the overall EMI shielded extension forms a Faraday cage particularly blocking any re-radiation of EMI in the frequencies of interest below 3 GHz.

Figure 62:
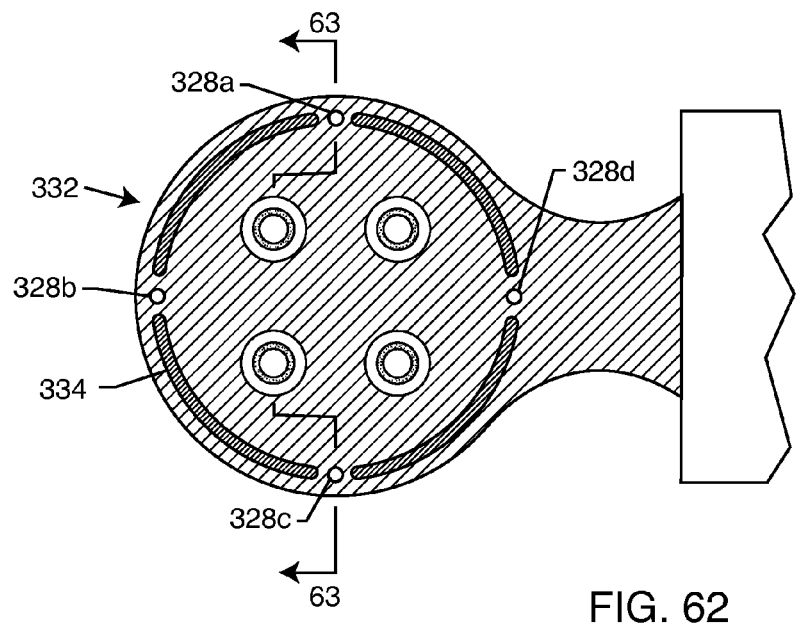
FIG. 62 illustrates the bottom shield ground of the flex cable of FIGS. 55 and 56.

FIG. 62 illustrates a bottom shield ground electrode plate 332 of the flex cable 304' from FIG. 55 and FIG. 56. One can see that a robot has dispensed a circular portion of a thermal-setting conductive material 334. This is designed to align precisely with the gold braze 158 of the hermetic terminal 100 of FIG. 63. Accordingly, the entire left end of the shielded flex cable 304' can be laid down over the hermetic terminal 110 and then the thermal-setting conductive material 334 can be cured in an oven, furnace or other equivalent process. This makes a suitable electrical and mechanical connection to the exposed bottom ground shield electrode plate 332. Referring back to FIG. 62, one will see that there are gaps left in the circumferential thermal-setting conductive material 334. These gaps are present to allow for a free flow of helium during fine leak detection. There are also via holes 328a, 328b, 328c, and 328d which are used to connect to the other internal ground shield plates, including the top shield plane 312.

Figure 63:
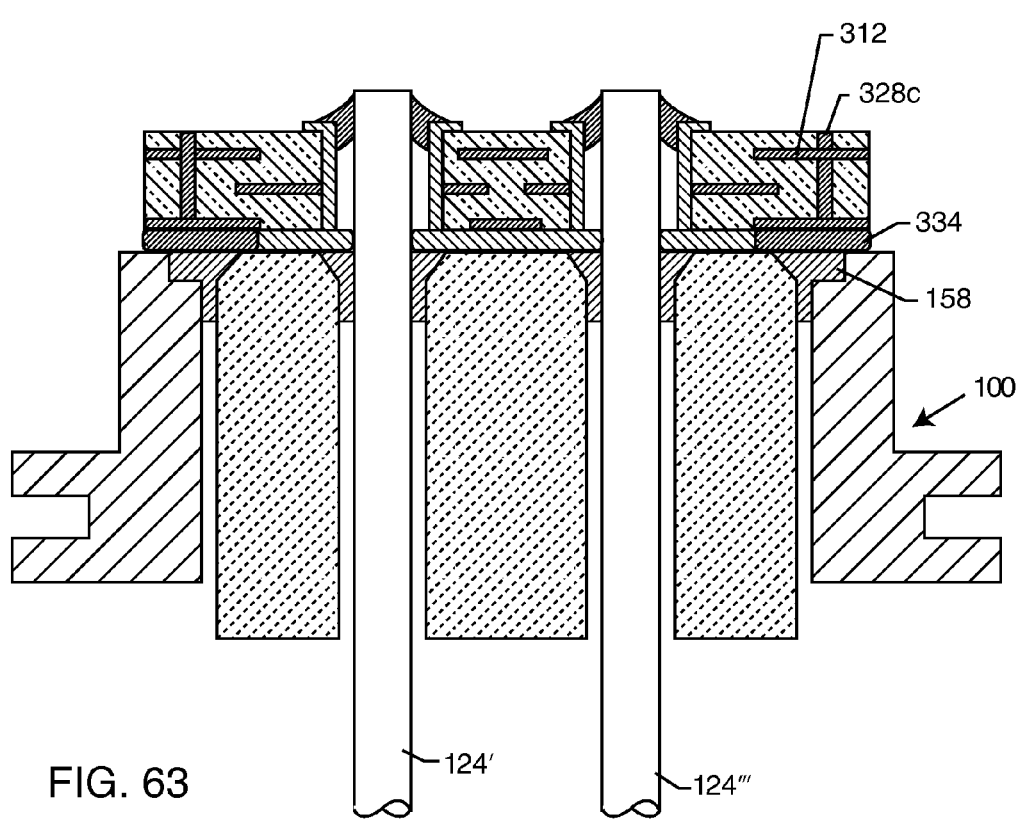
FIG. 63 is a cross-sectional view of the hermetic seal assembly taken along the line 63-63 of FIG. 55.

FIG. 63 is a sectional view of the hermetic seal 100 taken along line 63-63 from FIG. 55. One can see the electrical connection formed by the solder or thermal-setting conductive material 334 between the via hole 328c and the gold braze 158, for example. One can also see this outer connection of the thermal-setting conductive material 334 between the hermetic seal gold braze 158 and the via hole 328c. This would typically be of a ball grade array (BGA) type construction. It will be obvious to those skilled in the art that internal pins 124' and 124" could have headed leads in the location of gold braze GBS (for example, see FIGS. 9 and 10 of U.S. Pat. No. 7,012,192, which is herein incorporated by reference). Accordingly, the ball grade array type attach could be used between the via hole 328d, which could be filled, and the nail head of the leadwire 124 (not shown).

Figure 64:
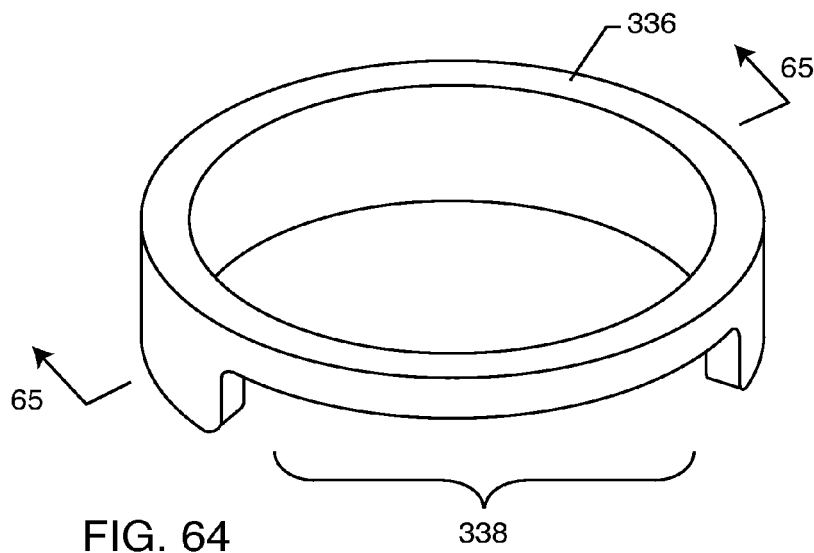
FIG. 64 is a perspective view of an attachment cap used to connect a shielded flat-through EMI filter to various types of hermetic or non-hermetic seals.

FIG. 64 illustrates a novel laser weld cap 336 with a cut out section 338. The cut out section 338 is formed or cut so the metal laser weld cap 336 can slip down over a narrow section 340 of the end of the flexible portion of the shielded flex cable 304'. The laser weld cap 336 can be a stamped titanium, machined titanium, injection molded titanium or a number of other metals.

Figure 65:
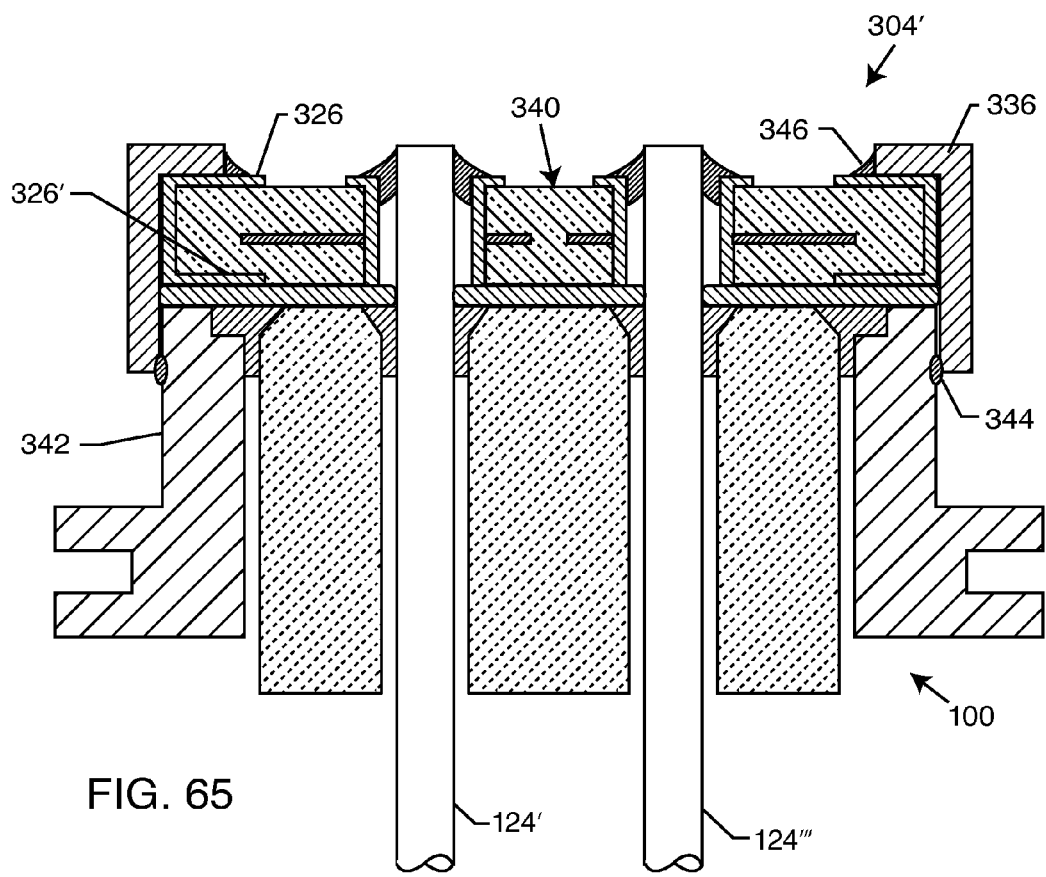
FIG. 65 is a cross-sectional view of a hermetic terminal including the cap of FIG. 64.

FIG. 65 is a combined cross-section taken generally from 63-63 of FIG. 55 and also from section 65-65 of FIG. 64. However, the shielded flex cable 304' has been modified to accommodate the novel laser weld cap 336 as illustrated in FIG. 64. In FIG. 65 one can see that the laser weld cap 336 is slipped down such that it comes into close contact with a flange 342 of the hermetic terminal 100. A continuous or discontinuous laser weld or braze 344 is formed as shown. This makes a solid metallurgical and low impedance ground contact to the hermetic flange 342 and to the laser weld cap 336. An electrical connection 346 is then made to the ground metallization 326 of the shielded flex cable 304' thereby providing a very low impedance RF ground. One can see in FIG. 65 that the ground shield plates 326 and 326' are external for the purposes of this illustration; however, they could be internal plates as previously illustrated.

Figures 66, 67:
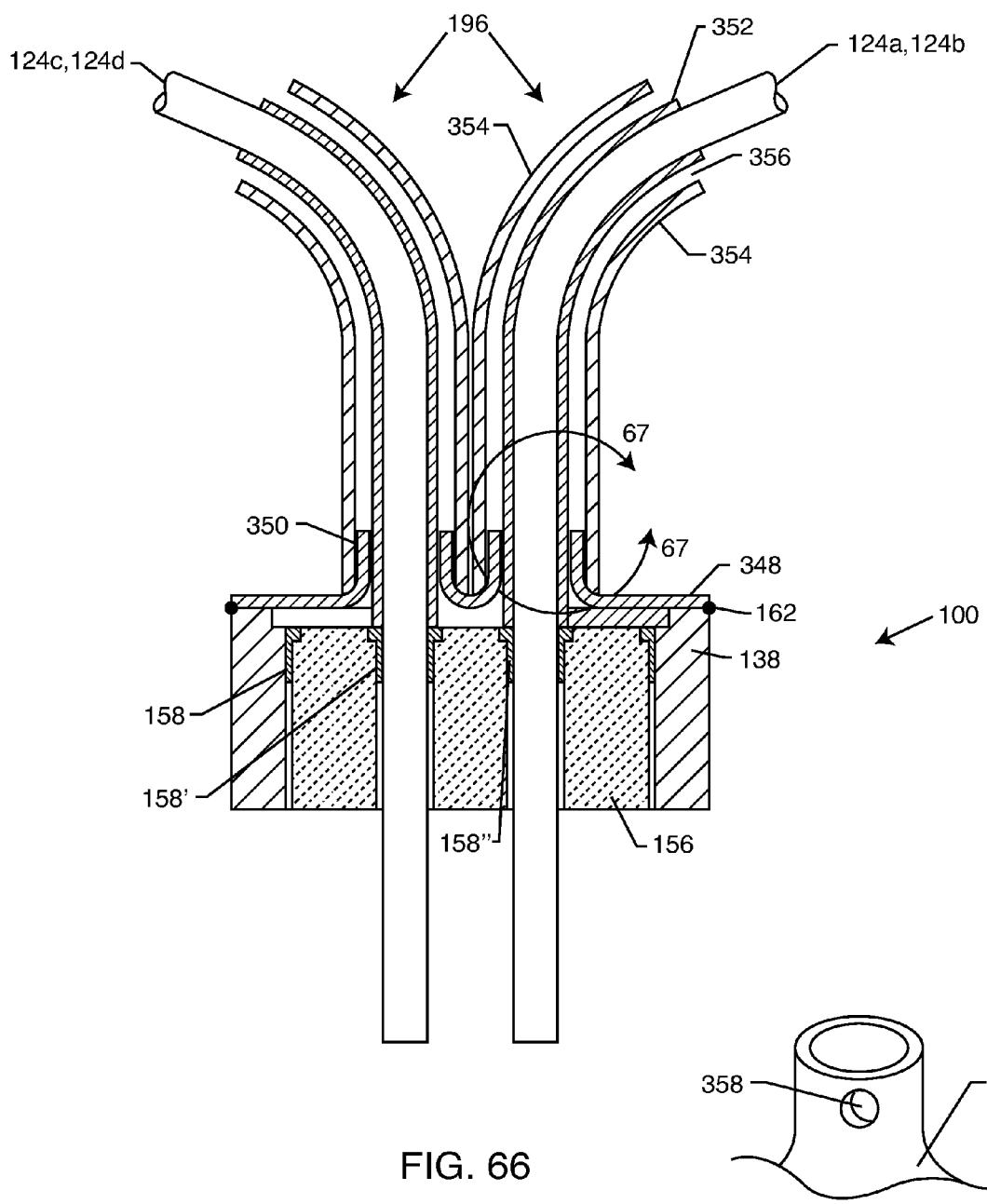
FIG. 66 is a cross-sectional view illustrating a hermetic terminal assembly embodying the present invention.
FIG. 67 is an enlarged perspective view of a cap assembly, taken generally of the area indicated by line 67-67 of FIG. 66.

FIG. 66 shows a hermetic terminal assembly 100. As previously described, the hermetic terminal subassembly 100 consists of a metallic ferrule 138 which is generally made of titanium. The ferrule 138 is gold brazed 158 and 158' to the alumina ceramic insulator 156 as shown. Gold brazes 158' and 158" form a hermetic seal between the insulator 156 and the leadwires 124a-124d. There is a novel machined, stamped, or metal formed cap assembly 348 as illustrated. In this case, this is a quadpolar cap that, of course, can be any number of holes in accordance with the embodiments described herein. These form a set of protrusions 350 which makes it very convenient to assemble the EMI shielded conduit assembly 196. First, an insulating sleeve 352 is slipped down over the leadwire 124 into the inside diameter of the protrusion 350. This is seated against the bottom adjacent to gold braze 158' or 158". The insulating sleeve 352 can be a close-fitting semi-flexible insulation sleeve or it can be a non-conductive heat-shrink tubing. In the case of heat-shrink tubing, the sleeve would be placed down as shown and then heat would be applied to shrink it in place firmly against the leadwire 124. Then in a subsequent operation, the EMI shielded conduit assembly 196 would be slipped down over the outside of the protrusion 350. In the preferred embodiment, the cap assembly 348 would be electroplated or coated so that there are no issues with oxides. Of course the cap assembly 348 can also be of suitable materials that do not form oxides. It is very important that the conductive coaxial or co-extensive EMI shielded conduit assembly 196 form a low impedance short-to-housing electrical connection to the end cap protrusion 350. In an embodiment, the EMI shielded conduit assembly 196 would be a conductive heat-shrink tubing and would be slipped down over the protrusion 350, heat would then be applied so that the tubing 354 is shrunk down and firmly adhered to the protrusion 350 of the cap assembly 348. Referring once again to FIG. 66, the heat-shrink tubing 354 is shown in its preshrunk condition. Accordingly, there is a gap 356 between the conductive EMI shield and the insulating sleeve 352. After applying heat, the heat-shrink tubing 354 would shrink down so that it also bonded against the insulating sleeve 352. The cap assembly 348 can be attached to the ferrule 138 of the hermetic terminal 100 by laser welding 162, by soldering to the gold braze 158, or by using various thermal-setting conductive adhesives that would connect between the cap assembly 348 and the gold braze 158. In all cases, it is also important that this be an oxide-free connection. The novel cap assembly 348 illustrated in FIG. 66 enables the leadwires 124a-124d to be routed to different locations inside of the AIMD electromagnetic shield housing 104. In other words, as illustrated, leads 124a, 124b can be routed off to the right and leads 124c, 124d can be routed to another location. This is important in modern AIMDs which can have as many as twelve or more leadwires and multiple electronic circuit boards or substrates.

FIG. 67 is taken generally from section 67-67 in FIG. 66. FIG. 67 illustrates the details of the cap assembly 348 that has a through hole 358. One or more through holes 358 can be provided for convenient brazing or laser welding. This would be very useful if the metallic shielding was of the type as previously illustrated in FIG. 32 or 33. This is also particularly suitable if the EMI shielded conduit assembly 196 is of braided shield wire.

Figure 68:
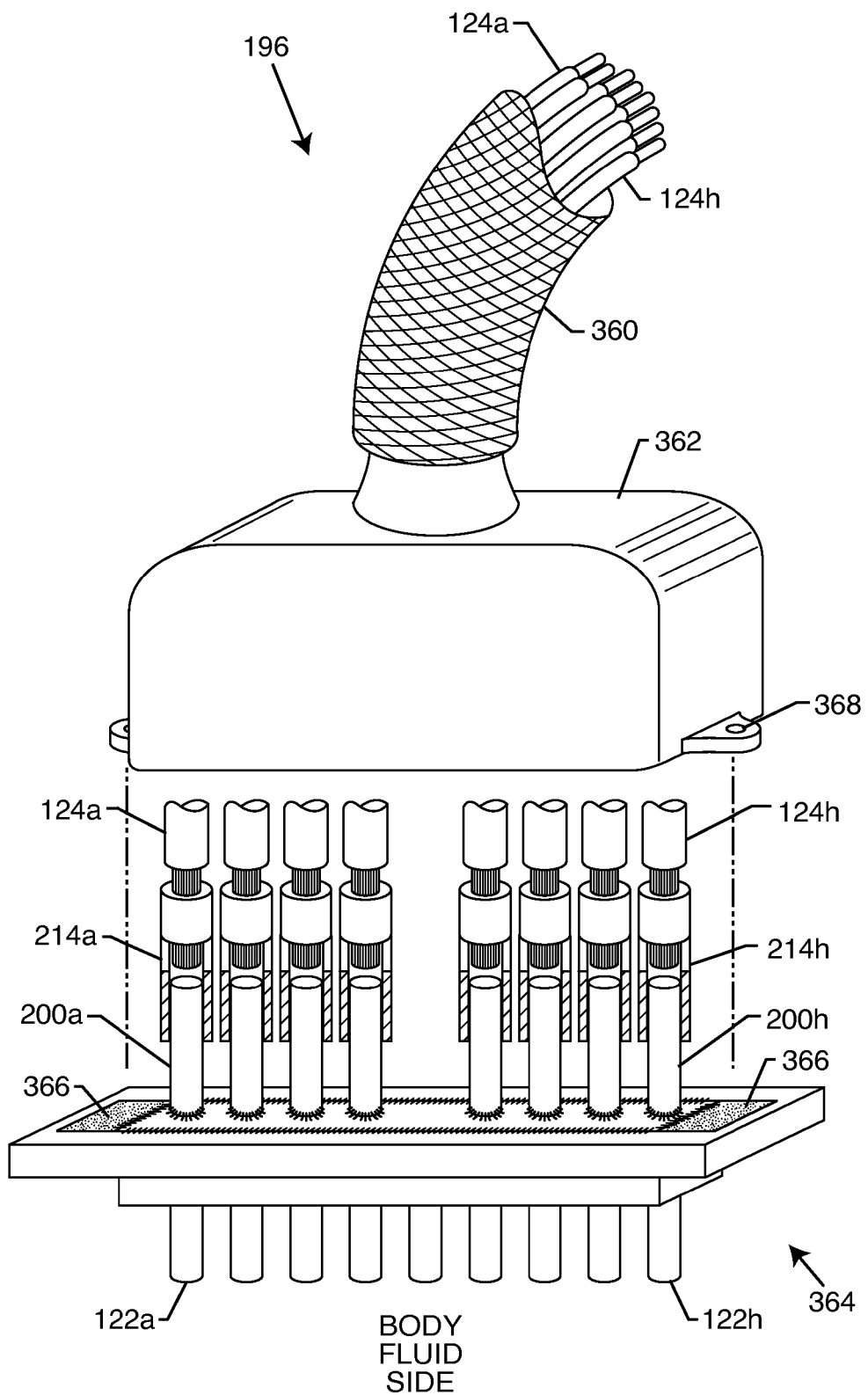
FIG. 68 is a perspective view of a cylindrical or coaxial shielded conduit attached to a stamped or machine metallic lid cover to shield an inline octa-polar assembly.

FIG. 68 illustrates a novel application of a cylindrical or coaxial shielded conduit 360 attached to a stamped or machined metallic lid cover 362. The lid cover 362 makes a transition from coaxial to rectangular geometry. Also shown is a hermetic terminal assembly 364 which is known as an inline octa-polar (8-pin) assembly. Leadwires 124, in this case, 124a-124h, are attached using a splice or the previously described circuit junction connection 214. This would be shown eight times attached to the terminal pins 200. The hermetic insulator has a set of gold braze pads 366 that are designed to mate with the mounting tabs and holes 368 of lid cover 362. In manufacturing, first the connection to the terminal pins 200 is made using the circuit junction connectors 214, then the lid cover 362 and the EMI shielded conduit assembly 196 along with its associated attached coaxial shielded conduit 360 is pressed down and seated onto the gold braze pads 366. Then a solder joint, braze or laser weld is made so that the two are electrically and mechanically joined.

Figure 69:
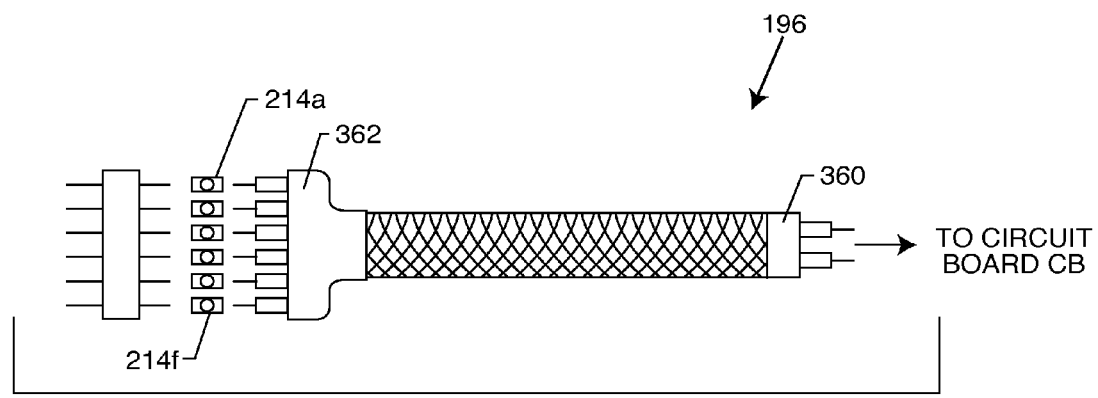
FIG. 69 is a diagrammatic view of the full length of the EMI shielded conduit of FIG. 68.

FIG. 69 illustrates the full length of the EMI shielded conduit assembly 196 previously described in FIG. 68. Shown on the left is the stamped lid cover 362 and on the right is the coaxial shielded conduit 360. The EMI shielded conduit assembly 196 is electrically and mechanically attached to both the coaxial shielded conduit 360 and the lid cover 362. The assembly shown in FIG. 69 can be preassembled and pre-tested such that it is ready for attachment to the hermetic seal 198 and a circuit board 202 (not shown).

Figure 70:
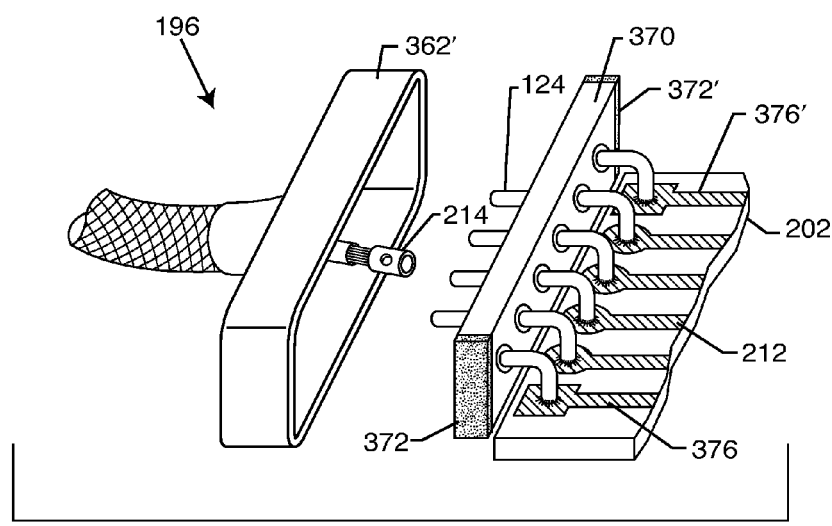
FIG. 70 is a partially exploded perspective view of a shield conduit and cover spaced from a feedthrough capacitor.
Figure 71:
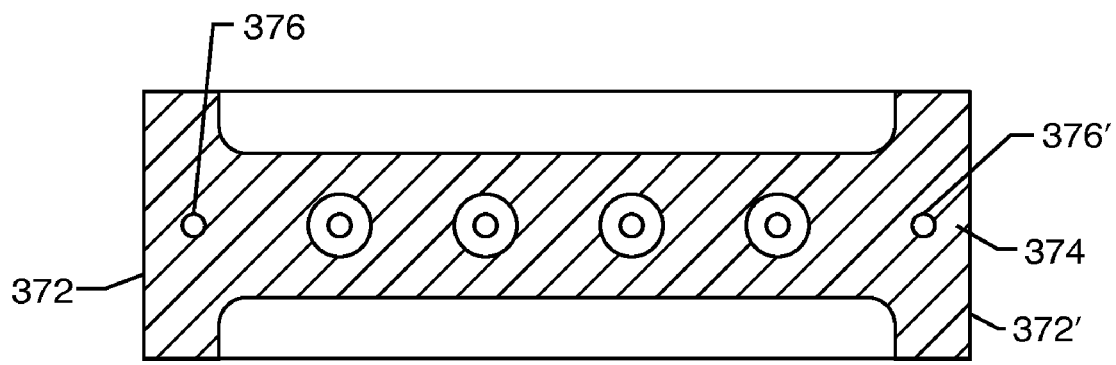
FIG. 71 illustrates internal ground electrode plates (GEP) of the feedthrough capacitor of FIG. 70.
Figure 72:
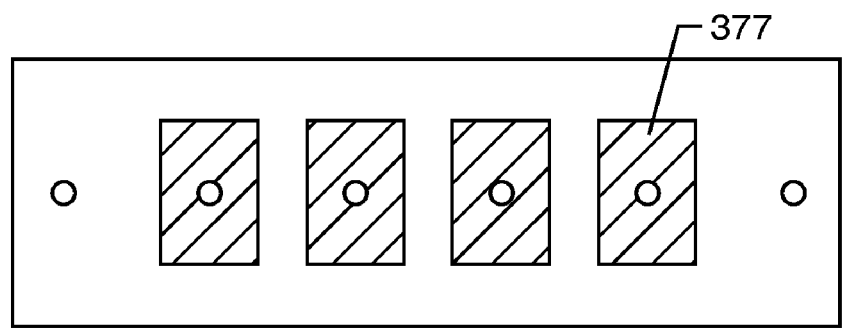
FIG. 72 illustrates internal active electrode plates (AEP) of the feedthrough capacitor of FIG. 70.

FIG. 70 is taken from FIGS. 68 and 69 except that the right-hand lid cover 362' is rectangular. The circuit junction connection 214 is used to attach to a substrate or even a feedthrough capacitor 370 as shown. After the leadwires 124 pass through the feedthrough capacitor 370, they are then attached to the circuit traces 212 on the circuit board 202. Referring to FIG. 70, one can see a pair of metallization surfaces 372 and 372' on the feedthrough capacitor 370. These correspond with connections to the feedthrough capacitor 370 internal ground electrode plates (GEP) 374 as illustrated in FIG. 71. The metallization surface 372 is designed to be soldered to the lid cover 362'. This extends the RF ground all the way from the housing of the AIMD through the hermetic terminal 198 of ferrule 138, through the EMI shielded conduit assembly 196 to the lid cover 362 and then to the internal ground electrode plate set 374 of the flat-through capacitor 370; and even to the circuit board 202 and the ground plane 376. Thus, the AIMD electromagnetic shield housing 104 may extend all the way to the internal ground electrode plate 374 for the feedthrough capacitor 370 and/or the circuit board 202 and the ground plane 376, 376'. A set of active electrode plates AEP 377 of the feedthrough capacitor 370 are illustrated in FIG. 72.

Figure 73:
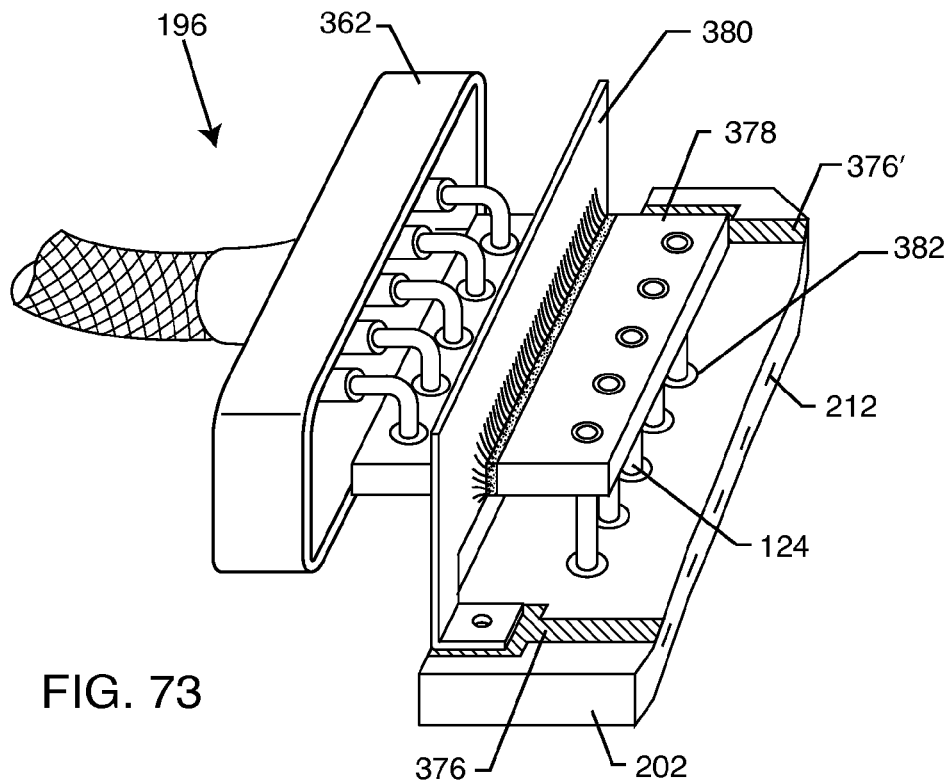
FIG. 73 is a perspective view illustrating a flat-through capacitor mounted to a shield plate designed to be soldered to a cover assembly.

FIG. 73 illustrates an alternative to FIG. 70 in that a novel design flat-through capacitor 378 is shown mounted into a shielded plate 380 which is designed to be soldered in to the lid cover 362. Short leadwires 124 are fed from the flat-through capacitor 378 down to a set of via holes 382 in the circuit board 202.

Figure 74:
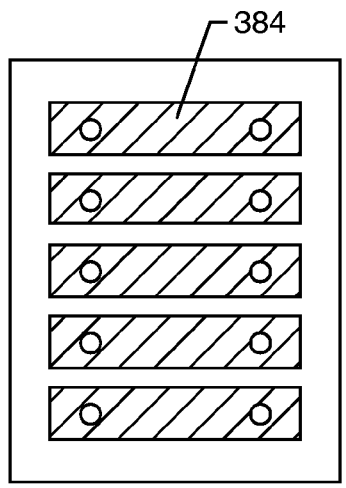
FIG. 74 illustrates the lay-up of the active electrode plates (AEP) of the flat-through capacitor of FIG. 73.
Figure 75:
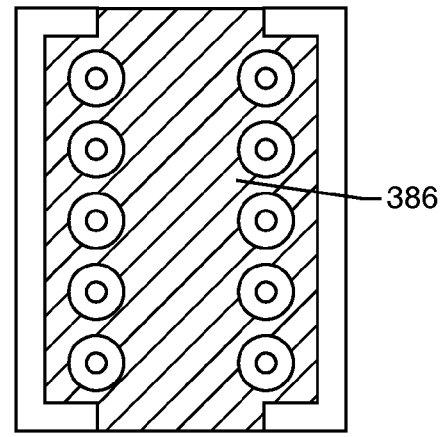
FIG. 75 illustrates a ground electrode plate (GEP) of the flat-through capacitor of FIG. 73.

FIGS. 74 and 75 illustrate an active electrode plate set (AEP) 384 and a ground electrode plate set (GEP) 386 of the flat-through capacitor 378, respectively. Of course, these can be interleaved and stacked up to form as many layers as are required to receive the desired capacitance and filtering values. The design of FIG. 73 is particularly suitable where microwave high frequency EMI is a concern. This is a completely shielded assembly which allows no possible leakage of high frequency EMI around the flat-through capacitor 378'.

FIG. 76 illustrates yet another alternative to the designs previously described in FIGS. 70 and 73. The novel flat-through capacitor 378' shown in cross-section in FIG. 76 is designed to be installed and have its outside perimeter metallization electrically and mechanically connected directly to the inside or a surface of the lid cover 362. Leadwires 124 are connected to a through hole in the novel flat-through capacitor 378' and electrically connected at location 388 as shown. Then a short pin 390 is electrically connected on the other side of the flat-through capacitor 378' at electrical location 392. This pin 390 can be soldered to a circuit land wire bond pad or through the via hole 382, as shown, to connect to the electric circuit traces 212 of the circuit board 202. Again, the cross-sectional view as illustrated in FIG. 76 completely stops any re-radiation of EMI inside the AIMD housing and will work at very high frequency.

Figure 77:
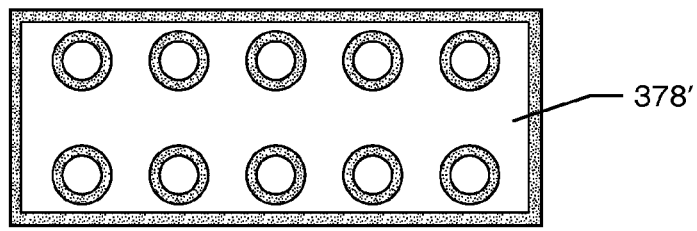
FIG. 77 is an end view of the feedthrough capacitor, taken from the perspective of arrow 77 of FIG. 76.
Figure 78:
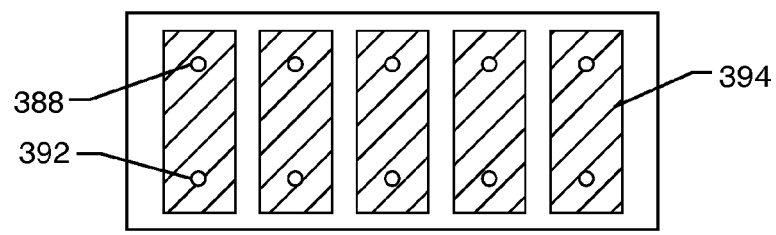
FIG. 78 illustrates the active electrode plates (AEP) of the flat-through capacitor of FIG. 76.
Figure 79:
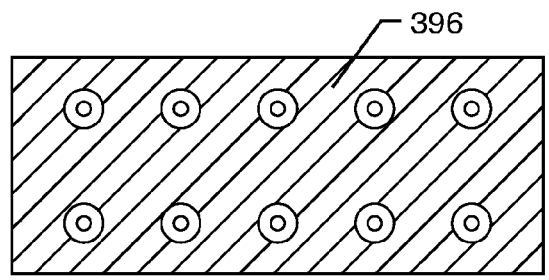
FIG. 79 illustrates the ground electrode plate (GEP) of the flat-through capacitor of FIG. 76.

FIG. 77 is an end view of the flat-through capacitor 378' taken from FIG. 76. FIG. 78 illustrates an active electrode plate (AEP) 394 of the flat-through capacitor 378' described in FIG. 76. FIG. 79 illustrates a ground electrode plate (GEP) 396 of the novel flat-through capacitor 378' of FIG. 76.

From the foregoing, it will be appreciated that the EMI shielded conduit assembly for active implantable medical devices offer a number of very important advantages. These include removal from the hermetic terminal and the necessity to mount filtering components, such as prior art feedthrough capacitors. Feedthrough capacitors are not only expensive, but they are difficult to mount. As mentioned, mounting of such components on the hermetic terminal can block or mask the possibility of detecting a defective hermetic seal (helium leak test). Modern low cost manufacturing techniques generally consist of robotic manufacturing using pick and place components that are disposed on circuit boards and substrates. This has never been achievable with a prior art AIMD hermetic terminal. However, it is relatively easy to achieve when one has a flat circuit board or substrate. The present invention enables the mounting of RF sensitive components at a distance remote from the hermetic terminal by providing a novel EMI shielded conduit assembly which also provides a very low impedance or RF ground to the circuit board. This enables the mounting of filter components, such as prior art feedthrough capacitors, low pass filters, MLCC chip capacitors, flat-through capacitors or X2Y attenuators using robotic techniques on an electronic circuit board, substrate or network of the AIMD. By providing a very low impedance RF ground which is an extension of the overall AIMD electromagnetic shield housing, one can also place a number of other components on the electronic circuit board, substrate or network. These include high voltage suppression arrays, bandstop filters, L-C trap filters, various combinations of these with low pass filters, electronic filters and even short-to-housing microelectronic switch arrays. These offer tremendous advantages when the AIMD is exposed to extreme environments, such as the RF field produced by magnetic resonance imaging equipment. By having a very low impedance RF ground present at the circuit board level, one can redirect RF energy induced by MRI RF fields onto implanted leads to the housing of the electromagnetically shielded housing of the AIMD. Since the AIMD housing has a much larger surface area when compared to an implanted electrode, it is capable of dissipating energy without significant temperature rise over this large surface area. This protects against tissue damage that can be caused by excessive energy (heat) being deposited in leads and/or electrodes in contact with body tissue.

In its simplest form, the present invention eliminates the need to mount a low pass filter or other components on or adjacent to the hermetic terminal for the AIMD housing, and instead allows the position of the desired filter or other components on a remote electronic circuit board, substrate or network. Moreover, in some instances, the present invention eliminates altogether the need for the low pass filter and its associated size and complexity by providing a low inductance conductive extension of a equipotential housing.

An important feature of the present invention is that it also reduces the effective unshielded lead length of leadwires routed from the hermetic terminal inside the AIMD housing. That is, by providing an overall shield around most of or all the length of these internal leadwires, their effective wavelength is reduced. Therefore, they become very ineffective re-radiating or coupling antennas. By keeping electronic circuit board, substrate or network circuit trace elements relatively short, they also do not become effective antennas below 3 GHz. For this reason, in certain AIMD embodiments, one does not even require the use of filter capacitors or multi-element low pass filters. This is particularly true of AIMDs that do not sense, such as most neurostimulators.

Although several embodiments of the invention have been described in detail for purposes of illustration, various modifications of each may be made within the spirit and the scope of the invention. Accordingly, the invention is not to be limited except to set forth in the accompanying claims.

What is claimed is:

1. An EMI shielded conduit assembly for an active implantable medical device (AIMD), comprising:
    a) an AIMD comprising a housing;
    a hermetic feedthrough terminal comprising a ferrule supporting an insulative material sealing between at least one conductive leadwire and an inner surface of the ferrule, wherein the ferrule is hermetically sealed and electrically connected to the AIMD housing;
    c) an electronic circuit board or substrate disposed within the AIMD housing remote from the hermetic feedthrough terminal;
    d) at least one capacitor mounted on the circuit board or substrate and comprising spaced apart first and second electrode plates encased in a dielectric material, wherein the at least one leadwire extends from the feedthrough terminal to a proximal end of the leadwire electrically connected to the first electrode plates of the capacitor mounted on the circuit board or substrate; and
    e) an EMI shield comprising a substantially continuous covering that is in a non-conductive relationship around an outer perimeter of the at least one leadwire, but that conductively extends along the length thereof from a distal shield end electrically connected to the ferrule to a proximal shield end electrically connected to the second electrode plates of the capacitor mounted on the remote electronic circuit board or substrate.

2. The EMI shielded conduit assembly of claim 1, wherein the electronic circuit board or substrate comprises a low pass EMI filter, an L-C trap, a bandstop filter, or a combination thereof.

3. The EMI shielded conduit assembly of claim 2, wherein the low pass EMI filter and the L-C trap are grounded to the EMI shield.

4. The EMI shielded conduit assembly of claim 2 or 3, wherein the low pass EMI filter comprises a capacitor.

5. The EMI shielded conduit assembly of claim 4, wherein the low pass EMI filter comprises a feedthrough capacitor, an MLCC chip capacitor, a flat-through capacitor, an X2Y attenuator, or a multi-element low-pass filter, or a combination thereof.

6. The EMI shielded conduit assembly of claim 2 or 3, wherein the low pass EMI filter comprises an active electronic filter.

7. The EMI shielded conduit assembly of claim 1 or 2, including a high voltage suppression network associated with the remote electronic circuit board or substrate.

8. The EMI shielded conduit assembly of claim 7, wherein the high voltage suppression network is grounded to the EMI shield.

9. The EMI shielded conduit assembly of claim 7, wherein the high voltage suppression network comprises a diode array.

10. The EMI shielded conduit assembly of claim 1, wherein the electronic circuit board or substrate comprises a programmable short-to-housing switch network.

11. The EMI shielded conduit assembly of claim 1, wherein the AIMD housing comprises a conductive equipotential surface.

12. The EMI shielded conduit assembly of claim 11, wherein the AIMD housing comprises a metallic can.

13. The EMI shielded conduit assembly of claim 2 or 3, wherein the low pass filter, the L-C trap, or the bandstop filter is disposed on the circuit board or the substrate.

14. The EMI shielded conduit assembly of claim 13, wherein the EMI shield extends from the hermetic feedthrough terminal to the low pass EMI filter, the L-C trap, or the bandstop filter.

15. The EMI shielded conduit assembly of claim 1, wherein the at least one leadwire comprises a plurality of leadwires, and the EMI shield comprises at least two EMI shields conductively coupled to the AIMD housing and each substantially co-extending about at least one respective leadwire in non-conductive relation.

16. The EMI shielded conduit assembly of claim 15, including a non-conductive insulator disposed between each leadwire and its respective EMI shield.

17. The EMI shielded conduit assembly of claim 1 or 16, wherein the EMI shield comprises a conductive heat-shrink tubing.

18. The EMI shielded conduit assembly of claim 1, wherein the EMI shield comprises a conductive foil, wire, braid, mesh, circuit trace, or solid tubular material.

19. The EMI shielded conduit assembly of claim 9, wherein the EMI shield is radially spaced from the at least one leadwire.

20. The EMI shielded conduit assembly of claim 18, including a flex cable embodying the at least one leadwire and the EMI shield.

21. The EMI shielded conduit assembly of claim 1 wherein the leadwire includes at least one inductor intermediate the housing and the capacitor.

22. An EMI shielded conduit assembly for an active implantable medical device (AIMD), comprising:
   a) an AIMD comprising a housing;
   b) a hermetic feedthrough terminal comprising an insulative material sealing between at least one conductive leadwire and an inner surface of an opening in the housing;
   c) an electronic circuit board or substrate disposed within the AIMD housing remote from the hermetic feedthrough terminal;
   d) at least one capacitor mounted on the circuit board or substrate and comprising spaced apart first and second electrode plates encased in a dielectric material, wherein the at least one leadwire extends from the housing to a proximal end of the leadwire electrically connected to the first electrode plates of the capacitor mounted on the circuit board or substrate; and
   e) an EMI shield comprising a substantially continuous covering that is in a non-conductive relationship around an outer perimeter of the at least one leadwire, but that conductively extends along the length thereof from a distal shield end electrically connected to the housing to a proximal shield end electrically connected to the second electrode plates of the capacitor mounted on the remote electronic circuit board or substrate.

* * * * *